US008647637B2

(12) United States Patent
Kapil

(10) Patent No.: US 8,647,637 B2
(45) Date of Patent: Feb. 11, 2014

(54) IMMUNOGENIC COMPOSITIONS, VACCINES AND DIAGNOSTICS BASED ON CANINE DISTEMPER VIRUSES CIRCULATING IN NORTH AMERICAN DOGS

(75) Inventor: Sanjay Kapil, Stillwater, OK (US)

(73) Assignee: The Board of Regents for Oklahoma State University, Stillwater, OK (US)

( * ) Notice: Subject to any disclaimer, the term of this patent is extended or adjusted under 35 U.S.C. 154(b) by 635 days.

(21) Appl. No.: 12/696,983

(22) Filed: Jan. 29, 2010

(65) Prior Publication Data

US 2010/0196420 A1 Aug. 5, 2010

Related U.S. Application Data

(60) Provisional application No. 61/148,791, filed on Jan. 30, 2009.

(51) Int. Cl.
A61K 39/12 (2006.01)
A61K 39/175 (2006.01)
C12Q 1/70 (2006.01)
C12P 19/38 (2006.01)
C12P 19/34 (2006.01)

(52) U.S. Cl.
USPC ........... 424/204.1; 424/213.1; 435/5; 435/87; 435/91.1; 435/91.3; 435/91.33

(58) Field of Classification Search
None
See application file for complete search history.

(56) References Cited

U.S. PATENT DOCUMENTS

| 4,193,990 | A | 3/1980 | Appel et al. |
| 4,193,991 | A | 3/1980 | Appel et al. |
| 4,303,645 | A | 12/1981 | Carmichael et al. |
| 4,971,793 | A | 11/1990 | Wood et al. |
| 5,082,767 | A | 1/1992 | Hatfield et al. |
| 5,814,510 | A | 9/1998 | Parrish et al. |
| 5,882,652 | A | 3/1999 | Valdes et al. |
| 5,885,585 | A | 3/1999 | Parrish et al. |

FOREIGN PATENT DOCUMENTS

| WO | 0200883 A2 | 1/2002 |
| WO | 2008121992 | 10/2008 |

OTHER PUBLICATIONS

Stephesen, et al. Canine Distemper Virus (CDV) Infection of Ferrets as a Model for Testing *Morbillivirus* Vaccine Strategies: NYVAC- and ALVAC-Based CDV Recombinants Protect against Symptomatic Infection. J. Virology. 1997; 71(2): 1506-1513.*

Pardo, et al. Phylogenetic Characterization of Canine Infected Dogs in North America Distemper Viruses Detected in Naturally. J. Clin. Microbiol. 2005, 43(10):5009-5017.*

(Continued)

*Primary Examiner* — Jeffrey Stucker
*Assistant Examiner* — Stuart W Snyder
(74) *Attorney, Agent, or Firm* — Fellers, Snider, Blankenship, Bailey & Tippens, P.C.; Terry L. Watt

(57) ABSTRACT

Immunogenic compositions and broad-spectrum vaccines containing newly identified isolates of canine distemper virus (CDV) collected from a geographic area are provided. The newly identified isolates exhibit attributes of both European wildlife lineage CDV and one or both of Arctic and American-2 lineage CDV. Therefore, the vaccines are broadly protective against infection with European wildlife lineage CDV and either Arctic lineage CDV or American-2 lineage CDV, or both Arctic and American-2 lineage CDV.

16 Claims, 24 Drawing Sheets

(56) References Cited

OTHER PUBLICATIONS

Demeter, Zoltan, et al., "Controversial results of the genetic analysis of a canine distemper vaccine strain", "Veterinary Microbiology", 2010, pp. 420-426, vol. 142, Publisher: Elsevier, Published in: US.

Kapil, S., etc., "(P26-1) Isolation, Molecular Characterization, and Epidemiology of Canine Distemper Virus Isolates Circulating in USA (2", Jul. 12, 2008, Publisher: Poster: American Society for Virology, Cornell University, Ithaca, NY (Jul. 12-16, 2008), Published in: Ithaca, NY.

Mochizuki, Masami, et al., "Complement-Mediated Neutralization of Canine Distemper Virus in Vitro: Cross-Reaction between Vaccine Onderstepoort an", "Clinical and Diagnostic Laboratory Immunology", Jul. 1, 2002, pp. 921-924, vol. 9, No. 4, Publisher: American Society of Microbiology.

Plotkin, Joshua B., et al., "Codon bias and frequency-dependent selection on the hemagglutinin epitopes of influeza A virus", Jun. 10, 2003, pp. 7152-7157, vol. 100, No. 12, Publisher: PNAS, Published in: US.

Talbott, Jessica, et al., "Multiple Canine Distemper Virus Genotypes Are Circulating in the USA", Jul. 2009, Abstract: NIH Summer Scholars Program at OSU, Stillwater, OK, Published in: Stillwater, OK.

Zhao, Jian-Jun, et al., "Phylogenetic analysis of the haemagglutinin gene of canine distemper virus strains detected from breeding foxes, raccoon", "Veterinary Microbiology", 2010, pp. 34-42, vol. 140, Publisher: Elsevier, Published in: US.

Database Uniprot, "Hemagglutinin; Database accession No. Q52T50", May 24, 2005, Published in: US.

Pardo, et al., "Canine distemper virus isolate 19876 fusion protein and hemagglutinin genes, complete cds", May 1, 2005, Published in: US.

Hershberg, et al., "Selection on Codon Bias", "The Annual Review of Genetics", 2008, pp. 287-299, vol. 42, Publisher: Annual Reviews, Published in: US.

Kapil, et al., "Canine Distemper Virus Strains Circulating Among North American Dogs", "Clinical and Vaccine Immunology", Apr. 2008, pp. 707-712, vol. 15, No. 4, Publisher: American Society for Microbiology, Published in: US.

Kijak, et al., "Lost in Translation: Implications of HIV-1 Codon Usage for Immune Escape and Drug Resistance", "AIDS Reviews", 2004, pp. 54-60, vol. 6, Published in: US.

Lan, et al., "Pathogenesis and phylogenetic analyses of canine distemper virus strain 007Lm , a new isolate in dogs", "Veterinary Microbiology", Oct. 31, 2005, pp. 197-207, vol. 110, No. 3-4, Publisher: Elsevier B.V., Published in: US.

Martella, et al., "Heterogeneity within the hemagglutinin genes of canine distemper virus (CDV) strains detected in Italy", "Veterinary Microbiology", Sep. 10, 2006, pp. 301-309, vol. 116, No. 4, Publisher: Elsevier B.V., Published in: US.

McCarthy, et al., "Pathogen evolution and disease emergence in carnivores", "The Royal Society", Oct. 22, 2007, pp. 3165-3174, vol. 274, No. 1629, Publisher: Proceedings of The Royal Society, Published in: US.

Mueller, et al., "Live attenuated influenza virus vaccines by computer-aided rational design", "Nature Biotechnology", Jun. 13, 2010, pp. 15, Publisher: Natura America, Published in: US.

Pardo, et al., "Phylogenetic Characterization of Canine Distemper Viruses Detected in Naturally Infected Dogs in North America", "Journal of Clinical Microbiology", Oct. 2005, pp. 5009-5017, vol. 43, No. 10, Publisher: American Society for Microbiology, Published in: US.

Pepin, et al., "Genomic Evolution in a virus under specific selection for host recognition", "Infection, Genetics and Evolution", Aug. 6, 2008, pp. 825-834, vol. 8, Publisher: Elsevier, Published in: US.

Runkler, et al., "Sorting signals in the measles virus wild-type glycoproteins differently influence virus spread in polarized epithelia a", "Journal of General Virology", Jun. 25, 2009, pp. 2474-2482, vol. 90, Publisher: SGM Journals, Published in: US.

European Patent Office Invitation to Pay Additional Fees, International Application PCT/US2010/022639, mailed Apr. 27, 2010.

European Patent Office PCT International Search Report, International Application PCT/US2010/022639, mailed Jul. 5, 2010.

European Patent Office PCT Written Opinion, International Application PCT/US2010/022639, mailed Jul. 5, 2010.

PCT/US2010/022639, International Preliminary Report on Patentability, Issued: Aug. 2, 2011, 10 pages.

\* cited by examiner

07091030
AAGGTGAATTTTACTAACTACTGCGATACAATTGGGATCAGAAAATCTATTGCATCGGCAGCAAATCCCATCCT
CCTGTCAGCACTCTCTGGGGGCAGAGGTGACATATTCCCACCATACAGATGCAGTGGAGCTGCTACCTCAGTAG
GCAGAGTTTTCCCCCTATCAGTGTCATTGTCCATGTCTTTGATCTCAAGAAAATCAGAGATAATCAATATGCTA
ACCGCTATCTCAAACGGAGTGTATGGTAAAACTTATTTACTAGTGCCTGATTATATTGAAGAGGAGTTCGACAC
ACAAAAGATTCGAGTCTTTGAGATAGGGTTCATCAAACGGTGGCTGAATGACATGCCATTACTCCAGACAACCA
ACTATATGGTCCTCCCAGAGAATTCCAAAGCTAAGGTATGTACTATAGCAGTGGGCGAGTTGACACTGGCTTCC
TTGTGTGTAGGTGAGAGCACCGTGTTGTTATATCATGACAGCAATGGTTCGCAAGATAGTATCCTAGCAGTGAC
GCTGGGAATATTTGGGGCAACAACTATGGATCAAGTTGAAGAGGTGATACCTGTTGCTCACCCATCAGTAGAAA
AAATACATATAACAAATCACCGTGGGTTCATAAAAGATTCAATAGCAACCTGGATGGTGCCTGCATTGGTCTCT
GAGAAACAGGAAGAGCAAAAAAATTGTCTGGAGTCGGCTTGTCAAAGAAAATCCTACCCTATGTGCAACCAAAC
GTCATGGGAACCCTTCGGAGGAGGACAGTTGCCATCTTATGGGCGGTTGACATTACCTCTAGATCCAAGCACTG
ACCTTCAACTTAACATATCGTTTACATACGGTCCGGTTATACTGAATGGAGA (SEQ ID NO:1)

FIG. 1

07091031
GGTGAATTTTACTAACTACTGCGATACAATTGGGATCAGAAAATCTATTGCATCGGCAGCAAATCCCATCCTCC
TGTCAGCACTCTCTGGGGGCAGAGGTGACATATTCCCACCATACAGATGCAGTGGAGCTGCTACCTCAGTAGGC
AGAGTTTTCCCCCTATCAGTGTCATTGTCCATGTCTTTGATCTCAAGAAAATCAGAGATAATCAATATGCTAAC
CGCTATCTCAAACGGAGTGTATGGTAAAACTTATTTACTAGTGCCTGATTATATTGAAGAGGAGTTCGACACAC
AAAAGATTCGAGTCTTTGAGATAGGGTTCATCAAACGGTGGCTGAATGACATGCCATTACTCCAGACAACCAAC
TATATGGTCCTCCCAGAGAATTCCAAAGCTAAGGTATGTACTATAGGAGTGGGCGAGTTGACACTGGCTTCCTT
GTGTGTAGGTGAGAGCACCGTGTTGTTATATCATGACAGCAATGGTTCGCAAGATAGTATCCTAGCGGTGACGG
TGGGAATATTTGGGGCAACATCTATGGATCAAGTTGAAGAGGTGATACCTGTTGCTCACCCATCAGTAGAAAAA
ATACATATAACAAATCACCGTGGGTTCATAAAAGATTCAATAGCAACCTGGATGGTGCCTGCATTGGTCTCTGA
GAAACAGGAAGAGCAAAAAAATTGTCTGGAGTCGGCTTGTCAAAGAAAATCCTACCCTATGTGCAACCAAACGT
CATGGGAACCCTTCGGAGGAGGACAGTTGCCATCTTATGGGCGGTTGACATTACCTCTAGATCCAAGCACTGAC
CTTCAACTTAACATATCGTTTACATACGGTCCGGTTATACTGAATGGAGACGGTATGGATTATTATGAAAGCCC
ACTGTCGGACTCCGGATGGCTTACCATTCCTCCCAAAAACGGAACAGTCCTTGGATTGATAAACAAAGCAAGTA
GAGGAGACCAGTTCATTGTAATCCCCCATGTGTTGACATTTGCGCCCAGGGAATCAAGTGGGAATTGTTATTTA
CCTATTCAAACATCCCAG (SEQ ID NO:2)

FIG. 2

07091032
GGTGAATTTTACTAACTACTGCGATACAATTGGGATCAGAAAATCTATTGCATCGGCAGCAAATCCCATC
CTCCTGTCAGCACTCTCTGGGGGCAGAGGTGACATATTCCCACCATACAGATGCAGTGGAGCTGCTACCT
CAGTAGGCAGAGTTTTCCCCCTATCAGTGTCATTGTCCATGTCTTTGACCTCAAGAAAATCAGAGATAAT
CAATATGCTAACCGCTATCTCAAACGGAGTGTATGGTAAAACTTATTTACTAGTGCCTGATTATATTGAA
GAGGAGTTCGACACACAAAAGATTCGAGTCTTTGAGATAGGGTTCATCAAACGGTGGCTGAATGACATGC
CATTACTCCAGACAACTAACTATATGGTCCTCCCAGAGAATTCCAAAGCTAAGGTATGTACTATAGCAGT
GGGCGAGTTGACACTGGCTTCCTTGTGTGTAGGTGAGAGCACCGTGTTGTTATATCATGACAGCAATGGT
TCGCAAGATAGTATCCTAGCAGTGACGCTGGGAATATTTGGGGCAACATCTATGGATCAAGTTGAAGAGG
TGATACCTGTTGCTCACCCATCAGTAGAAAAATACATATAACAAATCACCGTGGGTTCATAAAAGATTC
AATAGCAACCTGGATGGTGCCTGCATTGGTCTCTGAGAAACAGGAAGAGCAAAAAAATTGTCTGGAGTCG
GCTTGTCAAAGAAAATCCTACCCTATGTGCAACCCAAACGTCATGGGAACCCTTCGGAGGAGGACAGTTG
CCATCTTATGGGCGG (SEQ ID NO:3)

FIG. 3

07101508
CTAGTAAGATCAGGTGAATTTTACTAATTACTGCTATACAATTGGGATCAGAAAATCTATTGCATCGGCA
GCAAATCCCATCCTCCAGTCAGCACTCTCTGGGGGCAGAGGTGACATATTCCCACCATACAGATGCAGTG
GAGCTGCTACCTCAGTAGGCAGAGTTTTCCCCCTATCAGTGTCATTGTCCATGTCTTTGATCTCAAGAAA
ATCAGAGATAATCAATATGCTAACCGCTATCTCAAACGGAGTGTATGGTAAAACTTATTTACTAGTGCCT
GATTATATTGAAGAGGAGTTCGACACACAAAAGATTCGAGTCTTTGAGATAGGGTTCATCAAACGGTGGC
TGAATGACATGCCATTACTCCAGACAACCAACTATATGGTCCTCCCAGAGAATTCCAAAGCTAAGGTATG
TACTATAGCAGTGGGCGAGTTGACACTGGCTTCCTTGTGTGTAGGTGAGAGCACCGTGTTGTTATATCAT
GACAGCAATGGTTCGCAAGATAATATCCTAGTAGTGACGCTGGGAATATTTGGGGCAACATCTATGGATC
AAGTTGAAGAGGTGATACCTGTTGCTCACCCATCAGTAGAAAAAATACATATAACAAATCACCGTGGGTT
CATAAAAGATTCAATAGCAACCTGGATGGTGCCTGCATTGGTCTCTGAGAAACAGGAAGAGCAAAAAATT
TGTCTGGAGTCGGCTTGTCAAAGAAAATCCTACCCTATGTGCAACCAAACGTCATGGGAACCCTTCGGAG
GAGGACAGTTGCCATCTTATGGGCGGTTGACATTACCTCTAGATNCAAGCACTGACCTTCAACTTAACAT
ATCGTTTACATACGGTCCGGTTATACTGAATGGAGACGGNATGGATTATTATGAAAGCCCACTGTCGG
(SEQ ID NO:4)

FIG. 4

07100609
AACTTGTATCCGGCTCTTGGGTTGCATGAGTTTTCCGGGGAGTTAACAACCATTGAATCCCTTATGATGC
TATATCAACAGATGGGTGAAACAGCACCGTACATGGTTATTCTGGAAAATTCTGTCCAGAACAAATTTAG
TGCAGGATCCTACCCATTGCTCTGGAGTTATGCTATGGGAGTTGGTGTTGAACTTGAAAACTCCATGGGA
GGGTTAAATTTCGGTAGATCCTACTTTGACCCAGCTTATTTCAGGCTCGGGCAAGAAATGGTTAGAAGAT
CGGCCGGTAAGGTAAGCTCTGCACTTGCCGCCGAGCTTGGCATCACCAAGGAAGAGGCTCAGCTAGTGTC
AGAAATAGCATCCAAGACAACAGAGGACCA (SEQ ID NO:5)

FIG. 5

07110098
AAGTGAATTTTACTAGTTACTGTGATACAATTGGGATCAGAAAATCCATTGCATTGGCAGCAAATCCCGT
CCTTTTGTCAGCACTCTCCGGAGGCAGAGGTGACATATTCCCACCATACAGATGCAGTGGAGCTACTACT
TCAGTTGGCAAATCTTTCCCCCTATCAGTATCATTATCCATGTCTTTGATCTCAAGAACATCAGAGATAA
TCAATATGCTGACCTCTATCTCAGACGGAGTGTATGGTAAAACTTATTTGCTAGTGCCTGATTATATTGA
AGGGGAGTTCGACACGCAAAAGATTCGAGTCTTTGAGATAGGGTTCATCAAAGGTGGCTGAATGACATG
CCATTATTCCAGACAACCAACTATATGATCCTCCCGGAGAATTCTAAAACCAAGGTATGTACTATAGCAG
TGGGCGAGTTGACACTGGCTTCCTTGTGTGTAGATGAGAGCACTGTATTATTATATCATGACAGCAATGG
TTCACAAGATGGTATTCTAGTAGTGACGCTGGGAATCTTTGGGGCAACACCTATGGATCAAGTCGAAGAG
GTGATACCTGTCGCTCACCCATCAGTCGAAAAAATACATATAACAAATCACCGTGGTTTCATAAAAGATT
CAGTAGCAACCTGGATGGTGCCTGCATTGGTCTCTGAGAACCTAGAGGAACAAGAAATTGTCTGGAGTC
GGCTTGTCAGAGAAAATCCTACCCTATGTGCAATCAAACATCATGGGAACCCTTTGGAGGAGGACAGTTG
CCATCTTATGGGCGGTTGACGTTACATCTAGATGCAAGCATTGACCGTCAACTTAACATATCATTTACAT
ACGGTCC (SEQ ID NO:6)

FIG. 6

07111080
TCAAGAAAATCAGAGATAATCAATATGCTACCCGCTATCTCAAACGGAGTGTATGGTAAAACTTATTTAC
TAGTGCCTGATTATATGAAGAGGAGTTCGACACACAAAAGATTCGAGTCTTTGAGATAGGGTTCATCAAA
CGGTGGCTGAATGACATGCCATTACTCCAGACAACCAACTATATGGTCCTCCCAGAGAATTCCAAAGCTA
AGGTATGTACTATAGCAGTGGGCGAGTTGACACTGGCTTCCTTGTGTGTAGGTGAGAGCACCGTGTTGTT
ATATCATGACAGCAATGGTTCGCAAGATAGTATCCTAGCAGTGACGCTGGGAATATTTGGGGCAACATCT
ATGGATCAAGTTGAAGAGGTGATACCTGTTGCTCACTCATCAGTAGAAAAAATACATATAACAAATCACC
GTGGGTTCATAAAAGATTCAATAGCAACCTGGATGGTGCCTGCATTGGTCTCTGAGAAACAGGAAGAGCA
AAAAAATTGTCTGGAGTCGGCTTGTCAAAGAAAATCCTACCCTATGTGCAACCAAACGTCATGGGAACCC
TTCGGAGGAGGACAGTTGCCATCTTATGGGCGGTTGACATTACCTCTAGATCCAAGCACTGACCTTCAAC
TTAACATATCGTTTACATACGGTCCGGTTATACTGAATGGAGACGGTATGGATTATTATGAAAGCCCACT
GTCGGACTCCGGATGGCTTACCATTCCTCCCAAAAACGGAACAGTCCTTGGATTGATAAATAAAGCAAGT
AGAGGAGACCAGTTCATTGTAATCCCCCATGTGTTGACATTTGCGCCCAGGGAATCAAGTGGGAATTGTT
ATTTACCTATTCAAACATCCCAGATTATAGA (SEQ ID NO:7)

FIG.7

08010939
GAATTTTACTAATTACTGCGATACAATTGGGATCAGAAAATCTATTGCATCGGCAGCAAATCCCATCCTC
CTGTCAGCACTCTCTGGGGGCAGAGGTGACATATTCCCACCATACAGATGCAGTGGAGCTGCTACCTCAG
TAGGCAGAGTTTTCCCCCTATCAGTGTCATTGTCCATGTCTTTGATCTCAAGAAAATCAGAGATAATCAA
TATGCTAACCGCTATCTCAAACGGAGTGTATGGTAAAACTTATTTACTAGTGCCTGATTATATTGAAGAG
GAGTTCGACACACAAAAGATTCGAGTCTTTGAGATAGGGTTCATCAAACGGTGGCTGAATGACATGCCAT
TACTCCAGACAACCAACTATATGGTCCTCCCAGAGAATTCCAAAGCTAAGGTATGTACTATAGCAGTGGG
CGAGTTGACACTGGCTTCCTTGTGTGTAGGTGAGAGCACCGTGTTGTTATATCATGACAGCAATGGTTCG
CAAGATAATATCCTAGTAGTGACGCTGGGAATATTTGGGGCAACATCTATGGATCAAGTTGAAGAGGTGA
TACCTGTTGCTCACCCATCAGTAGAAAAAATACATATAACAAATCACCGTGGGTTCATAAAAGATTCAAT
AGCAACCTGGATGGTGCCTGCATTGGTCTCTGAGAAACAGGAAGAGCAAAAAAATTGTCTGGAGTCGGCT
TGTCAAAGAAAATCCTACCCTATGTGCAACCAAACGTCATGGGAACCCTTCGGAGGAGGACAGTTGCCAT
CTTATGGGCGGTTGACATTACCTCTAGATCCAAGCACTGACCTTCAACTTAACATATCGTTTACATACGG
TCCGGGTTATACTGAATGGAGACGGTATGGATTATTATGAAAGCCCACTGTCGGACTCCG (SEQ ID NO:8)

FIG.8

08011277A
GCCGGGCTGCATCACCCCCTAGTAAGACAGGTGAATTTTACTTATTACTGCGATACAATTGGGATCAGAA
AATCTATTGCATCGGCAGCAAATCCCATCCTCCTGTCAGCACTCTCTGGGGGCAGAGGTGACATATTCCC
ACCATACAGATGCAGTGGAGCTGCTACCTCAGTAGGCAGAGTTTTCCCCCTATCAGTGTCATTGTCCATG
TCTTTGATCTCAAGAAAATCAGAGATAATCAATATGCTAACCGCTATCTCAAACGGAGTGTATGGTAAAA
CTTATTTACTAGTGCCTGATTATATTGAAGAGGAGTTCGACACACAAAAGATTCGAGTCTTTGAGATAGG
GTTCATCAAACGGTGGCTGAATGACATGCCATTACTCCAGACAACCAACTATATGGTCCTCCCAGAGAAT
TCCAAAGCTAAGGTATGTACTATAGCAGTGGGCGAGTTGACACTGGCTTCCTTGTGTGTAGGTGAGAGCA
CCGTGTTGTTATATCATGACAGCAATGGTTCGCAAGATAATATCCTAGTAGTGACGCTGGGAATATTTGG
GGCAACATCTATGGATCAAGTTGAAGAGGTGATACCTGTTGCTCACCCATCAGTAGAAAAAATACATATA
ACAAATCACCGTGGGTTCATAAAAGATTCAATAGCAACCTGGATGGTGCCTGCATTGGTCTCTGAGAAAC
AGGAAGAGCAAAAAAATTGTCTGGAGTCGGCTTGTCAAAGAAAATCCTACCCTATGTGCAACCAAACGTC
ATGGGAACCCTTCGGAGGAGGACAGTTGCCATCTTATGGGCGGTTGACATTACCTCTAGATCCAAGCACT
GACCCTTCCAACTTAACATATCGTTTACATACCGTCCGGTTATACTTGAATGGAGACGGTATGGATAATT
ATGAAAGCCCACTGTCGGACTCGGATGGCTTACCATTTCCTTCCAAAACGGAACAGTCCTTGGATTGATA
AACAAACCAGTAGGGGAGACCAGTTCATTGTATCCCCATGTGTTGACCATTGCCCCAGGGAATCAAGGG
GAATGTATTTACCTATTCAACCTTCCCAAATAATGGGATAAAGGATGGCCCTCCTGAATCCAAATTACGG
TGTTGCCCTAAAC(SEQ ID NO:9)

FIG. 9

08011277B
TTGGTTAAGGCCATCCTTTTTCCCTAATCTGGGCTGTTTGAATAGGTAAATAACAATTCCCCACTTGATT
CCCTGGGCGCAAATGTCAACACATGGGGATTACAATGAACTGGTCTCCCCTACTTGCTTTGTTTATCAA
TCCAAGGACTGTTCCGTTTTTGGGAGGAATGGTAAGCCATCCGGAGTCCGACAGTGGGCTTTCATAATAA
TCCATACCGTCTCCATTCAGTATAACCGGACCGTATGTAAACGATATGTTAAGTTGAAGGTCAGTGCTTG
GATCTAGAGGTAATGTCAACCGCCCATAAGATGGCAACTGTCCTCCTCCGAAGGGTTCCCATGACGTTTG
GTTGCACATAGGGTAGGATTTTCTTTGACAAGCCGACTCCAGACAATTTTTTGCTCTTCCTGTTTCTCA
GAGACCAATGCAGGCACCATCCAGGTTGCTATTGAATCTTTTATGAACCCACGGTGATTTGTTATATGTA
TTTTTTCTACTGATGGGTGAGCAACAGGTATCACCTCTTCAACTTGATCCATAGATGTTGCCCCAAATAT
TCCCAGCGTCACTACTAGGATATTATCTTGCGAACCATTGCTGTCATGATATAACAACACGGTGCTCTCA
CCTACACACAAGGAAGCCAGTGTCAACTCGCCCACTGCTATAGTACATACCTTAGCTTTGGAATTCTCTG
GGAGGACCATATAGTTGGTTGTCTGGAGTAATGGCATGTCATTCAGCCACCGTTTGATGAACCCTATCTC
AAAGACTCGAATCTTTTGTGTGTCGAACTCCTCTTCAATATAAATCAGGCACCTAGTAAATAAAGTTTA
CCATACACCTCCGTTTGAGATAGCCGGTTAGCATATTGATTATCTCTGATCCTCTTGAGATCAAAGACAT
GGACAATGACACTGATAGGCGGGAAAACTCTGCCTACTGAGGTAGCAGCTCTACTGCTTTTGTTGGGTGG
GAAATATTTAACCCTTTGCCCCCGAAAGTGCTTACAGGAGGATGGGATTTGCTGCCGATCCAATAAATTT
TCTGATCCCAATTGTATCGAAGAACTAATAAATTACCTGGACCTTACTTGGGGGGTGATGAACCAGCGC
(SEQ ID NO:10)

FIG. 10

08011277C
AGATCAAGGTGAATTTTACTAATTACTGCGATACAATTGGGATCAGAAAATCTATTGCATCGGCAGCAAA
TCCCATCCTCCTGTCAGCACTCTCTGGGGGCAGAGGTGACATATTCCCACCATACAGATGCAGTGGAGCT
GCTACCTCAGTAGGCAGAGTTTTCCCCCTATCAGTGTCATTGTCCATGTCTTTGATCTCAAGAAAATCAG
AGATAATCAATATGCTAACCGCTATCTCAAACGGAGTGTATGGTAAAACTTATTTACTAGTGCCTGATTA
TATTGAAGAGGAGTTCGACACACAAAAGATTCGAGTCTTTGAGATAGGGTTCATCAAACGGTGGCTGAAT
GACATGCCATTACTCCAGACAACCAACTATATGGTCCTCCCAGAGAATTCCAAAGCTAAGGTATGTACTA
TAGCAGTGGGCGAGTTGACACTGGCTTCCTTGTGTGTAGGTGAGAGCACCGTGTTGTTATATCATGACAG
CAATGGTTCGCAAGATAATATCCTAGTAGTGACGCTGGGAATATTTGGGGCAACATCTATGGATCAAGTT
GAAGAGGTGATACCTGTTGCTCACCCATCAGTAGAAAAAATACATATAACAAATCACCGTGGGTTCATAA
AAGATTCAATAGCAACCTGGATGGTGCCTGCATTGGTCTCTGAGAAACAGGAAGAGCAAAAAAATTGTCT
GGAGTCGGCTTGTCAAAGAAAATCCTACCCTATGTGCAACCAAACGTCATGGGAACCCTTTCGGAGGAGG
ACAGTTGCCATCTTATGGGCGGTTGAC(SEQ ID NO:11)

FIG. 11

08011277D
CCCCAATTGGCATTGAACCATGTATCCGGCTCTTGGGTTGCATGAGTTTTCCGGGGAGTTAACAACCATT
GAATCCCTTATGATGCTATATCAACAGATGGGTGAAACAGCACCGTACATGGTTATTCTGGAAAATTCTG
TCCAGAACAAATTTAGTGCAGGCTCCTACCCATTGCTCTGGAGTTATGCTATGGGAGTTGGTGTTGAACT
TGAAAACTCCATGGGAGGGTTAAATTTCGGTAGATCCTACTTTGACCCAGCTTATTTCAGGCTCGGGCAA
GAAATGGTTAGAAGATCTGCCGGTAAGGTAAGCTCTGCACTTGCCGCCGAGCTCGGCATCACCAAGGAAG
AGGCTCAGCTAGTGTCAGAAATAGCATCCAAGACAACAGAGGACCTCCCATTTGGCATTGAAACTATGTA
TCCGGCTCTTGGGTTGCATGAGTTTTCCGGGGAGTTAACAACCCTTGAATCTTAATGACCTTTTTCCGCA
GGGAACAAACCCACAATCGCTGAATTCTGTGAAATATGGCTCACCACATTGTGGCAGCTCGACACCGACT
TTAACCTTACCTATGGAATTTGGCGTTGAAACTGTAAATCCCTCTTCGGGTTACCACCTCTTTTGATCAC
TTTAACCGTTATTTACGCCGGCAGCCACGTTAGAACATATCCGCCTTCGCAAGTTTTCCTGCCTCCTCCT
TCCACCCAATTAGAGGGCCCCCCTCCTTTGTTATGAACCCCCTTA(SEQ ID NO: 12)

FIG. 12

08011671
CCTGGGCGCCTTACCCCCCCCTAGTAAGCTCAGGTGAATTTTACTAACTACTGCGATACCCTTGGGATCA
GAAAATCTATTGCATCGGCAGCAAATCCCATCCTCCTGTCAGCACTCTCTGGGGGCAGAGGTGACATATT
CCCACCATACCGATGCAGTGGAGCTGCTACCTCAGTAGGCAGAGTTTTCCCCCTGTCAGTGTCATTGTCC
ATGTCTTTGATCTCAAGAAAATCAGAGATAATCAATATGCTAACCGCTATCTCAAACGGAGTGTATGGTA
AAACTTATTTACTAGTGCCTGATTATATTGAAGAGGAGTTCGACACACAAAAGATTCGAGTCTTTGAGAT
AGGGTTCATCAAACGGTGGCTGAATGACATGCCATTACTCCAGACAACCAACTATATGGTCCTCCCAGAG
AATTCCAAAGCTAAGGTATGTACTATAGCAGTGGGCGAGTTGACACTGGCTTCCTTGTGTGTAGGTGAGA
GCACCGTGTCGTTATATCATGACAGCAATGGTTCGCAAGATAGTATCCTAGCAGTGACGCTGGGAATATT
TGGGGCAACATCTATGGATCAAGTTGAAGAGGCGATACCTGTTGCTCACCCATCAGTAGAAAAAATACAT
ATAACAAATCACCGTGGGTTCATAAAAGATTCAATAGCAACCTGGATGGTGCCTGCATTGGTCTCTGAGA
AACAGGAAGAGCAAAACAATTGTCTGGAGTCGGCTTGTCAAAGAAAATCCTACCCTATGTGCAACCAAAC
GTCATGGGAACCCTTCGGAGGAGGACAGTTGCCATCTTATGGGCGGTTGACATTACCTTAGATCCAAGCA
CTGACCTTCAACTCAACATATCGCTTACATACCGTCCGGCTATACTGAATGGGAGACGGTATGGATTTTA
TGACAAGCCCCCTGTCGGACTCCCGGATGGCTTACCACCCCCTCCCAAAACCGGAACAGCTCCTTCGAT
TGATAAACCAAACCAGTACGAGGAGACTCAGTTTCATTGTTATTCCCCTACGTGTTGACATTTCCGCCCC
AGGCCATCCATGTCGGATTGCTCTTTACCCAATAACCCACCCCACATCATGGATACAGCTCTCCTTACTG
ACTCCACACTACCGCTGTTGCCTACCCTCCCGCTCTCCCTTCCCCTA(SEQ ID NO:13)

FIG. 13

08021509
GTGAATTTTACTAATTACTGCGATACTATGGGGATCAGAAAATCTATTGCATCGGCAGCAAATCCCATCC
TTTTATCAGCACTCTCCGGAGGTAGAGGTGACATATTCCCACCATACAGATGCAATGGAGCTACTATTTC
AGTAGGCAAGATTTTCCCCCNATCAGTATCATTATCTATGTCTTTGATCTCAAGAACATCAGAGATAATC
AATATGCTAACCGCTATCTCAGACGGAGTGTATGG(SEQ ID NO:14)

CAAGGTGAATTTTACTAATTACTGCGATACAATTGGGATCAGAAAATCTATTGCATCGGCAGCAAATCCC
ATCCTCCTGTCAGCACTCTCTGGGGGCAGAGGTGACATATTCCCACCATACAGATGCAGTGGAGCTGCTA
CCTCAGTAGGCAGAGTTTTCCCCCTATCAGTGACATTGTCCATGTCTTTGATCTCAAGAAAATCAGAGAT
AATCAATATGCTAACCGCTATCTCAAACGGAGTGTATGGTAAGACTTATTTACTAGTGCCTGATTATATT
GAAGAGGAGTTCGACACACAAAAGATTCGAGTCTTTGAGATAGGGTTCATCAAACGGTGGCTGAATGACA
TGCCATTACTCCAGACAACCAACTATATGGTCCTCCCAGAGAATTCCAAAGCTAAGGTATGTACTATAGC
AGTGGGCGAGTTGACACTGGCTTCCTTGTGTGTAGGTGAGAGCACCGTGTTGTTATATCATGACAGCAAT
GGTTCGCAAGATAATATCCTAGTAGTGACGCTGGGAATATTTGGGGCAACATCTATGGATCAAGTTGAAG
AGGTGATACCTGTTGCTCACCCATCAGTAGAAAAAATACATATAACAAATCACCGTGGGTTCATAAAAGA
TTCAATAGCAACCTGGATGGTGCCTGCATTGGTCTCTGAGAAACAGGAAGAGCAAAAAAATTGTCTGGAG
TCGGCTTGTCAAAGAAAATCCTACCCTATGTGCAACCAAACGTCATGGGAACCCTTCGGAGGANGGACAG
TTGCCATCTTATGGGCGGTTGACATTACCTCTAGATCCAAGCACTGACCTTCAACTTAACATATC
(SEQ ID NO:15)

FIG. 15

08030776
TCCTGTTTGCCTTTCCCCCCCCTAGTAAGATCAGGTGAATTTTACTAACAACTGCGATACAATTGGGATC
AGAAAATCTATTGCATCGGCAGCAAATCCCATCCTCCTGTCAGCACTCTCTGGGGGCAGAGGTGACATAT
TCCCACCATACAGATGCAGTGGAGCTGCTACCTCAGTAGGCAGAGTTTTCCCCCTATCAGTGTCATTGTC
CATGTCTTTGATCTCAAGAAAATCAGAGATAATCAATATGCTAACCGCTATCTCAAACGGAGTGTATGGT
AAAACTTATTTACTAGTGCCTGATTATATTGAAGAGGAGTTCGACACACAAAAGATTCGAGTCTTTGAGA
TAGGGTTCATCAAACGGTGGCTGAATGACATGCCATTACTCCAGACAACCAACTATATGGTCCTCCCAGA
GAATTCCAAAGCTAAGGTATGTACTATAGCAGTGGGCGAGTTGACACTGGCTTCCTTGTGTGTAGGTGAG
AGCACCGTGTTGTTATATCATGACAGCAATGGTTCGCAAGATAGTATCCTAGCAGTGACGCTGGGAATAT
TTGGGGCAACAACTATGGATCAAGTTGAAGAGGTGATACCTGTTGCTCACCCATCAGTAGAAAAAATACA
TATAACAAATCACCGTGGGTTCATAAAAGATTCAATAGCAACCTGGATGGTGCCTGCATTGGTCTCTGAG
AAACAGGAAGAGCAAAAAAATTGTCTGGAGTCGGCTTGTCAAAGAAAATCCTACCCTATGTGCAACCAAA
CGTTATGGGAACCCTTCGGAGGAGGACAGTTGCCATCTTATGGGCGGTTGACATTACCTCTAGATCCAAG
CACTGACCTTCAACTTAACATATCGTTTACATACGGTCCGGTTATCCTGAATGGAGACGGTATGGATTAT
TATGAAAGCCCACTGTCGGACTCCCGATGGCTTACCATTCCTCCAAAACGGAACAGTCCTTGGATTGATA
AACAAACAAGTAGAGGAGACCAGTTCATTGAATCCCCATGTGTTGACTTTTCGCCCAGGGAATCAAGTGG
AATTGTATTTACTATCAACTTCCAGATTATGGATAAGATGTCCTTCTGATTCCAATACGGTGTGCCTTA
(SEQ ID NO:16)

FIG. 16

08030777
TCGTGGTGCTTAACCCCCCCTAGTAAGATCAGGTGAATTTTACTAATTACTGCGATACTATTGGGATCAG
AAAATCTATTGCATCGGCAGCAAATCCCATCCTTTTATCAGCACTCTCCGGAGGTAGAGGTGACATATTC
CCACCATACAGATGCAATGGAGCTACTATTTCAGTAGGCAAGATTTTCCCCCTATCAGTATCATTATCTA
TGTCTTTGATCTCAAGAACATCAGAGATAATCAATATGCTAACCGCTATCTCAGACGGAGTGTATGGTAA
AACTTATTTACTAATGCCTGATTATATTGAAGGGGAGTTCGACACGCAAAAGATTCGAGTCTTTGAGATA
GGGTTCATCAAACGGTGGCTGAATGACATGCCATTACTCCAGACAACCAACTATATGGTCCTCCCAGAGA
ATTCCAAAGCCAAGGTATGTACTATAGCAGTGGGCGAGTTGACACTGGCTTCTTTGTGTGTAGATGAGAG
CACCGTATTGTTATATCATGACAGCAATGGTTCACAAGATGGTGTTCTAGTAGTGACGCTGGGAATATTC
GGGGCAACATCTATGGATCAAGTTGAAGAGGTGATACCTGTCGCTGACCCATTAGCAGAAAAAATACATA
TAACAAATCACCGTGGGATCATAAAAGACTCAATAGCAACCTGGATGGTGCCTGCATTAGTTTCTGAGAA
ACAAGAGGAACAAACAAATTGTCTGGAGTCAGCTTGTCAAAGAAAATCCTACCCTATGTGCAATCAAACG
TCATGGGAACCCTTTGGAGGAGGACAGTTGCCATCTTATGGGCGGCTGACATTACCTCTACATCCAAGCA
TTGACCTCCACTTAACATATCATTTACATACGGTCCGACTATACTGAATGGAGACGGATGGCTATTATGA
GAGCCCCCTGCGGACTCCGGATGGCTTACCTTTCCCTCCAGCACGGCACAGCCTGGATTGATAAACAAAG
AGTAGAGGACGACCAGTTATTGTCATTCCCCTGTGTTGACATTTCGCCCCCGGCATCCACCCGAAATTGC
TATTACCCTATCCCACATTCCCCTTCGCGCTCAAGATCCCCCTCCTGCTCCCCACCACGGCGCGCTCCCT
ATCTCC(SEQ ID NO: 17)

FIG. 17

08031346
CCTAGTAGATCAAGGTGAATTTTACTAATTACTGCGATACAATTGGGATCAGAAAATCTATTGCATCGGC
AGCAAATCCAATCCTCCTGTCAGCACTCTCTGGGGGCAGAGGTGACATATTCCCACCATACAGATGCAGT
GGAGCTGCTACCTCAGTAGGCAGAGTTTTCCCCCTATCAGTGTCATTGTCCATGTCTTTGATCTCAAGAA
AATCAGAGATAATCAATATGCTAACCGCTATCTCAAACGGAGTGTATGGTAAAACTTATTTACTAGTGCC
TGATTATATTGAAGAGGAGTTCGACACACAAAAGATTCGAGTCTTTGAGATAGGGTTCATCAAACGGTGG
CTGAATGACATGCCATTACTCCAGACAACCAACTATATGGTCCTCCCAGAGAATTCCAAAGCTAAGGTAT
GTACTATAGCAGTGGGCGAGTTGACACTGGCTTCCTTGTGTGTAGGTGAGAGCACCGTGTTGTTATATCA
TGACAGCAATGGTTCGCAAGATAGTATCCTAGCAGTGACGCTGGGAATATTTGGGGCAACATCTATGGAT
CAAGTTGAAGAGGTGATACCTGTTGCTCACCCATCAGTAGAAAAAATACATATAACAAATCAC
(SEQ ID NO:18)

FIG. 18

08040383
GTTTGATAGGTAAATAACAGTTTCCACTTGATTCCCTGGGTGCAAATGACAACACATGAGGGACCACAGT
GAACTGGTCTCCTCTACTTGCTTTGTTTATCAATCCAAGAATTGTTCCATTCTTAGGAGGAATGGTAAGC
CATCCGGATTCCAAAAGTGGGCTTTCATAATAATCCATACCATCTCCATTCAGTATAACCGGACCGTATG
TAAATGATATGTTAAGTTTACGGTCAATGCTTGCATCTAGATGTAACGTCAACCGCCCATAAGATGGCAA
CTGTCCTCCTCCAAAGGGTTCCCATGATGTTTGATTGCACATGGGGTAGGATTTTCTCTGACAAGCCGAC
TCCAGACAATTTTCTTGTTCCTCTAGGTTCTCAGAGACCAATGCAGGCACCATCCAGGTTGCTACTGAAT
CTTTTATGAAACCACGGTGATTTGTTATATGTATTTTTCGACTGATGGGTGAGCGACAGGTATCACCTC
TTCGACTTGATCCATAGGTGTTGCCCCAAAGATTCCCAGCGTCACTACTAGAATACCATCTTGTGAACCA
TTGCTGTCATGATATAATAATACAGTGCTCTCATCTACACACAAGGAAGCCAGTGTCAACTCGCCCACTG
CTATAGTACATACCTTGGTTTTAGAATTCTCCGGGAGGATCATATAGTTGGTTGTCTGGAATAATGGCAT
GTCATTCAGCCACCTTTTGATGAACCCTATCTCAAAGACTCGAATCTTTTGCGTGTCGAACTCCCCTTCA
ATATAATCAGGCACTAGCAAATAAGTTTTACCATACACTCCGTCTGAGATAGAGGTCAGCATATTGATTA
TCTCTGATGTTCTTGAGATCAAAGAC(SEQ ID NO:19)

FIG. 19

08050180A
AATGCTTCCTTTACCCACCCTAGTAAGATCAAGTAAATTTTACGGTAAATAAATAGCGATACAATTGGGA
TCAGAAAATCTATTGCATCGGCAGCAAATCCTATCCTTTTATCAGCACTCTCCGGAGGTAGAGGTGACAT
ATTCCCACCATACAGGTGCAGTGGAGCTACTACTTCAGTAGGCAGAGTCTTCCCCCTATCAGTATCATTG
TCCATGTCTTTGGTCTCAAGAACATCTGAAATAATCAATATGCTAACCGCTATCTCAGACGGTGTGTATG
GTAAAACTTATTTGCTAGTTCCTGATTATCTTGAAGGGGAGTTCGACACGCAAAAGATTCGAGTCTTTGA
GATAGGGTTCATCAAACGGTGGCTGAACAACATGCCATTACTCCAGACAACCAACTATATGGTCCTCCCG
GAGGATTCCAAAGCCAAGGTATGTACTATAGCGGTGGGCGAGTTGACACTGGCTTCCTTGTGTGTAGATG
AGAGCACCGTATTGTTATATCATGACAGCAGTGGTTCACAAGATGGTATTCTAGTGGTGACGCTGGGAAT
ATTTGGGGCAACACCTATGGATCAAGTTGAAGAGGTGATACCTGTTGCTCACCCATCAGTAGAAAAAATA
CATATAGCAAACCACCGTGGGTTCATCAAAGATTCAATAGCAACCTGGATGGTGCCTGCATTGGTCTCTG
AGAAACAAGAGGAACAAAAAAATTGTCTGGAGTCGGCTTGTCAAAGAAAATCCTACCCTATGTGCAACCA
AACGTCATGGGAACCCTTTGGAGGAGGACAGTTGCCATCTTATGGGCGGTTGACATTACCTCTAGATCAA
AGCATTGACCTCCAGCTTAACATCTCATTTACATATGGTCCGGTTATACTGAATGGAGACGGTATGGATT
ATTATGAAAGTCCGCTTTTGAACTCCGGATGGCTTACCATTCCTCCCAAGAACGGAACAGTCCTTGGATT
GATAAACAAAGCAAGTAGAGGAGACCAGTTCACTGTATCCCCATGTGTGACATTTGCGCCCAGGGAATCA
AGTGGAATTGTATTTACCTATTCAAACATCCCAGATATGGATAAAGATGTCCTTACTGAATCCAAATTAG
TGGTGTTGCCTAAC(SEQ ID NO:20)

FIG. 20

08060351
ACCGGGGTGCTTACCCCCCCTAGTAAGATCAAGTGAATTTTACGAAAAACTGCGATCCAATTGGGATCAG
GAAATCTATTGCAACGGCAGCAAATCCTATCCTTTTATCAGCACCCTCCGGAGGTAGAGGTGACATATTC
CCATCATACAGATGCAGTGGAGCTACTACTTCAGTAGGCAGAGTCTTCCCCCTATCAGTATCATTGTCCA
TGTCTTTGATCTCAAGAACATCTGAAATAATCAATATGCTAACCGCTATCTCAGACGGAGTGTATGGTAA
AACTTATCTGCTAGTTCCTGATTATCTTGAAGGGGAGTTCGACACGCAAAAGATTCGAGTCTTTGAGATA
GGGTTCATCAAACGGTGGCTGAACAACATGCCATTACTCCAGACAACCAACTATATGGTCCTCCCAGAGG
ATTCCAAAGCCAAGGTATGTACTATAGCAGTGGGCGAGTTGACACTGGCTTCCTTGTGTGTAGATGAGAG
CACCATATTGTTATATCATGACAGCAATGGTTCACAAGATGGTATTCTAGTGGTGACGCTGGGAATATTT
GGGGCAACACCTATGGATCAAGTTGAAGAGGTGATACCTGTTGCTCACCCATCAGTAGAAAAAATACATA
TAGCAAACCATCGTGGGTTTATCAAAGATTCAATAGCAACCTGGATGGTGCCTGCATTGGTCTCTGAGAA
ACAAGAGGAACAAAAAAATTGTCTGGAGTCGGCTTGTCAAAGAAAATCCTACCCTATGTGCAACCAAACG
TCATGGGAACCCTTTGGAGGAGGACAGTTGCCATCTTATGGGCGGTTGACATTACCTCTAGATCCAAGCA
TTGACCTTCAGCTTACATCTCATTTACATACGGCCCGTTATACTGAATGGAGACGGTATGGATACTATGA
AAGCCCACTTTTAGACTCCGGATGGCTTACCATTCCTCCAAGAACGGAACAGTCCTTGGATTGATAAACA
AAGCAAGTAGAGGAGACCAGTTCACTGTATCCCCATGTGTTGACATTTGCGCCAGGAATCAGTGGAAATT
GTTATTTACCTATTCAAACTTCCCAATTATGGATAAGAGTCCTACTGGATCCAAATTATGGTGTTTCCCT
AACC(SEQ ID NO:21)

FIG. 21

08060352
CATTGGTGCATTAACCCACCTAGTAAGACAAGTGAATTTTACTAATATACTGCGATACAATTGGGATCAG
GAAATCTATTGCATCGGCAGCAAATCCTATCCTTTTATCAGCACCCTCCGGAGGTAGAGGTGACATATTC
CCATCATACAGATGCAGTGGAGCTACTACTTCAGTAGGCAGAGTCTTCCCCCTATCAGTATCATTGTCCA
TGTCTTTGATCTCAAGAACATCTGAAATAATCAATATGCTAACCGCTATCTCAGACGGAGTGTATGGTAA
AACTTATCTGCTAGTTCCTGATTATCTTGAAGGGGAGTTCGACACGCAAAAGATTCGAGTCTTTGAGATA
GGGTTCATCAAACGGTGGCTGAACAACATGCCATTACTCCAGACAACCAACTATATGGTCCTCCCAGAGG
ATTCCAAAGCCAAGGTATGTACTATAGCAGTGGGCGAGTTGACACTGGCTTCCTTGTGTGTAGATGAGAG
CACCATATTGTTATATCATGACAGCAATGGTTCACAAGATGGTATTCTAGTGGTGACGCTGGGAATATTT
GGGGCAACACCTATGGATCAAGTTGAAGAGGTGATACCTGTTGCTCACCCATCAGTAGAAAAAATACATA
TAGCAAACCATCGTGGGTTTATCAAAGATTCAATAGCAACCTGGATGGTGCCTGCATTGGTCTCTGAGAA
ACAAGAGGAACAAAAAAATTGTCTGGAGTCGGCTTGTCAAAGAAAATCCTACCCTATGTGCAACCAAACG
TCATGGGAACCCTTTGGAGGAGGACAGTTGCCATCTTATGGGCGGTTGACATTACCTCTAGATCCAAGCA
TTGACCTTCAGCTTAACATCTCATTTACATACGGTCCGGTTATACTGAATGGAGACGGTATGGATTACTA
TGAAAGCCCACTTTTAGACTCCGGATGGCTTACCATTCCTCCCAAGAACGGAACAGTCCTTGGATTGATA
AACAAAGCAAGTAGAGGAGACCAGTTCACTGTAATCCCCCATGTGTTGACATTTGCGCCCAGGGAATCAA
GTGGAAATTGTTATTTACCTATTCCAAACATCCCAGATTATGGATAAAGGATGTCCTTACTGAAGTTCTA
AATTAGTGGGGGTTTGCCCTAAGAC(SEQ ID NO:22)

FIG. 22

08080696
GCCTCCCAGGGGCACCTTCCCCCCCCAGTAGCTCAGGTGAATCTCACTTAAAACTGCGCCCCCCTTGGGA
TCTTACAATCTATTGCATCGGCAGCAAATCCCCTCCTTTTATCAGCACTCTCCCGAGGTAGAGGTGACAT
ATTCCCCACCATACCGATGCAATGGAGCTACTATTTCACTAGGCAAGATTTCCCCCCTATCAGTATCATTA
TCTATGTCTTTGATCTCACGAACATCAGAGATAATCAATATGCTAACCGCTATCTCATACGGAGTGTATG
GTAAAACTTATTTACTAATGCCCGACTATATTGAAGGGGAG(SEQ ID NO:23)

FIG. 23

08080941
TTGATTTCGACTCCCCGATTTTCCACTGTGCATTAACCACCTAGTAAGATCAAGGTGAATTTTACTGACT
CTGGAACAAATGGGATCAAGAAATTTATTGCATGGCAGCAAATCCCATCTCCTGTCAGCACTCTATGGGG
GCAGAGGTGACATATTCCCACCATACAAGATGCAGTGGAGCTGCTACCTCAGTAGGCAGAGTTTTCCCCC
TATCAGTGTCATTGGCCATGTCTTTGACCTCAAGAAAATCAGAGGATAATCAATATGCTAACCGCTATCT
CAAAACGGAGTGTATGGTAAAACTTATTTACTAGTGCCTGATTATATTGAAGAGGAGTTCGACACACAAA
AAGATTCGAGTCTTTGAGATAGGGTTCATCAAACGGTGGCTGAATAACATGCCATTACTCCAGACAACTA
ACTATATGGTCCTCCCAGAGAATTCCAAAGCTAAGGTATGTACTATAGCAGTGGGCGAGTTGACACTGGC
TTCCTTGTGTGTAGGTGAGAGCACCGTGTTGTTATATCATGACAGCAATGGTTCGCAAGATAGTATCCTA
GCAGTGACGCTGGGAATATTTGGGGCAACATCTATGGATCAAGTTGAAGAGGTGATACCTGTTGCTCACC
CATCAGTAGAAAAAATACATATAACAAATCACCGTGGGTTCATAAAAGATTCAATAGCAACCTGGATGGT
GCCTGCATTGGTCTCTGAGAAACAGGAAGAGCAAAAAAATTGTCTGGAGTCGGCTTGTCAAAGAAAATCC
TACCCTATGTGCAACCAAACGTCATGGGAACCCTTCGGAGGAGGACAGTTGCCATCTTATGGCGGTTGA
CATTACCTCTAGATCCAAGCACTGACCTTCAACTTAACATATCGTTTACGTACGGTCCGGTTATACTGAA
TGGAGACGGTATGGATTATTATGAAAGCCCACTGTCGGACTCCGGATGGCTTACCATTCCTCCCAAAAAC
GGAACAGTCCTTGGATTGATAAACAAAGCAAGTAGAGGAGATCAGTTCATTGTAATCCCCCATGTGTTGA
CATTTGCGCCCAGAGAATCAAGTGGGAATTGTTATTTACCTATTCAAACATCCCATATTAGGAAAAGGG
AGGCCTACCCGGGGA(SEQ ID NO:24)

FIG. 24

08081112
TATGGTTCATTACCCCCCGGCGTAAGTGAATTTGAATCGTAGTAATTGCTGTGATAAAATTGGGATTGGA
AATGTATTGCATTGTTATGAAATTCTACCTTTTCAGCACTTGCCTCCGTTGGTTGAGGGGACTTATTCCC
ATCATACATATGCAGTGGAGCTACTACCTCATCCGGCAGAGTTATATTTGATCATCATTATTGCACATGT
TTGTGACCTAAAAAACATCTGGCATATGCAATCTGCTAACCGCGATCTCATGTGGAGTGTATGGCAAAAC
TTATCTGCTACTTCCTGATTTTCTTGAAGGGGAGTCCGACACTCTGCCGATGTCCGACAAGCTGATCGGG
TTCATCAAACTCTGGCTGAACAACATGTTGCGCGTCTGACAACCTCCGATTTGGCCTGCCCAGAGGATTT
TACAGCCAAGGTATGTACCATATCCCAGGGGAACTTCACACTGCCTTCCTTGTGTGTTAGCCAGAGCCCC
ATATTGTCCCATAATGATATGAATGTCCTACAAGAGGTCATTTTCCATGTGACCCCGCGTTCATTTGTGG
CAATGGCGGTGGTTCAATTGGAACAGGGTATATCTGACCCTATCTTTCACTAGAGAAATTACATATGACA
AACCATCATGGCTTGATCAAAGAATAACTTCCTTTCTGGCTGACGCTTGACTTGCCCTTATATATACCAT
ATTTTCTTAATAAATCGCGGTCAATTGCCTGTGGAGCCAAATTTTACCACTCTTCCAACCTTATGTTACG
GGCTTTCCTTGCCGGAGGACCGTTGC(SEQ ID NO:25)

FIG. 25

08120827
GCGATTTTGCCCTGTGCATTAACCCACCTAGTAAGATCAAGGTAAATTTTACTAAATTCTGCGAAACATG
TGGATCAGAAAATCTATGGCATCGGCAGCAATCCCATCCTCCTGCAGCCCTCTTGGGGCAGAGGTGACAT
ATTCCCACCATACAGATGCAGTGAGGCTGCTACCTCAGTAGGCCAGAGTTTTCCCCTATCAGGGTCATTG
TGCATGTCTTTGACCTCAAGAAAGTCAGAGATAATCAAATATGCTAACCCGCTATCTCAAACGGAGTGTA
TGGGAAAAACTTATTTACTAGTGCCTGGATTATATTGAAGAGGAGTTCGACACACAAAAGATTCGAGTCT
TTGAGATAGGGTTCATCAAACGGTGGCTGAATAACATGCCATTACTCCAGACAACTAACTATATGGTCCT
CCCAGAGAATTCCAAAGCTAAGGTATGTACTATAGCAGTGGGCGAGTTGACACTGGCTTCCTTGTGTGTA
GGTGAGAGCACCGTGTTGTTATATCATGACAGCAATGGTTCGCAAGATAGTATCCTAGCAGTGACGCTGG
GAATATTTGGGGCAACATCTATGGATCAAGTTGAAGAGGTGATACCTGTTGCTCACCCATCAGTAGAAAA
AATACATATAACAAATCACCGTGGGTTCATAAAAGATTCAATAGCAACCTGGATGGTGCCTGCATTGGTC
TCTGAGAAACAGGAAGAGCAAAAAAATTGTCTGGAGTCGGCTTGTCAAAGAAAATCCTACCCTATGTGCA
ACCAAACGTCATGGGAACCCTTCGGAGGAGGACAGTTGCCATCTTATGGGCGGTTGACATTACCTCTAGA
TCCAAGCACTGACCTTCAACTTAACATATCGTTTACATACGGTCCGGTTATACTGAATGGAGACGGTATG
GATTATTATGAAAGCCCACTGTCGGGACTCCGGATGGCTTACCATTCCTCCCAAAAACGGAACAGTCCTTG
GATTGATAAACAAAGCAAGTAGAGGAGATCAGTTCATTGTAATCCCCCATGTGTTAACATTTGCGCCCAG
AGAATCAAGTGGGGATTGTTATTTTCCTATTCAAACATGCCCATATTATGATAAAGGATGGCCTTAACC
CG(SEQ ID NO:26)

FIG. 26

08120857
AGTTCGACGCACAAAAGATTCGAGTGTTGAGATAGGGTTGATCGGACGAGGAGGTGAAGGACATGCCATT
ACTCCAGACAGCTAACTATATGGTCCGCCCAGAGAATTCCAAAGCTAAGGTATGTACTATAGCAGTGGGC
GAGGTGGCACTGGCTTCCTTGTGTGTAGGGGAGAGCGCCGTGTTGTTATATCATGGCAGCAATGGTTCGC
AAGATAGTATCGTAGCAGTGACGCTGGGAATATTTGGGGCAACATCTATGGATCAAGTTGAAGAGGTGAT
ACCTGTTGCTCACCCATCAGTAGAGAAATACATATAGCAAATCACCGTGGGTTCATAAAAGATTCAATA
GCAACCTGGATGGTGCCTGCATTGGTCTCTGAGAAACAGGAAGAGCAAAAAAATTGTCTGGAGTCGGCTT
GTCAAAGAAAATCCTACCGTATGTGCAGCCAAACGGCATGGGAACCCTTCGGAGGAGGACAGTTGCCATC
TTATGGGCGGTTGACATTACCTCTAGATCCAAGCGCTGCCTTCAACTTAACATATCGTTTACATACGGTC
CGGTTATACTGAATGGAGACGGTATGGATTATTATGAAAGCCCACTGTCGGGCTCCGGATGGCTTGCCAT
TCCTCCCAAAAACGGAACAGTCCTTGGATTGATAAACAAAGCAAGTAGAGGAGATCAGTTCATTGTAATC
CCCCATGTGTGGACATTTGCGCCCAGAGAATCAAGTGGGGATTGTTTTTTAAACTATGCAAACGGCGCA
TATGAGGGGGGAGGGGGGCGGGAGGCT(SEQ ID NO:27)

FIG. 27

09011024
CAGTGAGAGCAAAAATGTAGGAAAGGGCAGGAATTCCATGCTCAAGGAGCGGATGTGGGGAGAGGTTGCG
AGTCCCGCCAGCAGTGCAGGAAGGGGTACTCAGTAGCGGGGTTTCCCCCTAGGAGGGGGATTGTCCAGTC
TTTGATATCAGAAAAGAAGGATATCAATATGCTAACCGCTATCGCCAAAGGAGGGTATGGTAAGAGCTTA
TTGGGAGTGCCTGATTAGAGGGAGGGAAGTTCTACAGGAGAGAGATTGGAGTGGTGAGATGGGGGTTCGT
CAAGCGGTGGATGAATGACATACCATTACTCCAGACAACCAAGTATAGGGGCCTCCCAGAGAATGCCAAA
GCTAAGGTATGTACTATAGCAGTGGGCGAGTTACGCTGGCTTCCTTGTGTGTAGGTGAGAGCGCCGTGTT
GTTATATCATGACAGCAATGGTTCGCAAGATAGTATCCTAGCTGTGACGCTGGGAATATTTGGGGCAGCA
TCTATGGATCAAGTTGAAGAGGTGATGCCTGTTGCTCACCCATCAGTAGAAAAAATACATATAACAAATC
GCCGTGGGTTCATAAAAGATTCAATAGCAGCATGGATGGTGCCTGCATTGGTCTCTGAGAAGCAGGAAGA
GCAAAAAATTGTCAGGAGTCGGGTTGTCAAAGAAAATCCTACCCGATGTGCAACCAAACGTCATGGGAA
CCCTTCGGAGGAGGACAGGTGCCATCTTATGGGCGGTTGGCATTACCTCTAGAGCCAAGCACTGGCCTTC
AACTTGACATATCGTTTACATACGGGCCGGTTATACTGAATGGAGACGGTATGGATTATTATGAAAGCCC
ACTGTCGGACGCCGGATGGCTTACCATTCCTCCCAAAAACGGAACAGTCCGTGGATTGATAAACAAAGCA
AGTAGAGGAGGCCAGTTCATTGTAATCCCCCATGTGTTGACATTTGCGCCCAGGGAATCAAGTGGGAATT
GCTATTTTCCTATTCAGAACACCCCAGATTAGGATAGAAGGAGGGGCCTGGGCCG(SEQ ID NO:28)

FIG. 28

09020504-3
CTTGTGGGCTTAAACCACCTAGTAATACAAAGTGAATTTTACTAATTACTGCGATACAATTGGGATCAAA
AAATCTATTGCATCGGCAGCAAATCCTATCCTTTTATCAGCACTCTCCGGAGGCAGAGGTGACATATTCC
CACCATACAGATGCAGTGGAGCTACTACTTCAGTAGGCAGAGTCTTCCCCTTATCAGTATCATTGTCCAT
GTCTTTGATCTCAAGAACATCTGAAATAATCAATATGCTAACCGCTATCTCAGACGGAGTGTATGGTAAA
ACTTATTTGCTAGTTCCTGATTATCTTGAAGGGGAGTTCGACACGCCGAAGATTCGAGTCTTTGAGATAG
GGTTCATCAAACGGTGGCTGAACAACATGCCATTAATCCAGACAACCAACTATATGGTCCTCCCGGAGGA
TTCCAAAGCTAAGGTATGTACTATAGCAGTGGGCGAGTTGACACTGGCTTCCTTATGTGTAGATGAGAGC
ACCGTATTGTTATATCATGACAGCAATGGTTCACAAGATGGTATTCTAGTGGTGACGCTGGGAATATTTG
GGGCAACACCTATGGATCGAGTTGAAGAGGTGATACCTGTTGCTCACCCGTCAGTAGAAAAAATACATAT
GGCAAACCACCGTGGGTTCATCAAAGATTCAATAGCAACCTGGATGGTGCCTGCATTGGTCTCTGAGAAA
CAAGAGGAACAAAAAAATTGTCTGGAGTCGGCTTGTCAAAGAAAATCCCTACCCTATGTGCAACCAAACG
TCATGGGAAACCCTTTGGAGGAGGACAGTTGCCATCTTATGGGCGGTTGACATTACCTCTAGATCCAAGC
ATTGACCTTCACCTTAACATCTCATTTACATACGGCCCAGTTATACTGAATGGGGACGGTATGGATTATT
ATGAAAGCCCACTTTTGGACTCCGGATGGCTTACCATTCCTCCCAAGAACGGAACAGTCCTTGGATTGAT
AAACAGAGCAGTAGAGGAGAACAGTTCACTGTAATCCCCATGTGTTGACTTGCGCAAGGGGATCAAGTGG
AAATTGTATTTACCTATTCAAACATCTTAAATTATGGATAAAGATGCCCTCACCGAGCCCAAATTAGTGG
TGTTGCCTCAT(SEQ ID NO:29)

FIG. 29

09041289
CTCCCTTTCGGCTTGAACATGTATCCGGCTCTTGGGTTGCATGAGTTTTCCGGGGAGTTAACAACCATTG
AATCCCTTATGATGCTATATCAACAGATGGGTGAAACAGCACCGTACATGGTTATTCTGGAAAATTCTGT
CCAGAACAAATTTAGTGCAGGATCCTACCCATTGCTCTGGAGTTATGCTATGGGAGTTGGTGTTGAACTT
GAAAACTCTATGGGAGGGTTAAATTTCGGTAGATCCTACTTTGACCCAGCTTATTTCAGGCTCGGGCAAG
AAATGGTTAGAAGATCGGCCGGTAAGGTAAGCTCTGCACTTGCCGCCGAGCTTGGCATCACCAAGGAAGA
GGCTCAGCTAGTGTCAGAAATAGCATCCAAGACAACAGAGGACCCGCATTTGGCATTGAAACTATGT TC
CGGCTCTTGGGTTGCATGAGTTTTCCGGGGAGTTAACAACCATTGAATCCCTTGTGATGCTTTACCACCA
AATGGGTGAAGGACCCCCCATGGTTATTCTTGGAAAATTTGTCCGACAAAATTAGTGCAGGATCTACCAT
TGCTCTGGAGTTATGCTATGGGAGTTGGTGGTGAACTTGAAAACCCCATGGGGGGGTTAAATTTCGGCAG
ATTCTTCTTTGACAGTTAATTTTAGGCTCGGCCAGAAAATGGTTAGAAAACTCGGCCGGTTAGGGG  AG
CTTTGTCTTTGCCCGCTTGGGTTCCCCCCCCGAAAGGTTTCCCCCCTTTTCTATATATT
(SEQ ID NO:30)

FIG. 30

09041303
TGTGAATGTGAACTTCCGCGATCTCCACTGGTGCATTAACCCACTAGTAAGATCAAGGTGAATTTACTAA
CTACGCGATACAATTGGGATCAGAAAATCTATTGCATCGGCAGCAAATCCCATCCTCCTGTCAGCACTCT
CTGGGGGCAGAGGTGACATATTCCCACCATACCGATGCAGTGGAGCTGCTACCTCAGTAGGCAGAGTTTT
CCCCCTGTCAGTGTCATTGTCCATGTCTTTGATCTCAAGAAAATCAGAGATAATCAATATGCTAACCGCT
ATCTCAAACGGAGTGTATGGTAAAACTTATTTACTAGTGCCTGATTATATTGAAGAGGAGTTCGACACAC
AAAAGATTCGAGTCTTTGAGATAGGGTTCATCAAACGGTGGCTGAATGACATGCCATTACTCCAGACAAC
CAACTATATGGTCCTCCCAGAGAATTCCAAAGCTAAGGTATGTACTATAGCAGTGGGCGAGTTGACACTG
GCTTCCTTGTGTGTAGGTGAGAGCACCGTGTCATTATATCATGACAGCAATGGTTCGCAAGATAGTATCC
TAGCAGTGACGCTGGGAATATTTGGGGCAACATCTATGGATCAAGTTGAAGAGGTGATACCTGTTGCTCA
CCCATCAGTAGAAAAAATACATATAACAAATCACCGTGGGTTCATAAAAGATTCAATAGCAACCTGGATG
GTGCCTGCATTGGTCTCTGAGAAACAGGAAGAGCAAAAAAATTGTCTGGAGTCGGCTTGTCAAAGAAAAT
CCTACCCTATGTGCAACCAAACGTCATGGGAACCCTTCGGAGGAGGACAGTTGCCATCTTATGGCGGTT
GACATTACCTCTAGATCCAAGCACTGACCTTCAACTTAACATATCGTTTACATACGGTCCGGTTATACTG
AATGGAGACGGTATGGATTATTATGAAAGCCCACTGTCGGACTCCGGATGGCTTACCATTCCTCCCAAAA
ACGGAACAGTCCTTGGATTGATAAACAAAGCAAGTAGAGGAGACCAGTTCATTGTAATCCCCCATGTGTT
GACATTTGCGCCCAGGGAATCAAGTGGGAATTGTTATTTACCTATTCAAACATCCCAGATTATGAAAAGA
TGCCTTAACCCG (SEQ ID NO: 31)

FIG. 31

09041474A
TCTGCTGCTTAACCACCTAGTAAGATCAGGTGAATTTTACTAACTACTGCGATACAATTGGGATCAGAAA
ATCTATTGCATCGGCAGCAAATCCCATCCTCCTGTCAGCACTCTCTGGGGGCAGAGGTGACATATTCCCA
CCATACCGATGCAGTGGAGCTGCTACCTCAGTAGGCAGAGTTTTCCCCCTGTCAGTGTCATTGTCCATGT
CTTTGATCTCAAGAAAATCAGAGATAATCAATATGCTAACCGCTATCTCAAACGGAGTGTATGGTAAAAC
TTATTTACTAGTGCCTGATTATATTGAAGAGGAGTTCGACACACAAAAGATTCGAGTCTTTGAGATAGGG
TTCATCAAACGGTGGCTGAATGACATGCCATTACTCCAGACAACCAACTATATGGTCCTCCCAGAGAATT
CCAAAGCTAAGGTATGTACTATAGCAGTGGGCGAGTTGACACTGGCTTCCTTGTGTGTAGGTGAGAGCAC
CGTGTCATTATATCATGACAGCAATGGTTCGCAAGATAGTATCCTAGCAGTGACGCTGGGAATATTTGGG
GCAACATCTATGGATCAAGTTGAAGAGGTGAACCTGTTGCTCACCCATCAGTAGAAAAAATACATATAAC
AAATCACCGTGGGTTCATAAAAGATTCAATAGCAACTGGATGGTGCCTGCATTGGTCTCTGAGAAACAGG
AAGAGCAAAAAATTGTCTGGAGTCGGCTTGTCAAAGAAAATCCTACCCTATGTGCAACCAAACGTCATG
GGAACCCTTCGGAGGAGGACAGTTGCCATCTTATGGGCGGTTGACATTACCTCTAGATCCAAGCACTGAC
CTTCAACTTAACATATCGTTTACATACGGTCCGGTTATACTGAATGGAGACGGTATGGATTATTATGAAA
GCCCACTGTCGGACTCCGGATGGCTTACCATTCCTCCCAAAAACGGAACAGTCCTTGGATTGATAAACAA
AGCAGTAGAGGAGACCAGTTCATTGTAATCCCCCATGTGTTGACATTTGCGCCCAGGGAATCAAGTGGGA
ATTGTTATTTACCTATTCAAACATCCAGATTATGGATAAAGATGTCCTTACTGAGTCCAAATTAGTGTGT
GTGCCTA(SEQ ID NO:32)

FIG. 32

09040826
ATTGGTTGCCCTTAACCCACCTAGTAAGATCAGGTGAATTTTACTAACTACTGCGATACAATTGGGATCA
GAAAATCTATTGCATCGGCAGCAAATCCCATCCTCCTGTCAGCACTCTCTGGGGGCAGAGGTGACATATT
CCCACCATACCGATGCAGTGGAGCTGCTACCTCAGTAGGCAGAGTTTTCCCCCTGTCAGTGTCATTGTCC
ATGTCTTTGATCTCAAGAAAATCAGAGATAATCAATATGCTAACCGCTATCTCAAACGGAGTGTATGGTA
AAACTTATTTACTAGTGCCTGATTATATTGAAGAGGAGTTCGACACACAAAAGATTCGAGTCTTTGAGAT
AGGGTTCATCAAACGGTGGCTGAATGACATGCCATTACTCCAGACAACCAACTATATGGTCCTCCCAGAG
AATTCCAAAGCTAAGGTATGTACTATAGCAGTGGGCGAGTTGACACTGGCTTCCTTGTGTGTAGGTGAGA
GCACCGTGTCATTATATCATGACAGCAATGGTTCGCAAGATAGTATCCTAGCAGTGACGCTGGGAATATT
TGGGGCAACATCTATGGATCAAGTTGAAGAGGTGATACCTGTTGCTCACCCATCAGTAGAAAAAATACAT
ATAACAAATCACCGTGGGTTCATAAAAGATTCAATAGCAACCTGGATGGTGCCTGCATTGGTCTCTGAGA
AACAGGAAGAGCAAAAAATTGTCTGGAGTCGGCTTGTCAAAGAAAATCCTACCCTATGTGCAACCAAAC
GTCATGGGAACCCTTCGGAGGAGGACAGTTGCCATCTTATGGGCGGTTGACATTACCTCTAGATCCAAGC
ACTGACCTTCAACTTAACATATCGTTTACATACGGTCCGGTTATACTGAATGGAGACGGTATGGATTATT
ATGAAAGCCCACTGTCGGACTCCGGATGGCTTACCATTCCTCCCAAAAACGGAACAGTCCTTGAATGATA
AACAAAGCAAGTAGAGGAGACCAGTTTATTGTACTCCCTCTGTGTTTGACATTTGCGCCCAGGATCAAGT
GGCATTGTTTCTACCTATCCAAACTTCCGAATTATGGATAAAGATGTCCTTACTGATCCAAACTAGTGCG
TTGCTCAA(SEQ ID NO:33)

| CDV Isolate | | 191

Figure 34C

| CDV Isolate | | 294 | 295 | 296 | 298 | 301 | 302 | 303 | 309 | 311 | 314 | 315 | 317 | 319 | 321 | 322 | 323 | 324 | 327 | 330 | 331 | 332 | 333 | 337 | 340 | 341 |
|---|---|---|---|---|---|---|---|---|---|---|---|---|---|---|---|---|---|---|---|---|---|---|---|---|---|---|
| Reference | Onderstepoort | TCC | TTG | TGT | GAA | ACT | GTA | TTA | AGT | TCA | GGT | ATT | GTA | ACA | GGG | ATA | TTT | TGG | CCT | CAC | ATT | GAG | GAA | GTC | CCA | TCA |
| | AY964110(EW) | TCC | GTG | TGT | GGT | ACC | GTG | TTG | AAT | TCG | AGT | ATC | GCA | ACG | GGA | ATA | TTT | GGG | TCT | CAA | GTT | GAA | GAG | GTT | CCA | TCA |
| | AF112189(AM-2) | TCC | TTG | TGT | GAT | ACC | GTA | TTG | GAT | TCG | GGT | ATT | GTA | ACG | GGA | ATA | TTT | GGG | CCT | CAA | GTT | GAA | GAG | GTT | CCA | TTA |
| | AY962122(AR) | TCC | TTG | TGT | GAT | ACT | GTA | TTA | AAT | TCA | GGT | ATT | GTG | ACG | GGA | ATC | TTT | GGC | CCT | CAA | GTC | GAA | GAG | GTC | CCA | TCA |
| European Wildlife | 9041474 | TCC | TTG | TGT | GGT | ACC | GTG | TCA | AAT | TCG | AGT | ATC | GCA | ACG | GGA | ATA | TTT | GGG | TCT | CAA | GTT | GAA | GAG | GTT | CCA | TCA |
| |

| | Isolate | 342 | 343 | 347 | 348 | 349 | 352 | 353 | 354 | 356 | 358 | 365 | 366 | 367 | 370 | 371 | 372 | 373 | 375 | 376 | 380 | 386 | 388 | 391 | 393 | 396 |
|---|---|---|---|---|---|---|---|---|---|---|---|---|---|---|---|---|---|---|---|---|---|---|---|---|---|---|
| Reference | Ondersteport | ATG | GAG | ATA | ACA | AAC | GGT | TTT | ATA | GAT | ATT | GCC | CTG | GCC | AAA | CAA | GAA | GAA | AAA | GGT | TCA | ACC | CCC | AAC | ACG | GAA |
| | AY964110(EW) | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | AF112189(AM-2] | GTA | GAA | ATA | ACA | AAT | GGG | TTC | ATA | GAT | ATA | GCA | TTG | GTA | AAA | CAA | GAG | GAA | AAA | AAT | TCG | TCC | CCT | AAC | ACG | GAA |
| | AY962112(AR) | GTC | GAA | ATA | ACA | AAT | GGT | TTC | ATA | GAT | GTA | GCA | TTG | GTC | AAC | CTA | GAG | GAA | GAA | AAT | TCG | TCC | CCT | AAT | ACA | GAA |
| European Wildlife | 9041474 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 8120857 | ND | ND | ND | ND | ND | ND | ND | ND | ND | ND | ND | ND | ND | ND | ND | ND | ND | ND | ND | ND | ND | ND | ND | ND | ND |
| | 9041303 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 8031346 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 7091032 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 7091030 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 7111080 | GTA | GAA | ATA | ACA | AAT | GGG | TTC | ATA | GAT | ATA | GCA | TTG | GTC | AAA | CAG | GAA | GAG | AAA | AAA | TCG | TCC | CCT | AAC | ACG | GAA |
| | 08011277A | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GGA |
| | 8080941 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 08011277C | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 7101508 | GTA | GAA | ATA | ACA | AAT | GGG | TTC | ATA | GAT | ATA | GCA | TTG | GTC | AAA | CAG | GAA | GAG | AAA | ATT | TCG | TCC | CCT | AAC | ACG | GAA |
| | 8010939 | GTA | GAA | ATA | ACA | AAT | GGG | TTC | ATA | GAT | ATA | GCA | TTG | GTC | AAA | CAG | GAA | GAG | AAA | AAT | TCG | TCC | CCT | AAC | ACG | GAA |
| | 7091031 | ND | ND | ND | ND | ND | ND | ND | ND | ND | ND | ND | ND | ND | ND | ND | ND | ND | ND | ND | ND | ND | ND | ND | ND | ND |
| American-2 | 09020504-3(08-7589) | GTA | GAA | ATG | GCA | AAT | GGG | TTC | ATC | GAT | ATA | GCA | TTG | GTC | AAA | CAA | GAG | GAA | AAA | AAT | TCG | TCC | CCT | AAC | ACG | GAA |
| | 8060351 | GTA | GAA | ATA | GCA | AAT | GGG | TTC | ATC | GAT | ATA | GCA | TTG | GTC | AAA | CAA | GAG | GAA | AAA | AAT | TCG | TCC | CCT | AAC | ACG | GAA |
| | 8021509 | ND | ND | ND | ND | ND | ND | ND | ND | ND | ND | ND | ND | ND | ND | ND | ND | ND | ND | ND | ND | ND | ND | ND | ND | ND |
| | 9050216 | ND | ND | ND | ND | ND | ND | ND | ND | ND | ND | ND | ND | ND | ND | ND | ND | ND | ND | ND | ND | ND | ND | ND | ND | ND |
| | 8050180 | GTA | GAA | ATA | GCA | AAT | GGG | TTC | ATC | GAT | ATA | GCA | TTG | GTC | AAA | CAA | GAG | GAA | AAA | AAT | TCG | TCC | CCT | AAC | ACG | GAA |
| | 8030777 | GCA | GAA | ATA | ACA | AAT | GGG | TTC | ATA | GAC | ATA | GCA | TTG | GTT | AAA | CAA | GAG | GAA | GCA | AAT | TCG | TCC | CCT | AAT | ACG | GAA |
| Arctic | 7110098 | GTC | GAA | ATA | ACA | AAT | GGT | TTC | ATA | GAT | GTA | GCA | TTG | GTC | AAC | CTA | GAG | GAA | GAA | AAT | TCG | TCC | CCT | AAT | ACA | GAA |
| | | atgM<br>gtaV<br>gtcV | O | ataI<br>atgM | acaT<br>gcaA | O | ggtG<br>gggG | O | ataI<br>atcI | O | attI<br>ataI<br>gtaV | O | O | gccA<br>gtcV<br>gtaV<br>gttV | aaaK<br>aacN | caaQ<br>cagQ<br>ctaL | gaaE<br>gagE | gaaE<br>gagE | gcaA<br>gaaE<br>aaaK | O | O | O | O | aacN<br>aatN | acaT<br>acgT | |

Figure 34 E

| CDV Isolate | | 398 | 401 | 410 | 411 | 412 | 414 | 415 | 416 | 417 | 418 | 419 | 420 | 422 | 423 | 424 | 425 | 427 | 428 |
|---|---|---|---|---|---|---|---|---|---|---|---|---|---|---|---|---|---|---|---|
| Reference | Onderstepoort | TTC | AGA | ACA | TTA | CCT | GAT | GCA | AGT | GTT | GAC | CTT | CAA | AAC | CTA | TCG | TTC | TAC | GGT |
| | AY964110(EW) | TTT | GGA | ACA | TTA | CCT | GAT | CCA | AGC | ACT | GAC | CTT | CAA | AAC | CTA | TCG | TTT | TAC | GGT |
| | AF112189(AM-2) | TTT | GGA | ACA | TTA | CCT | GAT | CCA | AGC | ATT | GAC | CTT | CAA | AAC | CTC | TCG | TTT | TAC | GGT |
| | AY962112(AR) | TTT | GGA | ACG | TTA | CAT | GAT | GCA | AGC | ATT | GAC | CGT | CAA | AAC | CTA | TCA | TTT | TAC | GGT |
| European Wildlife | 9041474 | TTC | GGA | ACA | TTA | CCT | GAT | CCA | AGC | ACT | GAC | CTT | CAA | AAC | CTA | TCG | TTT | TAC | GGT |
| | 8120857 | TTC | ND | ND | ND | ND | ND | ND | ND | ND | ND | ND | ND | ND | ND | ND | ND | ND | ND |
| | 9041303 | TTC | GGA | ACA | TTA | CCT | GAT | CCA | AGC | ACT | GAC | CTT | CAA | AAC | CTA | TCG | TTT | TAC | GGT |
| | 8031346 | TTC | GGA | ACA | ATT | CCT | GAT | CCA | AGC | ACT | GAC | CTT | CAA | TAC | CTA | TCG | TTT | TAC | ND |
| | 7091032 | TTC | GGA | GAC | TTT | CCT | GAT | CCA | AGC | ACT | GAA | CTT | CAA | AAC | CTA | TCG | TTT | TAC | CGG |
| | 7091030 | TTC | GGA | ACA | TTA | CCT | GAT | CCA | AGC | ACT | GAC | CTT | CAA | AAC | CTA | TCG | TTT | TAC | GGT |
| | 7111080 | ND | ND | ND | ND | ND | ND | ND | ND | ND | ND | ND | ND | ND | ND | ND | ND | ND | ND |
| | 08011277A | TTC | GGA | ACA | TTA | CCT | GAT | CCA | AGC | ACT | GAC | CTT | CAA | AAC | CTA | TCG | TTT | TAC | CGT |
| | 8080941 | TTC | GGA | ACT | TTA | CCT | GAT | CCA | AGC | ACT | GAC | CTT | CAA | AAC | CTA | TCG | TTT | TAC | ND |
| | 08011277C | TTC | GGA | ACA | TTA | CCT | GAT | CCA | AGC | ACT | GAC | CTT | CAA | AAC | CTA | TCG | TTT | TAC | GGT |
| | 7101508 | TTC | GGA | ACA | TTA | CCT | GAT | CCA | AGC | ACT | GAC | CTT | CAA | AAC | CTA | TCG | TTT | TAC | GGT |
| | 8010939 | TTC | GGA | ACA | TTA | CCT | GAT | CCA | AGC | ACT | GAC | CTT | CAA | AAC | CTA | TCG | TTT | TAC | GGT |
| | 7091031 | ND | ND | ND | ND | ND | ND | ND | ND | ND | ND | ND | ND | ND | ND | ND | ND | ND | ND |
| American-2 | 09020504-3(08-7589) | TTT | GGA | ACA | TTA | CCT | GAT | CCA | AGC | ATT | GAC | CTT | CAC | AAC | ATC | TCA | TTT | TAC | GGC |
| | 8060351 | TTT | GGA | ACA | TTA | CCT | GAT | CCA | AGC | ATT | GAC | CTT | CAG | AAC | ATC | TCA | TTT | TAC | GGC |
| | 8021509 | ND | ND | ND | ND | ND | ND | ND | ND | ND | ND | ND | ND | ND | ND | ND | ND | ND | ND |
| | 9050216 | TTT | GGA | ACA | TTA | CCT | CAT | CCA | AGC | ATT | GAC | CTC | CAG | AAC | ATC | TCA | TTT | TAT | GGT |
| | 8050180 | TTT | GGA | ACA | TTA | CCT | CAT | CCA | AGC | ATT | GAC | CTC | CAA | AAC | CTA | TCA | TTT | TAC | GGT |
| | 8030777 | TTT | GGA | ACA | TTA | CAT | GAT | CCA | AGC | ATT | GAC | CTT | CAA | AAC | CTA | TCA | TTT | TAC | GGT |
| Arctic | 7110098 | ttcP | O | acaT | ttaL | cctP | gatD | O | O | gttV | gacD | cttL | caaQ | aacN | ctaL | tcgS | tcF | tacC | ggtG |
| | | ttcP | | agtT | ttcF | catH | catH | | | actT | gaaE | ggtR | cacH | tacY | cctL | tcaS | ttcF | tatY | ggcG |
| | | | | gacD | | | | | | attI | | ctcL | cagQ | | actI | | | | |

- 09060352-204+ — AM-2
- 08060351: 204+ — AM-2
- 09050216-204+ — AM-2
- AF112189 American-2
- 09020504-3 (08-75891): 204+ — AM-2
- 08050180A-204+ — AM-2
- 09020504-204+ — AM-2
- 08050180B-204+ — AM-2
- 08050180 — AM-2
- Z47762 American-2
- Pfizer 1310E — Vaccine
- AF478550 Europe
- DQ494318 Europe
- 08021509 — AM-2
- AB0470767 Asia - 2  ] Asia-2
- AB252718 Asia - 2
- AY964112 Arctic ] Arctic
- AY964108 Artic
- 07110098 — AR
- AB016776 Asia -1 ] Asia-1
- AB212963 Asia - 1
- AY378091 Asia - 1
- 08120857A — EW
- 08080941 CDV 204 + — EW
- 07100818 (07101508) — EW
- 09041474B (09040825): 204+ — EW ⎫ Littermates
- 09041303: 204+ — EW ⎭
- 09041474A09040825):204+ — EW
- AY964110EW
- 08031346 — EW
- 07091032 — EW
- 07091030 — EW     } EW Cluster
- 07110302 (07111080) — EW
- 08011277A ]
- 08011277C  } EW
- 08011277AB ]
- 08010839
- 07091031 — EW
- AF259552 American-2
- 09051284 CDV 204+ Galaxy-D ] Galaxy D
- GALAXY 1310A                 } 3 different trials
- 09051284 Galaxy D
- AF378705 Onderstepoort
- Merial 1310D
- 09061125 Proguard          } Vaccines
- Continuum 1310B
- Duramune 1310C
- 09061125 (Intervet Proguard)
- 08080698 CDV 204+ AM-2
- 08081112-204+ AM-2
- 07100609 ⚫ Marine-Mammal CDV-like Virus
- 09011024: 204+ EW
- M. virus Edmonston B hemagglutinin   Measles
- C. distemper virus Argentina 23 hemagglu  ]
- C. distemper virus Pao2003Arg90 hemagglu   } South American Lineage
- C. distemper virus Argentina 24 hemagglu
- C. distemper virus Bruno107Arg2005 hemag ]

Brackets on right: AMERICAN-2 (AM-2), EUROPE (E), AS-2, AR, AS-1, EUROPEAN-WILDLIFE (EW), AMERICAN-1 (AM-1), SA

09041474B atgctctcctaccaagacaaggtgggtgccttctataaggataatgcaagagctaattcatccaagctgt
ccctagtgacagaagagcaaggggggcaggagaccaccctatttgctgtttgtccttctcatcctactggt
tggaatcctggccttgcttgctatcactggagttcgatttcaccaagtatcaactagcaacgtggaattt
agcagattgctaaaagaggatatggagaaatcagaggctgtacatcaccaagtcatagatgttttgacgc
cgctcttcaaaattattggagatgagattgggttacggctgccacaaaaactaaacgagatcaaacaatt
catccttcaaaagacaaacttcttcaatcctaacagggaattcgacttccgtgatctccactggtgcatt
aacccacctagtaagatcaaggtgaattttactaactactgcgatacaattgggatcagaaaatctattg
catcggcagcaaatcccatcctcctgtcagcactctctgggggcagaggtgacatattcccaccataccg
atgcagtggagctgctacctcagtaggcagagttttccccctgtcagtgtcattgtccatgtctttgatc
tcaagaaaatcagagataatcaatatgctaaccgctatctcaaacggagtgtatggtaaaacttatttac
tagtgcctgattatattgaagaggagttcgacacacaaaagattcgagtcttttgagatagggttcatcaa
acggtggctgaatgacatgccattactccagacaaccaactatatggtcctcccagagaattccaaagct
aaagtatgtactatagcagtgggcgagttgacactggcttccttgtgtgtaggtgagagcaccgtgtcat
tatatcatgacagcaatggttcgcaagatagtatcctagcagtgacgctgggaatatttggggcaacatc
tatggatcaagttgaagaggtgatacctgttgctcacccatcagtagaaaaaatacatataacaaatcac
cgtgggttcataaaagattcaatagcaacctggatggtgcctgcattggtctctgagaaacaggaagagc
aaaaaaattgtctggagtcggcttgtcaaagaaaatcctaccctatgtgcaaccaaacgtcatgggaacc
cttcggaggaggacagttgccatcttatgggcggttgacattacctctagatccaagcactgaccttcaa
cttaacatatcgtttacatacggtccggttatactgaatggagacggtatggattattatgaaagcccac
tgtcggactccggatggcttaccattcctcccaaaaacggaacagtccttggattgataaacaaagcaag
tagaggagaccagttcattgtaatcccccatgtgttgacatttgcgcccagggaatcaagtgggaattgt
tatttacctattcaaacatcccagattatggataaagatgtccttactgagtccaatttagtggtgttgc
ctacacagaatttagatatgtcatagcaacatatgatatatcccgggacaatcatgcgatcgtttacta
tgtctatgacccaattcggacgatttcttatacgtacccatttagactaactaccaaaggtagacctgat
ttcctaaggattgaatgttttgtttgggatgatgatttgtggtgtcaccagttctaccgattcgaggctg
acatcactaactctaccaccagtgttgagaatttagtccgtataagattctcatgtaaccgttcaagacc
ttga (SEQ ID NO: 42)

ATGCTCTCCTACCGAGACAAGGTGGGTGCCTTCTATAAGGACAATGCTAGAGCTAATTCATCCAAGCTGT
CCTTAGTGACAGAAGAGCAAGGGGGCAGGAGACCACCCTATTTGCTGTTTGTCCTTCTCATCCTACTGGT
TGGAATCATGGCCTTGCTTGCTATCACTGGAGTTCGATTTCACCAAGTATCAACTAGCAATATGGAGTTT
AGCAGATTGCTGAAAGAGGATCTGGAGAAATCAGAGGCCGTACATCACCAAGTCATAGATGTCTTGACGC
CGCTCTTCAAAATTATTGGAGATGAGATTGGGTTACGGTTGCCACAAAAACTAAACGAGATCAAACAATT
TATCCTTCAAAAGACAAACTTCTTCAATCCGAACAGGGAATTCGACTTCCGCGATCTCCACTGGTGCATT
AACCCACCTAGTAAGATCAAGGTGAATTTTACTAATTACTGCGATACTATGGGGATCAGAAAATCTATTG
CATCGGCAGCAAATCCCATCCTTTTATCAGCACTCTCCGGAGGTAGAGGTGACATATTCCCACCATACAG
ATGCAATGGAGCTACTATTTCAGTAGGCAAGATTTTCCCCCTATCAGTATCATTATCTATGTCTTTGATC
TCAAGAACATCAGAGATAATCAATATGCTAACCGCTATCTCAGACGGAGTGTATGGTAAAACTTATTTAC
TAATGCCTGATTATATTGAAGGGGAGTTCGACACGCAAAAGATTCGAGTCTTTGAGATAGGGTTCATCAA
ACGGTGGCTGAATGACATGCCATTACTCCAGACAACCAACTATATGGTCCTCCCAGAGAATTCCAAAGCT
AAGGTATGTACTATAGCAGTGGGCGAGTtGACACTGGCTTCTTTGTGTGTAGGTGAGAGCACCGTATTGT
TATATCATGACAGCAATGGTTCACAAGATGGTATTCTAGTAGTGACGCTGGGAATATTCGGGGCAACATC
TATGGATCAAGTTGAAGAGGTGATACCTGTCGCTGACCCATTAGTAGAAAAAATACATATAACAAATCAC
CGCGGGATCATAAAAGATTCAATAGCAACCTGGATGGTGCCTGCATTAGTTTCTGAGAAACAAGAGGAAC
AAAAAAATTGTCTGGAGTCAGCTTGTCAAAGAAAATCCTACCCTATGTGCAATCAAACGTCATGGGAACC
CTTTGGAGGAGGACAGTTGCCATCTTATGGGCGGTTGACATTACCTCTAGATCCAAGCATTGACCTTCAA
CTTAACATATCATTTACATACGGTCCGATTATACTGAATGGGACGGTATGGATTATTATGAGAGCCCAC
TGTTGGACTCCGGATGGCTTACCATTCCTCCCAAGAACGGAACAGTCCTTGGATTGATAAACAAAGCAAG
TAGAGGAGACCAGTTCACTGTAATCCCCCATGTGTTGACATTTGCGCCCAGGGAATCAAGTGGAAATTGT
TATTTACCTATTCAAACATCCCAGATTATGGATAAAGATGTCCTTACTGAGTCCAATTTAGTGGTGTTGC
CTACACAGAATTTTAGATATGTCGTAGCAACATATGATATATCTCGGGACGATCATGCGATTGTTTATTA
TGTTTATGACCCAATACGGACGATTTCTTATACGTACCCATTTAGACTAACTACTAAGGGTAGACCTGAT
TTCTTAAGGATTGAGTGTTTTGTGTGGGATGACGATTTGTGGTGTCACCAGTTTTACCGATTCGAGGCCG
ACATCACCAACTCTACAACCAGTGTCGAGAATTTAGTCCGTATGAGATTCTCATGTAACCGTTCCAGACC
TTGA (SEQ ID NO: 43)

Figure 38

```
MLSYQDKVGAFYKDNARANSSKLSLVTEEQGGRRPPYLLFVLLILLVGILALLAITGVRFHQVSS
NVEFSRLLKEDMEKSEAVHHQVIDVLTPLFKIIGDEIGLRLPQKLNEIKQFILQKTNFFNPNREF
DFRDLHWCINPPSKIKVNFTNYCDTIGIRKSIASAANPILLSALSGGRGDIFPPYRCSGAATSVG
RVFPLSVSLSMSLISRKSEIINMLTAISNGVYGKTYLLVPDYIEEEFDTQKIRVFEIGFIKRWLN
DMPLLQTTNYMVLPENSKAKVCTIAVGELTLASLCVGESTVSLYHDSNGSQDSILAVTLGIFGAT
SMDQVEEVIPVAHPSVEKIHITNHRGFIKDSIATWMVPALVSEKQEEQKNCLESACQRKSYPMCN
QTSWEPFGGGQLPSYGRLTLPLDPSTDLQLNISFTYGPVILNGDGMDYYESPLSDSGWLTIPPKN
GTVLGLINKASRGDQFIVIPHVLTFAPRESSGNCYLPIQTSQIMDKDVLTESNLVVLPTQNFRYV
IATYDISRDNHAIVYYVYDPIRTISYTYPFRLTTKGRPDFLRIECFVWDDDLWCHQFYRFEADIN
STTSVENLVRIRFSCNRSRP (SEQ ID NO: 44)
```

Fig. 39

```
MLSYRDKVGAFYKDNARANSSKLSLVTEEQGGRRPPYLLFVLLILLVGIMALLAITGVRFHQVST
SNMEFSRLLKEDLEKSEAVHHQVIDVLTPLFKIIGDEIGLRLPQKLNEIKQFILQKTNFFNPNRE
FDFRDLHWCINPPSKIKVNFTNYCDTMGIRKSIASAANPILLSALSGGRGDIFPPYRCNGATISV
GKIFPLSVSLSMSLISRTSEIINMLTAISDGVYGKTYLLMPDYIEGEFDTQKIRVFEIGFIKRWL
NDMPLLQTTNYMVLPENSKAKVCTIAVGELTLASLCVGESTVLLYHDSNGSQDGILVVTLGIFGA
TSMDQVEEVIPVADPLVEKIHITNHRGIIKDSIATWMVPALVSEKQEEQKNCLESACQRKSYPMC
NQTSWEPFGGGQLPSYGRLTLPLDPSIDLQLNISFTYGPIILNGDGMDYYESPLLDSGWLTIPPK
NGTVLGLINKASRGDQFTVIPHVLTFAPRESSGNCYLPIQTSQIMDKDVLTESNLVVLPTQNFRY
VVATYDISRDDHAIVYYVYDPIRTISYTYPFRLTTKGRPDFLRIECFVWDDDLWCHQFYRFEADI
TNSTTSVENLVRMRFSCNRSRP (SEQ ID NO: 45)
```

Fig. 40

SEQUENCE LISTING

```
<160> NUMBER OF SEQ ID NOS: 45

<210> SEQ ID NO 1
<211> LENGTH: 866
<212> TYPE: DNA
<213> ORGANISM: canine distemper virus

<400> SEQUENCE: 1
aaggtgaatt ttactaacta ctgcgataca attgggatca gaaaatctat tgcatcggca      60
gcaaatccca tcctcctgtc agcactctct gggggcagag gtgacatatt cccaccatac     120
agatgcagtg gagctgctac ctcagtaggc agagttttcc ccctatcagt gtcattgtcc     180
atgtctttga tctcaagaaa atcagagata atcaatatgc taaccgctat ctcaaacgga     240
```

```
gtgtatggta aaacttattt actagtgcct gattatattg aagaggagtt cgacacacaa    300
aagattcgag tctttgagat agggttcatc aaacggtggc tgaatgacat gccattactc    360
cagacaacca actatatggt cctcccagag aattccaaag ctaaggtatg tactatagca    420
gtgggcgagt tgacactggc ttccttgtgt gtaggtgaga gcaccgtgtt gttatatcat    480
gacagcaatg gttcgcaaga tagtatccta gcagtgacgc tgggaatatt tggggcaaca    540
actatggatc aagttgaaga ggtgatacct gttgctcacc catcagtaga aaaatacat    600 ataacaaatc accgtgggtt cataaaagat tcaatagcaa cctggatggt gcctgcattg    660
gtctctgaga aacaggaaga gcaaaaaaat tgtctggagt cggcttgtca agaaaatcc    720 taccctatgt gcaaccaaac gtcatgggaa cccttcggag gaggacagtt gccatcttat    780
gggcggttga cattacctct agatccaagc actgaccttc aacttaacat atcgtttaca    840
tacggtccgg ttatactgaa tggaga                                          866

<210> SEQ ID NO 2
<211> LENGTH: 1054
<212> TYPE: DNA
<213> ORGANISM: canine distemper virus

<400> SEQUENCE: 2
ggtgaatttt actaactact gcgatacaat tgggatcaga aaatctattg catcggcagc     60
aaatcccatc ctcctgtcag cactctctgg gggcagaggt gacatattcc caccatacag    120
atgcagtgga gctgctacct cagtaggcag agttttcccc ctatcagtgt cattgtccat    180
gtctttgatc tcaagaaaat cagagataat caatatgcta accgctatct caaacggagt    240
gtatggtaaa acttatttac tagtgcctga ttatattgaa gaggagttcg acacacaaaa    300
gattcgagtc tttgagatag ggttcatcaa acggtggctg aatgacatgc cattactcca    360
gacaaccaac tatatggtcc tcccagagaa ttccaaagct aaggtatgta ctataggagt    420
gggcgagttg acactggctt ccttgtgtgt aggtgagagc accgtgttgt tatatcatga    480
cagcaatggt tcgcaagata gtatcctagc ggtgacggtg gaatatttgg ggcaacatc    540 tatggatcaa gttgaagagg tgatacctgt tgctcaccca tcagtagaaa aatacatat    600 aacaaatcac cgtgggttca taaaagattc aatagcaacc tggatggtgc ctgcattggt    660
ctctgagaaa caggaagagc aaaaaaattg tctggagtcg gcttgtcaaa gaaaatccta    720
ccctatgtgc aaccaaacgt catgggaacc cttcggagga ggacagttgc catcttatgg    780
gcggttgaca ttacctctag atccaagcac tgaccttcaa cttaacatat cgtttacata    840
cggtccggtt atactgaatg agacggtat ggattattat gaaagcccac tgtcggactc    900
cggatggctt accattcctc ccaaaaacgg aacagtcctt ggattgataa acaaagcaag    960
tagaggagac cagttcattg taatccccca tgtgttgaca tttgcgccca gggaatcaag   1020
tgggaattgt tatttaccta ttcaaacatc ccag                                1054

<210> SEQ ID NO 3
<211> LENGTH: 785
<212> TYPE: DNA
<213> ORGANISM: canine distemper virus

<400> SEQUENCE: 3
ggtgaatttt actaactact gcgatacaat tgggatcaga aaatctattg catcggcagc     60
aaatcccatc ctcctgtcag cactctctgg gggcagaggt gacatattcc caccatacag    120
atgcagtgga gctgctacct cagtaggcag agttttcccc ctatcagtgt cattgtccat    180
```

```
gtctttgacc tcaagaaaat cagagataat caatatgcta accgctatct caaacggagt      240
gtatggtaaa acttatttac tagtgcctga ttatattgaa gaggagttcg acacacaaaa      300
gattcgagtc tttgagatag ggttcatcaa acggtggctg aatgacatgc cattactcca      360
gacaactaac tatatggtcc tcccagagaa ttccaaagct aaggtatgta ctatagcagt      420
gggcgagttg acactggctt ccttgtgtgt aggtgagagc accgtgttgt tatatcatga      480
cagcaatggt tcgcaagata gtatcctagc agtgacgctg gaatatttg gggcaacatc       540 tatggatcaa gttgaagagg tgatacctgt tgctcaccca tcagtagaaa aaatacatat      600
aacaaatcac cgtgggttca taaaagattc aatagcaacc tggatggtgc ctgcattggt      660
ctctgagaaa caggaagagc aaaaaaattg tctggagtcg gcttgtcaaa gaaaatccta      720
ccctatgtgc aacccaaacg tcatgggaac ccttcggagg aggacagttg ccatcttatg      780
ggcgg                                                                  785
```

<210> SEQ ID NO 4
<211> LENGTH: 908
<212> TYPE: DNA
<213> ORGANISM: canine distemper virus
<220> FEATURE:
<221> NAME/KEY: misc_feature
<222> LOCATION: (815)..(815)
<223> OTHER INFORMATION: n is a, c, g, or t
<220> FEATURE:
<221> NAME/KEY: misc_feature
<222> LOCATION: (880)..(880)
<223> OTHER INFORMATION: n is a, c, g, or t

<400> SEQUENCE: 4

```
ctagtaagat caggtgaatt ttactaatta ctgctataca attgggatca gaaaatctat       60
tgcatcggca gcaaatccca tcctccagtc agcactctct gggggcagag gtgacatatt      120
cccaccatac agatgcagtg agctgctac ctcagtaggc agagttttcc ccctatcagt       180
gtcattgtcc atgtctttga tctcaagaaa atcagagata atcaatatgc taaccgctat      240
ctcaaacgga gtgtatggta aaacttattt actagtgcct gattatattg aagaggagtt      300
cgacacacaa aagattcgag tctttgagat agggttcatc aaacggtggc tgaatgacat      360
gccattactc cagacaacca actatatggt cctcccagag aattccaaag ctaaggtatg      420
tactatagca gtgggcgagt tgacactggc ttccttgtgt gtaggtgaga gcaccgtgtt      480
gttatatcat gacagcaatg gttcgcaaga taatatccta gtagtgacgc tgggaatatt      540
tggggcaaca tctatggatc aagttgaaga ggtgatacct gttgctcacc catcagtaga      600
aaaaatacat ataacaaatc accgtgggtt cataaaagat tcaatagcaa cctggatggt      660
gcctgcattg gtctctgaga aacaggaaga gcaaaaaatt tgtctggagt cggcttgtca      720
aagaaaatcc tacccctatgt gcaaccaaac gtcatgggaa cccttcggag gaggacagtt      780
gccatcttat gggcggttga cattacctct agatncaagc actgaccttc aacttaacat      840
atcgtttaca tacggtccgg ttatactgaa tggagacggn atggattatt atgaaagccc      900
actgtcgg                                                               908
```

<210> SEQ ID NO 5
<211> LENGTH: 380
<212> TYPE: DNA
<213> ORGANISM: canine distemper virus

<400> SEQUENCE: 5

```
aacttgtatc cggctcttgg gttgcatgag ttttccgggg agttaacaac cattgaatcc       60
```

| | |
|---|---|
| cttatgatgc tatatcaaca gatgggtgaa acagcaccgt acatggttat tctggaaaat | 120 |
| tctgtccaga acaaatttag tgcaggatcc tacccattgc tctggagtta tgctatggga | 180 |
| gttggtgttg aacttgaaaa ctccatggga gggttaaatt tcggtagatc ctactttgac | 240 |
| ccagcttatt tcaggctcgg gcaagaaatg gttagaagat cggccggtaa ggtaagctct | 300 |
| gcacttgccg ccgagcttgg catcaccaag gaagaggctc agctagtgtc agaaatagca | 360 |
| tccaagacaa cagaggacca | 380 |

<210> SEQ ID NO 6
<211> LENGTH: 847
<212> TYPE: DNA
<213> ORGANISM: canine distemper virus

<400> SEQUENCE: 6

| | |
|---|---|
| aagtgaattt tactagttac tgtgatacaa ttgggatcag aaaatccatt gcattggcag | 60 |
| caaatcccgt cctttgtca gcactctccg gaggcagagg tgacatattc ccaccataca | 120 |
| gatgcagtgg agctactact tcagttggca aatctttccc cctatcagta tcattatcca | 180 |
| tgtctttgat ctcaagaaca tcagagataa tcaatatgct gacctctatc tcagacggag | 240 |
| tgtatggtaa aacttatttg ctagtgcctg attatattga aggggagttc gacacgcaaa | 300 |
| agattcgagt ctttgagata gggttcatca aaaggtggct gaatgacatg ccattattcc | 360 |
| agacaaccaa ctatatgatc ctcccggaga attctaaaac caaggtatgt actatagcag | 420 |
| tgggcgagtt gacactggct tccttgtgtg tagatgagag cactgtatta ttatatcatg | 480 |
| acagcaatgg ttcacaagat ggtattctag tagtgacgct gggaatcttt ggggcaacac | 540 |
| ctatggatca gtcgaagag gtgatacctg tcgctcaccc atcagtcgaa aaatacata | 600 |
| taacaaatca ccgtggtttc ataaaagatt cagtagcaac ctggatggtg cctgcattgg | 660 |
| tctctgagaa cctagaggaa caagaaaatt gtctggagtc ggcttgtcag agaaaatcct | 720 |
| accctatgtg caatcaaaca tcatgggaac cctttggagg aggacagttg ccatcttatg | 780 |
| ggcggttgac gttacatcta gatgcaagca ttgaccgtca acttaacata tcatttacat | 840 |
| acggtcc | 847 |

<210> SEQ ID NO 7
<211> LENGTH: 871
<212> TYPE: DNA
<213> ORGANISM: canine distemper virus

<400> SEQUENCE: 7

| | |
|---|---|
| tcaagaaaat cagagataat caatatgcta cccgctatct caaacggagt gtatggtaaa | 60 |
| acttatttac tagtgcctga ttatatgaag aggagttcga cacacaaaag attcgagtct | 120 |
| ttgagatagg gttcatcaaa cggtggctga atgacatgcc attactccag acaaccaact | 180 |
| atatggtcct cccagagaat ccaaaagcta aggtatgtac tatagcagtg ggcgagttga | 240 |
| cactggcttc cttgtgtgta gatgagagca ccgtgttgtt atatcatgac agcaatggtt | 300 |
| cgcaagatag tatcctagca gtgacgctgg gaatatttgg ggcaacatct atggatcaag | 360 |
| ttgaagaggt gatacctgtt gctcactcat cagtagaaaa aatacatata acaaatcacc | 420 |
| gtgggttcat aaaagattca atagcaacct ggatggtgcc tgcattggtc tctgagaaac | 480 |
| aggaagagca aaaaaattgt ctggagtcgg cttgtcaaag aaaatcctac cctatgtgca | 540 |
| accaaacgtc atgggaaccc ttcggaggag acagttgcc atcttatggg cggttgacat | 600 |
| tacctctaga tccaagcact gaccttcaac ttaacatatc gtttacatac ggtccggtta | 660 |

| tactgaatgg agacggtatg gattattatg aaagcccact gtcggactcc ggatggctta | 720 |
| ccattcctcc caaaaacgga acagtccttg gattgataaa taaagcaagt agaggagacc | 780 |
| agttcattgt aatccccat gtgttgacat ttgcgcccag ggaatcaagt gggaattgtt | 840 |
| atttacctat tcaaacatcc cagattatag a | 871 |

<210> SEQ ID NO 8
<211> LENGTH: 900
<212> TYPE: DNA
<213> ORGANISM: canine distemper virus

<400> SEQUENCE: 8

| gaatttttact aattactgcg atacaattgg gatcagaaaa tctattgcat cggcagcaaa | 60 |
| tcccatcctc ctgtcagcac tctctggggg cagaggtgac atattcccac catacagatg | 120 |
| cagtggagct gctacctcag taggcagagt tttcccccta tcagtgtcat tgtccatgtc | 180 |
| tttgatctca agaaaatcag agataatcaa tatgctaacc gctatctcaa acggagtgta | 240 |
| tggtaaaact tatttactag tgcctgatta tattgaagag gagttcgaca cacaaaagat | 300 |
| tcgagtcttt gagataggt tcatcaaacg gtggctgaat gacatgccat tactccagac | 360 |
| aaccaactat atggtcctcc cagagaattc caaagctaag gtatgtacta tagcagtggg | 420 |
| cgagttgaca ctggcttcct tgtgtgtagg tgagagcacc gtgttgttat atcatgacag | 480 |
| caatggttcg caagataata tcctagtagt gacgctggga atatttgggg caacatctat | 540 |
| ggatcaagtt gaagaggtga tacctgttgc tcacccatca gtagaaaaaa tacatataac | 600 |
| aaatcaccgt gggttcataa aagattcaat agcaacctgg atggtgcctg cattggtctc | 660 |
| tgagaaacag gaagagcaaa aaaattgtct ggagtcggct tgtcaaagaa atcctaccc | 720 |
| tatgtgcaac caaacgtcat gggaacccttt cggaggagga cagttgccat cttatgggcg | 780 |
| gttgacatta cctctagatc caagcactga ccttcaactt aacatatcgt ttacatacgg | 840 |
| tccgggttat actgaatgga gacggtatgg attattatga aagcccactg tcggactccg | 900 |

<210> SEQ ID NO 9
<211> LENGTH: 1133
<212> TYPE: DNA
<213> ORGANISM: canine distemper virus

<400> SEQUENCE: 9

| gccgggctgc atcacccccct agtaagacag gtgaattttta cttattactg cgatacaatt | 60 |
| gggatcagaa atctattgc atcggcagca atcccatcc tcctgtcagc actctctggg | 120 |
| ggcagaggtg acatattccc accatacaga tgcagtggag ctgctacctc agtaggcaga | 180 |
| gttttccccc tatcagtgtc attgtccatg tctttgatct caagaaaatc agagataatc | 240 |
| aatatgctaa ccgctatctc aaacggagtg tatggtaaaa cttatttact agtgcctgat | 300 |
| tatattgaag aggagttcga cacacaaaag attcgagtct ttgagatagg gttcatcaaa | 360 |
| cggtggctga tgacatgcc attactccag acaaccaact atatggtcct cccagagaat | 420 |
| tccaaagcta aggtatgtac tatagcagtg ggcgagttga cactggcttc cttgtgtgta | 480 |
| ggtgagagca ccgtgttgtt atatcatgac agcaatggtt cgcaagataa tatcctagta | 540 |
| gtgacgctgg gaatatttgg gcaacatct atggatcaag ttgaagaggt gatacctgtt | 600 |
| gctcacccat cagtagaaaa atacatata caaatcacc gtgggttcat aaaagattca | 660 |
| atagcaacct ggatggtgcc tgcattggtc tctgagaaac aggaagagca aaaaaattgt | 720 |
| ctggagtcgg cttgtcaaag aaaatcctac cctatgtgca accaaacgtc atgggaaccc | 780 |

```
ttcggaggag acagttgcc atcttatggg cggttgacat tacctctaga tccaagcact    840
gacccttcca acttaacata tcgtttacat accgtccggt tatacttgaa tggagacggt    900
atggataatt atgaaagccc actgtcggac tcggatggct taccatttcc ttccaaaacg    960
gaacagtcct tggattgata acaaaccag taggggagac cagttcattg tatcccccat    1020
gtgttgacca ttgccccagg gaatcaaggg gaatgtattt acctattcaa ccttcccaaa    1080
taatgggata aaggatggcc ctcctgaatc caaattacgg tgttgcccta aac           1133

<210> SEQ ID NO 10
<211> LENGTH: 1120
<212> TYPE: DNA
<213> ORGANISM: canine distemper virus

<400> SEQUENCE: 10
ttggttaagg ccatcctttt tccctaatct gggctgtttg aataggtaaa taacaattcc     60
ccacttgatt ccctgggcgc aaatgtcaac acatggggga ttacaatgaa ctggtctccc    120
ctacttgctt tgtttatcaa tccaaggact gttccgtttt tgggaggaat ggtaagccat    180
ccggagtccg acagtgggct ttcataataa tccataccgt ctccattcag tataaccgga    240
ccgtatgtaa acgatatgtt aagttgaagg tcagtgcttg gatctagagg taatgtcaac    300
cgcccataag atggcaactg tcctcctccg aagggtcccc atgacgtttg gttgcacata    360
gggtaggatt ttcttgaca agccgactcc agacaatttt tttgctcttc ctgtttctca    420
gagaccaatg caggcaccat ccaggttgct attgaatctt ttatgaaccc acggtgattt    480
gttatatgta ttttttctac tgatgggtga gcaacaggta tcacctcttc aacttgatcc    540
atagatgttg ccccaaatat tcccagcgtc actactagga tattatcttg cgaaccattg    600
ctgtcatgat ataacaacac ggtgctctca cctacacaca aggaagccag tgtcaactcg    660
cccactgcta tagtacatac cttagctttg gaattctctg gaggaccat atagttggtt    720 gtctggagta atggcatgtc attcagccac cgtttgatga ccctatctc aaagactcga    780 atcttttgt gtgtcgaact cctcttcaat ataaatcagg cacctagtaa ataaagttta    840
ccatacacct ccgtttgaga tagccggtta gcatattgat tatctctgat cctcttgaga    900
tcaaagacat ggacaatgac actgataggc gggaaaactc tgcctactga ggtagcagct    960
ctactgcttt tgttgggtgg gaaatattta accctttgcc cccgaaagtg cttacaggag    1020
gatgggattt gctgccgatc caataaattt tctgatccca attgtatcga gaactaata    1080 aattacctgg accttacttg gggggggtgat gaaccagcgc                          1120

<210> SEQ ID NO 11
<211> LENGTH: 797
<212> TYPE: DNA
<213> ORGANISM: canine distemper virus

<400> SEQUENCE: 11
agatcaaggt gaattttact aattactgcg atacaattgg gatcagaaaa tctattgcat      60
cggcagcaaa tccatcctc ctgtcagcac tctctggggg cagaggtgac atattcccac     120
catacagatg cagtggagct gctaccctcag taggcagagt tttccccct tcagtgtcat    180 tgtccatgtc tttgatctca agaaaatcag agataatcaa tatgctaacc gctatctcaa    240
acggagtgta tggtaaaact tatttactag tgcctgatta tattgaagag gagttcgaca    300
cacaaaagat tcgagtcttt gagataggggt tcatcaaacg gtggctgaat gacatgccat    360
tactccagac aaccaactat atggtcctcc cagagaattc caaagctaag gtatgtacta    420
```

```
tagcagtggg cgagttgaca ctggcttcct tgtgtgtagg tgagagcacc gtgttgttat    480
atcatgacag caatggttcg caagataata tcctagtagt gacgctggga atatttgggg    540
caacatctat ggatcaagtt gaagaggtga tacctgttgc tcacccatca gtagaaaaaa    600
tacatataac aaatcaccgt gggttcataa aagattcaat agcaacctgg atggtgcctg    660
cattggtctc tgagaaacag gaagagcaaa aaaattgtct ggagtcggct tgtcaaagaa    720
aatcctaccc tatgtgcaac caaacgtcat gggaaccctt tcggaggagg acagttgcca    780
tcttatgggc ggttgac                                                   797

<210> SEQ ID NO 12
<211> LENGTH: 745
<212> TYPE: DNA
<213> ORGANISM: canine distemper virus

<400> SEQUENCE: 12
ccccaattgg cattgaacca tgtatccggc tcttgggttg catgagtttt ccggggagtt     60
aacaaccatt gaatccctta tgatgctata tcaacagatg ggtgaaacag caccgtacat    120
ggttattctg gaaaattctg tccagaacaa atttagtgca ggctcctacc cattgctctg    180
gagttatgct atgggagttg gtgttgaact tgaaaactcc atgggagggt taaatttcgg    240
tagatcctac tttgacccag cttatttcag gctcgggcaa gaaatggtta gaagatctgc    300
cggtaaggta agctctgcac ttgccgccga gctcggcatc accaaggaag aggctcagct    360
agtgtcagaa atagcatcca agacaacaga ggacctccca tttggcattg aaactatgta    420
tccggctctt gggttgcatg agttttccgg ggagttaaca acccttgaat cttaatgacc    480
tttttccgca gggaacaaac ccacaatcgc tgaattctgt gaaatatggc tcaccacatt    540
gtggcagctc gacaccgact ttaaccttac ctatggaatt tggcgttgaa actgtaaatc    600
cctcttcggg ttaccacctc ttttgatcac tttaaccgtt atttacgccg gcagccacgt    660
tagaacatat ccgccttcgc aagttttcct gcctcctcct tccacccaat tagagggccc    720
ccctcctttg ttatgaaccc cctta                                          745

<210> SEQ ID NO 13
<211> LENGTH: 1167
<212> TYPE: DNA
<213> ORGANISM: canine distemper virus

<400> SEQUENCE: 13
cctgggcgcc ttaccccccc ctagtaagct caggtgaatt ttactaacta ctgcgatacc     60
cttgggatca gaaaatctat tgcatcggca gcaaatccca tcctcctgtc agcactctct    120
gggggcagag gtgacatatt cccaccatac cgatgcagtg gagctgctac ctcagtaggc    180
agagttttcc ccctgtcagt gtcattgtcc atgtctttga tctcaagaaa atcagagata    240
atcaatatgc taaccgctat ctcaaacgga gtgtatggta aaacttattt actagtgcct    300
gattatattg aagaggagtt cgacacacaa aagattcgag tctttgagat agggttcatc    360
aaacggtggc tgaatgacat gccattactc cagacaacca actatatggt cctcccagag    420
aattccaaag ctaaggtatg tactatagca gtgggcgagt tgacactggc ttccttgtgt    480
gtaggtgaga gcaccgtgtc gttatatcat gacagcaatg gttcgcaaga tagtatccta    540
gcagtgacgc tgggaatatt tggggcaaca tctatggatc aagttgaaga ggcgatacct    600
gttgctcacc catcagtaga aaaaatacat ataacaaatc accgtgggtt cataaaagat    660
tcaatagcaa cctggatggt gcctgcattg gtctctgaga aacaggaaga gcaaaacaat    720
```
tgtctggagt cggcttgtca aagaaaatcc taccctatgt gcaaccaaac gtcatgggaa 780
cccttcggag gaggacagtt gccatcttat gggcggttga cattacctta gatccaagca 840
ctgaccttca actcaacata tcgcttacat accgtccggc tatactgaat gggagacggt 900
atggatttta tgacaagccc ccctgtcgga ctcccggatg gcttaccacc ccctcccaaa 960
accggaacag ctccttcgat tgataaacca aaccagtacg aggagactca gtttcattgt 1020
tattccccta cgtgttgaca tttccgcccc aggccatcca tgtcggattg ctctttaccc 1080
aataacccac cccacatcat ggatacagct ctccttactg actccacact accgctgttg 1140
cctaccctcc cgctctccct tcccta 1167

<210> SEQ ID NO 14
<211> LENGTH: 245
<212> TYPE: DNA
<213> ORGANISM: canine distemper virus
<220> FEATURE:
<221> NAME/KEY: misc_feature
<222> LOCATION: (161)..(161)
<223> OTHER INFORMATION: n is a, c, g, or t

<400> SEQUENCE: 14
gtgaatttta ctaattactg cgatactatg ggatcagaa aatctattgc atcggcagca 60
aatcccatcc ttttatcagc actctccgga ggtagaggtg acatattccc accatacaga 120
tgcaatggag ctactatttc agtaggcaag attttccccc natcagtatc attatctatg 180
tctttgatct caagaacatc agagataatc aatatgctaa ccgctatctc agacggagtg 240
tatgg 245

<210> SEQ ID NO 15
<211> LENGTH: 835
<212> TYPE: DNA
<213> ORGANISM: canine distemper virus
<220> FEATURE:
<221> NAME/KEY: misc_feature
<222> LOCATION: (764)..(764)
<223> OTHER INFORMATION: n is a, c, g, or t

<400> SEQUENCE: 15
caaggtgaat tttactaatt actgcgatac aattgggatc agaaaatcta ttgcatcggc 60
agcaaatccc atcctcctgt cagcactctc tgggggcaga ggtgacatat tcccaccata 120
cagatgcagt ggagctgcta cctcagtagg cagagttttc cccctatcag tgacattgtc 180
catgtctttg atctcaagaa aatcagagat aatcaatatg ctaaccgcta tctcaaacgg 240
agtgtatggt aagacttatt tactagtgcc tgattatatt gaagaggagt tcgacacaca 300
aaagattcga gtctttgaga tagggttcat caaacggtgg ctgaatgaca tgccattact 360
ccagacaacc aactatatgg tcctcccaga gaattccaaa gctaaggtat gtactatagc 420
agtgggcgag ttgacactgg cttccttgtg tgtaggtgag agcaccgtgt tgttatatca 480
tgacagcaat ggttcgcaag ataatatcct agtagtgacg ctgggaatat ttggggcaac 540
atctatggat caagttgaag aggtgatacc tgttgctcac ccatcagtag aaaaaataca 600
tataacaaat caccgtgggt tcataaaaga ttcaatagca acctggatgg tgcctgcatt 660
ggtctctgag aaacaggaag agcaaaaaaa ttgtctggag tcggcttgtc aaagaaaatc 720
ctaccctatg tgcaaccaaa cgtcatggga acccttcgga gganggacag ttgccatctt 780
atgggcggtt gacattacct ctagatccaa gcactgacct tcaacttaac atatc 835

<210> SEQ ID NO 16
<211> LENGTH: 1119
<212> TYPE: DNA
<213> ORGANISM: canine distemper virus

<400> SEQUENCE: 16

```
tcctgtttgc ctttcccccc cctagtaaga tcaggtgaat tttactaaca actgcgatac     60
aattgggatc agaaaatcta ttgcatcggc agcaaatccc atcctcctgt cagcactctc    120
tgggggcaga ggtgacatat tcccaccata cagatgcagt ggagctgcta cctcagtagg    180
cagagttttc cccctatcag tgtcattgtc catgtctttg atctcaagaa aatcagagat    240
aatcaatatg ctaaccgcta tctcaaacgg agtgtatggt aaaacttatt tactagtgcc    300
tgattatatt gaagaggagt tcgacacaca aaagattcga gtctttgaga tagggttcat    360
caaacggtgg ctgaatgaca tgccattact ccagacaacc aactatatgg tcctcccaga    420
gaattccaaa gctaaggtat gtactatagc agtgggcgag ttgacactgg cttccttgtg    480
tgtaggtgag agcaccgtgt tgttatatca tgacagcaat ggttcgcaag atagtatcct    540
agcagtgacg ctgggaatat ttggggcaac aactatggat caagttgaag aggtgatacc    600
tgttgctcac ccatcagtag aaaaaataca tataacaaat caccgtgggt tcataaaaga    660
ttcaatagca acctggatgg tgcctgcatt ggtctctgag aaacaggaag agcaaaaaaa    720
ttgtctggag tcggcttgtc aaagaaaatc ctaccctatg tgcaaccaaa cgttatggga    780
acccttcgga ggaggacagt tgccatctta tgggcggttg acattacctc tagatccaag    840
cactgacctt caacttaaca tatcgtttac atacggtccg gttatcctga atggagacgg    900
tatggattat tatgaaagcc cactgtcgga ctcccgatgg cttaccattc ctccaaaacg    960
gaacagtcct tggattgata aacaaacaag tagaggagac cagttcattg aatccccatg   1020
tgttgacttt tcgcccaggg aatcaagtgg aattgtattt actatcaact tccagattat   1080
ggataagatg tccttctgat tccaatacgg tgtgcctta                          1119
```

<210> SEQ ID NO 17
<211> LENGTH: 1126
<212> TYPE: DNA
<213> ORGANISM: canine distemper virus

<400> SEQUENCE: 17

```
tcgtggtgct taaccccccc tagtaagatc aggtgaattt tactaattac tgcgatacta     60
ttgggatcag aaaatctatt gcatcggcag caaatcccat ccttttatca gcactctccg    120
gaggtagagg tgacatattc ccaccataca gatgcaatgg agctactatt tcagtaggca    180
agattttccc cctatcagta tcattatcta tgtctttgat ctcaagaaca tcagagataa    240
tcaatatgct aaccgctatc tcagacggag tgtatggtaa aacttattta ctaatgcctg    300
attatattga aggggagttc gacacgcaaa agattcgagt ctttgagata gggttcatca    360
aacggtggct gaatgacatg ccattactcc agacaaccaa ctatatggtc ctcccagaga    420
attccaaagc caaggtatgt actatagcag tgggcgagtt gacactggct tctttgtgtg    480
tagatgagag caccgtattg ttatatcatg acagcaatgg ttcacaagat ggtgttctag    540
tagtgacgct gggaatattc ggggcaacat ctatggatca agttgaagag gtgatacctg    600
tcgctgaccc attagcagaa aaaatacata taacaaatca ccgtgggatc ataaaagact    660
caatagcaac ctggatggtg cctgcattag tttctgagaa acaagaggaa caaacaaatt    720
gtctggagtc agcttgtcaa agaaaatcct accctatgtg caatcaaacg tcatgggaac    780
cctttggagg aggacagttg ccatcttatg ggcggctgac attacctcta catccaagca    840
```

```
ttgacctcca cttaacatat catttacata cggtccgact atactgaatg gagacggatg      900
gctattatga gagcccctg cggactccgg atggcttacc tttccctcca gcacggcaca      960
gcctggattg ataaacaaag agtagaggac gaccagttat tgtcattccc ctgtgttgac     1020
atttcgcccc cggcatccac ccgaaattgc tattacccta tcccacattc cccttcgcgc    1080
tcaagatccc cctcctgctc cccaccacgg cgcgctccct atctcc                   1126

<210> SEQ ID NO 18
<211> LENGTH: 623
<212> TYPE: DNA
<213> ORGANISM: canine distemper virus

<400> SEQUENCE: 18
cctagtagat caaggtgaat tttactaatt actgcgatac aattgggatc agaaaatcta      60
ttgcatcggc agcaaatcca atcctcctgt cagcactctc tggggcaga ggtgacatat      120 tcccaccata cagatgcagt ggagctgcta cctcagtagg cagagttttc cccctatcag    180
tgtcattgtc catgtctttg atctcaagaa aatcagagat aatcaatatg ctaaccgcta    240
tctcaaacgg agtgtatggt aaaacttatt tactagtgcc tgattatatt gaagaggagt    300
tcgacacaca aaagattcga gtctttgaga tagggttcat caaacggtgg ctgaatgaca    360
tgccattact ccagacaacc aactatatgg tcctcccaga gaattcccaaa gctaaggtat    420 gtactatagc agtgggcgag ttgacactgg cttccttgtg tgtaggtgag agcaccgtgt    480
tgttatatca tgcacagcaat ggttcgcaag atagtatcct agcagtgacg ctgggaatat    540
ttggggcaac atctatggat caagttgaag aggtgatacc tgttgctcac ccatcagtag    600
aaaaaataca tataacaaat cac                                            623

<210> SEQ ID NO 19
<211> LENGTH: 866
<212> TYPE: DNA
<213> ORGANISM: canine distemper virus

<400> SEQUENCE: 19
gtttgatagg taaataacag tttccacttg attccctggg tgcaaatgac aacacatgag      60
ggaccacagt gaactggtct cctctacttg ctttgtttat caatccaaga attgttccat     120
tcttaggagg aatggtaagc catccggatt ccaaaagtgg gctttcataa taatccatac    180
catctccatt cagtataacc ggaccgtatg taaatgatat gttaagttta cggtcaatgc    240
ttgcatctag atgtaacgtc aaccgcccat aagatggcaa ctgtcctcct ccaaagggtt    300
cccatgatgt ttgattgcac atggggtagg attttctctg acaagccgac tccagacaat    360
tttcttgttc ctctaggttc tcagagacca atgcaggcac catccaggtt gctactgaat    420
cttttatgaa accacggtga tttgttatat gtattttttc gactgatggg tgagcgacag    480
gtatcacctc ttcgacttga tccataggtg ttgccccaaa gattcccagc gtcactacta    540
gaataccatc ttgtgaacca ttgctgtcat gatataataa tacagtgctc tcatctacac    600
acaaggaagc cagtgtcaac tcgcccactg ctatagtaca taccttggtt ttagaattct    660 ccggaggat catatagttg gttgtctgga ataatggcat gtcattcagc accttttga    720 tgaaccctat ctcaaagact cgaatctttt gcgtgtcgaa ctccccttca atataatcag    780
gcactagcaa ataagtttta ccatacactc cgtctgagat agaggtcagc atattgatta    840
tctctgatgt tcttgagatc aaagac                                         866
```

```
<210> SEQ ID NO 20
<211> LENGTH: 1134
<212> TYPE: DNA
<213> ORGANISM: canine distemper virus

<400> SEQUENCE: 20
aatgcttcct ttacccaccc tagtaagatc aagtaaattt tacggtaaat aaatagcgat      60
acaattggga tcagaaaatc tattgcatcg gcagcaaatc ctatccttt atcagcactc     120 tccggaggta gaggtgacat attcccacca tacaggtgca gtggagctac tacttcagta     180
ggcagagtct tccccctatc agtatcattg tccatgtctt tggtctcaag aacatctgaa     240
ataatcaata tgctaaccgc tatctcagac ggtgtgtatg gtaaaactta tttgctagtt     300
cctgattatc ttgaagggga gttcgacacg caaaagattc gagtctttga gatagggttc     360
atcaaacggt ggctgaacaa catgccatta ctccagacaa ccaactatat ggtcctcccg     420
gaggattcca agccaaggt atgtactata gcggtgggcg agttgacact ggcttccttg     480
tgtgtagatg agagcaccgt attgttatat catgacagca gtggttcaca agatggtatt     540
ctagtggtga cgctgggaat atttggggca cacctatgg atcaagttga gaggtgata     600 cctgttgctc acccatcagt agaaaaaata catatagcaa ccaccgtgg gttcatcaaa     660 gattcaatag caacctggat ggtgcctgca ttggtctctg agaaacaaga ggaacaaaaa     720
aattgtctgg agtcggcttg tcaaagaaaa tcctacccta tgtgcaacca aacgtcatgg     780 gaacccttg gaggaggaca gttgccatct tatgggcggt tgacattacc tctagatcaa     840
agcattgacc tccagcttaa catctcattt acatatggtc cggttatact gaatggagac     900
ggtatggatt attatgaaag tccgcttttg aactccggat ggcttaccat tcctcccaag     960
aacggaacag tccttggatt gataaacaaa gcaagtagag gagaccagtt cactgtatcc     1020
ccatgtgtga catttgcgcc cagggaatca gtggaattg tatttaccta ttcaaacatc     1080
ccagatatgg ataaagatgt ccttactgaa tccaaattag tggtgttgcc taac             1134

<210> SEQ ID NO 21
<211> LENGTH: 1124
<212> TYPE: DNA
<213> ORGANISM: canine distemper virus

<400> SEQUENCE: 21 accgggtgc ttaccccccc tagtaagatc aagtgaattt tacgaaaaac tgcgatccaa      60
ttgggatcag gaaatctatt gcaacggcag caaatcctat ccttttatca gcaccctccg     120
gaggtagagg tgacatattc ccatcataca gatgcagtgg agctactact tcagtaggca     180
gagtcttccc cctatcagta tcattgtcca tgtctttgat ctcaagaaca tctgaaataa     240
tcaatatgct aaccgctatc tcagacggag tgtatggtaa aacttatctg ctagttcctg     300
attatcttga aggggagttc gacacgcaaa agattcgagt ctttgagata gggttcatca     360
aacggtggct gaacaacatg ccattactcc agacaaccaa ctatatggtc ctcccagagg     420
attccaaagc caaggtatgt actatagcag tgggcgagtt gacactggct tccttgtgtg     480
tagatgagag caccatattg ttatatcatg acagcaatgg ttcacaagat ggtattctag     540
tggtgacgct gggaatattt ggggcaacac ctatggatca agttgaagag gtgatacctg     600
ttgctcaccc atcagtagaa aaatacata tagcaaacca tcgtgggttt atcaaagatt     660
caatagcaac ctggatggtg cctgcattgg tctctgagaa acaagaggaa caaaaaatt     720 gtctggagtc ggcttgtcaa agaaaatcct acccctatgtg caaccaaacg tcatgggaac     780
cctttggagg aggacagttg ccatcttatg ggcggttgac attacctcta gatccaagca     840
```

```
ttgaccttca gcttacatct catttacata cggcccgtta tactgaatgg agacggtatg      900
gatactatga aagcccactt ttagactccg gatggcttac cattcctcca agaacggaac      960
agtccttgga ttgataaaca aagcaagtag aggagaccag ttcactgtat ccccatgtgt     1020
tgacatttgc gccaggaatc agtggaaatt gttatttacc tattcaaact tcccaattat     1080
ggataagagt cctactggat ccaaattatg gtgtttccct aacc                      1124

<210> SEQ ID NO 22
<211> LENGTH: 1145
<212> TYPE: DNA
<213> ORGANISM: canine distemper virus

<400> SEQUENCE: 22
cattggtgca ttaacccacc tagtaagaca agtgaatttt actaatatac tgcgatacaa       60
ttgggatcag gaaatctatt gcatcggcag caaatcctat cctttttatca gcaccctccg     120 gaggtagagg tgacatattc ccatcataca gatgcagtgg agctactact tcagtaggca     180
gagtcttccc cctatcagta tcattgtcca tgtctttgat ctcaagaaca tctgaaataa     240
tcaatatgct aaccgctatc tcagacggag tgtatggtaa aacttatctg ctagttcctg     300
attatcttga aggggagttc gacacgcaaa agattcgagt ctttgagata gggttcatca     360
aacggtggct gaacaacatg ccattactcc agacaaccaa ctatatggtc ctcccagagg     420
attccaaagc caaggtatgt actatagcag tgggcgagtt gacactggct tccttgtgtg     480
tagatgagag caccatattg ttatatcatg acagcaatgg ttcacaagat ggtattctag     540
tggtgacgct gggaatattt ggggcaacac ctatggatca agttgaagag gtgatacctg     600
ttgctcaccc atcagtagaa aaatacata tagcaaacca tcgtgggttt atcaaagatt      660
caatagcaac ctggatggtg cctgcattgg tctctgagaa acaagaggaa caaaaaaatt      720
gtctggagtc ggcttgtcaa agaaaatcct accctatgtg caaccaaacg tcatgggaac      780
cctttggagg aggacagttg ccatcttatg gcggttgac attacctcta gatccaagca     840
ttgaccttca gcttaacatc tcatttacat acggtccggt tatactgaat ggagacggta     900
tggattacta tgaaagccca cttttagact ccggatggct taccattcct cccaagaacg     960
gaacagtcct tggattgata aacaaagcaa gtagaggaga ccagttcact gtaatccccc    1020
atgtgttgac atttgcgccc agggaatcaa gtggaaattg ttatttacct attccaaaca    1080
tcccagatta tggataaagg atgtccttac tgaagttcta aattagtggg ggtttgccct    1140
aagac                                                                1145

<210> SEQ ID NO 23
<211> LENGTH: 321
<212> TYPE: DNA
<213> ORGANISM: canine distemper virus

<400> SEQUENCE: 23
gcctcccagg ggcaccttcc cccccagta gctcaggtga atctcactta aaactgcgcc        60 cccctttggga tcttacaatc tattgcatcg gcagcaaatc cctccttttt atcagcactc     120
tcccgaggta gaggtgacat attcccacca taccgatgca atggagctac tatttcacta     180
ggcaagattt cccccctatc agtatcatta tctatgtctt tgatctcacg aacatcagag     240
ataatcaata tgctaaccgc tatctcatac ggagtgtatg gtaaaactta tttactaatg     300
cccgactata ttgaagggga g                                                321
```

```
<210> SEQ ID NO 24
<211> LENGTH: 1135
<212> TYPE: DNA
<213> ORGANISM: canine distemper virus

<400> SEQUENCE: 24
ttgatttcga ctccccgatt ttccactgtg cattaaccac ctagtaagat caaggtgaat        60
tttactgact ctggaacaaa tgggatcaag aaatttattg catggcagca aatcccatct       120
cctgtcagca ctctatgggg gcagaggtga catattccca ccatacaaga tgcagtggag       180
ctgctacctc agtaggcaga gttttccccc tatcagtgtc attggccatg tctttgacct       240
caagaaaatc agaggataat caatatgcta accgctatct caaaacggag tgtatggtaa       300
aacttattta ctagtgcctg attatattga agaggagttc gacacacaaa agattcgag       360 tctttgagat agggttcatc aaacggtggc tgaataacat gccattactc cagacaacta       420
actatatggt cctcccagag aattccaaag ctaaggtatg tactatagca gtgggcgagt       480
tgacactggc ttccttgtgt gtaggtgaga gcaccgtgtt gttatatcat gacagcaatg       540
gttcgcaaga tagtatccta gcagtgacgc tgggaatatt tggggcaaca tctatggatc       600
aagttgaaga ggtgatacct gttgctcacc catcagtaga aaaatacat ataacaaatc       660 accgtgggtt cataaaagat tcaatagcaa cctggatggt gcctgcattg gtctctgaga       720
aacaggaaga gcaaaaaaat tgtctggagt cggcttgtca agaaaatcc taccctatgt       780 gcaaccaaac gtcatgggaa ccttcggag gaggacagtt gccatcttat gggcggttga       840
cattacctct agatccaagc actgaccttc aacttaacat atcgtttacg tacggtccgg       900
ttatactgaa tggagacggt atggattatt atgaaagccc actgtcggac tccggatggc       960
ttaccattcc tcccaaaaac ggaacagtcc ttggattgat aaacaaagca agtagaggag      1020
atcagttcat tgtaatcccc catgtgttga catttgcgcc cagagaatca gtgggaatt       1080 gttatttacc tattcaaaca tcccatatta ggaaaaaggg aggcctaccc gggga            1135

<210> SEQ ID NO 25
<211> LENGTH: 796
<212> TYPE: DNA
<213> ORGANISM: canine distemper virus

<400> SEQUENCE: 25
tatggttcat tacccccggg cgtaagtgaa tttgaatcgt agtaattgct gtgataaaat        60
tgggattgga aatgtattgc attgttatga aattctacct tttcagcact tgcctccgtt       120
ggttgagggg acttattccc atcatacata tgcagtggag ctactacctc atccggcaga       180
gttatatttg atcatcatta ttgcacatgt ttgtgaccta aaaaacatct ggcatatgca       240
atctgctaac cgcgatctca tgtggagtgt atggcaaaac ttatctgcta cttcctgatt       300
ttcttgaagg ggagtccgac actctgccga tgtccgacaa gctgatcggg ttcatcaaac       360
tctggctgaa caacatgttg cgcgtctgac aacctccgat ttggcctgcc cagaggattt       420
tacagccaag gtatgtacca tatcccaggg gaacttcaca ctgccttcct tgtgtgttag       480
ccagagcccc atattgtccc ataatgatat gaatgtccta caagaggtca ttttccatgt       540
gaccccgcgt tcatttgtgg caatggcggt ggttcaattg aacagggta tatctgaccc       600 tatctttcac tagagaaatt acatatgaca accatcatg gcttgatcaa agaataactt       660
cctttctggc tgacgcttga cttgcccta tatataccat attttcttaa taaatcgcgg       720
tcaattgcct gtggagccaa attttaccac tcttccaacc ttatgttacg ggctttcctt       780
gccggaggac cgttgc                                                        796
```

<210> SEQ ID NO 26
<211> LENGTH: 1122
<212> TYPE: DNA
<213> ORGANISM: canine distemper virus

<400> SEQUENCE: 26

```
gcgattttgc cctgtgcatt aacccaccta gtaagatcaa ggtaaatttt actaaattct      60
gcgaaacatg tggatcagaa atctatggc atcggcagca atcccatcct cctgcagccc     120
tcttggggca gaggtgacat attcccacca tacagatgca gtgaggctgc tacctcagta     180
ggccagagtt ttccctatc agggtcattg tgcatgtctt tgacctcaag aaagtcagag      240
ataatcaaat atgctaaccc gctatctcaa acggagtgta tgggaaaaac ttatttacta     300
gtgcctggat tatattgaag aggagttcga cacacaaaag attcgagtct ttgagatagg     360
gttcatcaaa cggtggctga ataacatgcc attactccag acaactaact atatggtcct     420
cccagagaat tccaaagcta aggtatgtac tatagcagtg ggcgagttga cactggcttc     480
cttgtgtgta ggtgagagca ccgtgttgtt atatcatgac agcaatggtt cgcaagatag     540
tatcctagca gtgacgctgg gaatatttgg ggcaacatct atggatcaag ttgaagaggt     600
gatacctgtt gctcacccat cagtagaaaa aatacatata acaaatcacc gtgggttcat     660
aaaagattca atagcaacct ggatggtgcc tgcattggtc tctgagaaac aggaagagca     720
aaaaaattgt ctggagtcgg cttgtcaaag aaaatcctac cctatgtgca accaaacgtc     780
atgggaaccc ttcggaggag acagttgcc atcttatggg cggttgacat acctctaga      840
tccaagcact gaccttcaac ttaacatatc gtttacatac ggtccggtta tactgaatgg     900
agacggtatg gattattatg aaagcccact gtcggactcc ggatggctta ccattcctcc     960
caaaaacgga acagtccttg gattgataaa caaagcaagt agaggagatc agttcattgt    1020
aatcccccat gtgttaacat tgcgcccag agaatcaagt gggggattgt tattttccta     1080
ttcaaacatg cccatattat gataaaggat ggccttaacc cg                       1122
```

<210> SEQ ID NO 27
<211> LENGTH: 798
<212> TYPE: DNA
<213> ORGANISM: canine distemper virus

<400> SEQUENCE: 27

```
agttcgacgc acaaaagatt cgagtgttga gatagggttg atcggacgag gaggtgaagg      60
acatgccatt actccagaca gctaactata tggtccgccc agagaattcc aaagctaagg    120
tatgtactat agcagtgggc gaggtggcac tggcttcctt gtgtgtaggg gagagcgccg    180
tgttgttata tcatggcagc aatggttcgc aagatagtat cgtagcagtg acgctgggaa    240
tatttggggc aacatctatg gatcaagttg aagaggtgat acctgttgct cacccatcag    300
tagagaaaat acatatagca aatcaccgtg ggttcataaa agattcaata gcaacctgga    360
tggtgcctgc attggtctct gagaaacagg aagagcaaaa aattgtctg gagtcggctt     420
gtcaaagaaa atcctaccgt atgtgcagcc aaacggcatg gaacccttc ggaggaggac     480
agttgccatc ttatgggcgg ttgacattac ctctagatcc aagcgctgcc ttcaacttaa    540
catatcgttt acatacggtc cggttatact gaatggagac ggtatggatt attatgaaag    600
cccactgtcg ggctccggat ggcttgccat tcctcccaaa aacggaacag tccttggatt    660
gataaacaaa gcaagtagag gagatcagtt cattgtaatc ccccatgtgt ggacatttgc    720
gcccagagaa tcaagtgggg gattgttttt taaactatgc aaacggcgca tatgaggggg    780
```

```
gagggggggc gggaggct                                                    798

<210> SEQ ID NO 28
<211> LENGTH: 1035
<212> TYPE: DNA
<213> ORGANISM: canine distemper virus

<400> SEQUENCE: 28
cagtgagagc aaaaatgtag gaaagggcag gaattccatg ctcaaggagc ggatgtgggg     60
agaggttgcg agtcccgcca gcagtgcagg aagggggtact cagtagcggg gtttcccccct   120 aggaggggga ttgtccagtc tttgatatca gaaaagaagg atatcaatat gctaaccgct    180
atcgccaaag gagggtatgg taagagctta ttgggagtgc ctgattagag ggagggaagt    240
tctacaggag agagattgga gtggtgagat gggggttcgt caagcggtgg atgaatgaca    300
taccattact ccagacaacc aagtataggg gcctcccaga gaatgccaaa gctaaggtat    360
gtactatagc agtgggcgag ttcgctggc ttccttgtgt gtaggtgaga cgccgtgtt     420 gttatatcat gacagcaatg gttcgcaaga tagtatccta gctgtgacgc tgggaatatt    480
tggggcagca tctatggatc aagttgaaga ggtgatgcct gttgctcacc catcagtaga    540
aaaaatacat ataacaaatc gccgtgggtt cataaaagat tcaatagcag catggatggt    600
gcctgcattg gtctctgaga agcaggaaga gcaaaaaaat tgtcaggagt cgggttgtca    660
aagaaaatcc tacccgatgt gcaaccaaac gtcatgggaa cccttcggag gaggacaggt    720
gccatcttat gggcggttgg cattacctct agagccaagc actggccttc aacttgacat    780
atcgtttaca tacgggccgg ttatactgaa tgagacggt atggattatt atgaaagccc     840
actgtcggac gccggatggc ttaccattcc tcccaaaaac ggaacagtcc gtggattgat    900
aaacaaagca agtagaggag gccagttcat tgtaatcccc catgtgttga catttgcgcc    960
cagggaatca gtgggaatt gctattttcc tattcagaac acccccagatt aggatagaag   1020 gaggggcctg ggccg                                                   1035

<210> SEQ ID NO 29
<211> LENGTH: 1131
<212> TYPE: DNA
<213> ORGANISM: canine distemper virus

<400> SEQUENCE: 29
cttgtgggct taaaccacct agtaatacaa agtgaatttt actaattact gcgatacaat     60
tgggatcaaa aaatctattg catcggcagc aaatcctatc cttttatcag cactctccgg    120
aggcagaggt gacatattcc caccatacag atgcagtgga gctactactt cagtaggcag    180
agtcttcccc ttatcagtat cattgtccat gtctttgatc tcaagaacat ctgaaataat    240
caatatgcta accgctatct cagacggagt gtatggtaaa acttatttgc tagttcctga    300
ttatcttgaa ggggagttcg acacgccgaa gattcgagtc tttgagatag ggttcatcaa    360
acggtggctg aacaacatgc cattaatcca gacaaccaac tatatggtcc tcccggagga    420
ttccaaagct aaggtatgta ctatagcagt gggcgagttg acactggctt ccttatgtgt    480
agatgagagc accgtattgt tatatcatga cagcaatggt tcacaagatg gtattctagt    540
ggtgacgctg gaatatttg gggcaacacc tatggatcga gttgaagagg tgatacctgt    600
tgctcacccg tcagtagaaa aaatacatat ggcaaaccac cgtgggttca tcaaagattc    660
aatagcaacc tggatggtgc ctgcattggt tctctgagaaa caagaggaac aaaaaaattg    720
tctggagtcg gcttgtcaaa gaaaatccct accctatgtg caaccaaacg tcatgggaaa    780
```

| | | | |
|---|---|---|---|
| cccctttggag | gaggacagtt | gccatcttat | gggcggttga | cattacctct | agatccaagc | 840 |
| attgaccttc | accttaacat | ctcatttaca | tacggcccag | ttatactgaa | tggggacggt | 900 |
| atggattatt | atgaaagccc | acttttggac | tccggatggc | ttaccattcc | tcccaagaac | 960 |
| ggaacagtcc | ttggattgat | aaacagagca | gtagaggaga | acagttcact | gtaatcccca | 1020 |
| tgtgttgact | tgcgcaaggg | gatcaagtgg | aaattgtatt | tacctattca | aacatcttaa | 1080 |
| attatggata | aagatgccct | caccgagccc | aaattagtgg | tgttgcctca | t | 1131 |

<210> SEQ ID NO 30
<211> LENGTH: 759
<212> TYPE: DNA
<213> ORGANISM: canine distemper virus

<400> SEQUENCE: 30

| | | | |
|---|---|---|---|
| ctccctttcg | gcttgaacat | gtatccggct | cttgggttgc | atgagttttc | cggggagtta | 60 |
| acaaccattg | aatcccttat | gatgctatat | caacagatgg | gtgaaacagc | accgtacatg | 120 |
| gttattctgg | aaaattctgt | ccagaacaaa | tttagtgcag | atcctaccc | attgctctgg | 180 |
| agttatgcta | tgggagttgg | tgttgaactt | gaaaactcta | tggagggtt | aaatttcggt | 240 |
| agatcctact | ttgacccagc | ttatttcagg | ctcgggcaag | aaatggttag | aagatcggcc | 300 |
| ggtaaggtaa | gctctgcact | tgccgccgag | cttggcatca | ccaaggaaga | ggctcagcta | 360 |
| gtgtcagaaa | tagcatccaa | gacaacagag | gacccgcatt | tggcattgaa | actatgtatc | 420 |
| cggctcttgg | gttgcatgag | ttttccgggg | agttaacaac | cattgaatcc | cttgtgatgc | 480 |
| tttaccacca | aatgggtgaa | ggacccccca | tggttattct | tggaaaattt | gtccgacaaa | 540 |
| attagtgcag | gatctaccat | tgctctggag | ttatgctatg | ggagttggtg | gtgaacttga | 600 |
| aaacccccatg | ggggggttaa | atttcggcag | attcttcttt | gacagttaat | tttaggctcg | 660 |
| gccagaaaat | ggttagaaaa | ctcggccggt | taggggaaag | ctttgtcttt | gcccgcttgg | 720 |
| gttcccccc | cgaaaggttt | cccccctttt | ctatatatt | | | 759 |

<210> SEQ ID NO 31
<211> LENGTH: 1132
<212> TYPE: DNA
<213> ORGANISM: canine distemper virus

<400> SEQUENCE: 31

| | | | |
|---|---|---|---|
| tgtgaatgtg | aacttccgcg | atctccactg | gtgcattaac | ccactagtaa | gatcaaggtg | 60 |
| aatttactaa | ctacgcgata | caattgggat | cagaaaatct | attgcatcgg | cagcaaatcc | 120 |
| catcctcctg | tcagcactct | ctgggggcag | aggtgacata | ttcccaccat | accgatgcag | 180 |
| tggagctgct | acctcagtag | gcagagtttt | ccccctgtca | gtgtcattgt | ccatgtcttt | 240 |
| gatctcaaga | aaatcagaga | taatcaatat | gctaaccgct | atctcaaacg | gagtgtatgg | 300 |
| taaaacttat | ttactagtgc | ctgattatat | tgaagaggag | ttcgacacac | aaaagattcg | 360 |
| agtctttgag | atagggttca | tcaaacggtg | gctgaatgac | atgccattac | tccagacaac | 420 |
| caactatatg | gtcctcccag | agaattccaa | agctaaggta | tgtactatag | cagtgggcga | 480 |
| gttgacactg | gcttccttgt | gtgtaggtga | gagcaccgtg | tcattatatc | atgacagcaa | 540 |
| tggttcgcaa | gatagtatcc | tagcagtgac | gctggggaata | tttggggcaa | catctatgga | 600 |
| tcaagttgaa | gaggtgatac | ctgttgctca | cccatcagta | gaaaaaatac | atataacaaa | 660 |
| tcaccgtggg | ttcataaaag | attcaatagc | aacctggatg | gtgcctgcat | tggtctctga | 720 |
| gaaacaggaa | gagcaaaaaa | attgtctgga | gtcggcttgt | caaagaaaat | cctaccctat | 780 |

```
gtgcaaccaa acgtcatggg aacccttcgg aggaggacag ttgccatctt atgggcggtt 840
gacattacct ctagatccaa gcactgacct tcaacttaac atatcgttta catacggtcc 900
ggttatactg aatggagacg gtatggatta ttatgaaagc ccactgtcgg actccggatg 960
gcttaccatt cctcccaaaa acggaacagt ccttggattg ataaacaaag caagtagagg 1020
agaccagttc attgtaatcc cccatgtgtt gacatttgcg cccagggaat caagtgggaa 1080
ttgttattta cctattcaaa catcccagat tatgaaaaga tgccttaacc cg 1132
```

<210> SEQ ID NO 32
<211> LENGTH: 1127
<212> TYPE: DNA
<213> ORGANISM: canine distemper virus

<400> SEQUENCE: 32

```
tctgctgctt aaccacctag taagatcagg tgaattttac taactactgc gatacaattg 60
ggatcagaaa atctattgca tcggcagcaa atcccatcct cctgtcagca ctctctgggg 120
gcagaggtga catattccca ccataccgat gcagtggagc tgctacctca gtaggcagag 180
ttttcccct gtcagtgtca ttgtccatgt ctttgatctc aagaaaatca gagataatca 240
atatgctaac cgctatctca aacggagtgt atggtaaaac ttatttacta gtgcctgatt 300
atattgaaga ggagttcgac acacaaaaga ttcgagtctt tgagataggg ttcatcaaac 360
ggtggctgaa tgacatgcca ttactccaga caaccaacta tatggtcctc ccagagaatt 420
ccaaagctaa ggtatgtact atagcagtgg gcgagttgac actggcttcc ttgtgtgtag 480
gtgagagcac cgtgtcatta tatcatgaca gcaatggttc gcaagatagt atcctagcag 540
tgacgctggg aatatttggg gcaacatcta tggatcaagt tgaagaggtg aacctgttgc 600
tcacccatca gtagaaaaaa tacatataac aaatcaccgt gggttcataa aagattcaat 660
agcaactgga tggtgcctgc attggtctct gagaaacagg aagagcaaaa aaattgtctg 720
gagtcggctt gtcaaagaaa atcctaccct atgtgcaacc aaacgtcatg ggaacccttc 780
ggaggaggac agttgccatc ttatgggcgg ttgacattac ctctagatcc aagcactgac 840
cttcaactta acatatcgtt tacatacggt ccggttatac tgaatggaga cggtatggat 900
tattatgaaa gcccactgtc ggactccgga tggcttacca ttcctcccaa aaacggaaca 960
gtccttggat tgataaacaa agcagtagag gagaccagtt cattgtaatc ccccatgtgt 1020
tgacatttgc gcccagggaa tcaagtggga attgttattt acctattcaa acatccagat 1080
tatggataaa gatgtcctta ctgagtccaa attagtgtgt gtgccta 1127

<210> SEQ ID NO 33
<211> LENGTH: 1128
<212> TYPE: DNA
<213> ORGANISM: canine distemper virus
<400> SEQUENCE: 33
attggttgcc cttaacccac ctagtaagat caggtgaatt ttactaacta ctgcgataca 60
attgggatca gaaaatctat tgcatcggca gcaaatccca tcctcctgtc agcactctct 120
gggggcagag gtgacatatt cccaccatac cgatgcagtg gagctgctac ctcagtaggc 180
agagttttcc ccctgtcagt gtcattgtcc atgtctttga tctcaagaaa atcagagata 240
atcaatatgc taaccgctat ctcaaacgga gtgtatggta aaacttattt actagtgcct 300
gattatattg aagaggagtt cgacacacaa aagattcgag tctttgagat agggttcatc 360
aaacggtggc tgaatgacat gccattactc cagacaacca actatatggt cctcccagag 420

-continued

```
aattccaaag ctaaggtatg tactatagca gtgggcgagt tgacactggc ttccttgtgt    480
gtaggtgaga gcaccgtgtc attatatcat gacagcaatg gttcgcaaga tagtatccta    540
gcagtgacgc tgggaatatt tggggcaaca tctatggatc aagttgaaga ggtgataacct   600
gttgctcacc catcagtaga aaaaatacat ataacaaatc accgtgggtt cataaaagat    660
tcaatagcaa cctggatggt gcctgcattg gtctctgaga acaggaaga gcaaaaaaat     720
tgtctggagt cggcttgtca agaaaatcc taccctatgt gcaaccaaac gtcatgggaa     780
cccttcggag gaggacagtt gccatcttat gggcggttga cattacctct agatccaagc    840
actgacccttc aacttaacat atcgtttaca tacggtccgg ttatactgaa tggagacggt   900
atggattatt atgaaagccc actgtcggac tccggatggc ttaccattcc tcccaaaaac    960
ggaacagtcc ttgaatgata acaaagcaa gtagaggaga ccagtttatt gtactccctc    1020
tgtgtttgac atttgcgccc aggatcaagt ggcattgttt ctacctatcc aaacttccga   1080
attatgata aagatgtcct tactgatcca aactagtgcg ttgctcaa                 1128
```

<210> SEQ ID NO 34
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 34
atttgggatt gcttagga                                                   18

<210> SEQ ID NO 35
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 35
ggcgctcatc ttggacat                                                   18

<210> SEQ ID NO 36
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 36
gttagctagt ttcatcct                                                   18

<210> SEQ ID NO 37
<211> LENGTH: 18
<212> TYPE: DNA
<213> ORGANISM: Artificial Sequence
<220> FEATURE:
<223> OTHER INFORMATION: Synthetic oligonucleotide primer

<400> SEQUENCE: 37
ggtcctctgt tgtcttgg                                                   18

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide primer

<400> SEQUENCE: 38
gaattcgact tccgcgatct cc 22

<210> SEQ ID NO 39
<211> LENGTH: 25
<212> TYPE: DNA
<213> ORGANISM: Artificial Sequence
<220> FEATURE:
<223> OTHER INFORMATION: Synthetic oligonucleotide primer

<400> SEQUENCE: 39
taggcaacac cactaatttr gactc 25

<210> SEQ ID NO 40
<211> LENGTH: 23
<212> TYPE: DNA
<213> ORGANISM: Artificial Sequence
<220> FEATURE:
<223> OTHER INFORMATION: Synthetic oligonucleotide primer

<400> SEQUENCE: 40
tcgaaatcct atgtgagatc act 23

<210> SEQ ID NO 41
<211> LENGTH: 26
<212> TYPE: DNA
<213> ORGANISM: Artificial Sequence
<220> FEATURE:
<223> OTHER INFORMATION: Synthetic oligonucleotide primer

<400> SEQUENCE: 41
atgctggaga tggtttaatt caatcg 26

<210> SEQ ID NO 42
<211> LENGTH: 1824
<212> TYPE: DNA
<213> ORGANISM: canine distemper virus

<400> SEQUENCE: 42
atgctctcct accaagacaa ggtgggtgcc ttctataagg ataatgcaag agctaattca 60
tccaagctgt ccctagtgac agaagagcaa gggggcagga gaccacccta tttgctgttt 120
gtccttctca tcctactggt tggaatcctg gccttgcttg ctatcactgg agttcgattt 180
caccaagtat caactagcaa cgtggaattt agcagattgc taaaagagga tatggagaaa 240
tcagaggctg tacatcacca agtcatagat gttttgacgc cgctcttcaa aattattgga 300
gatgagattg ggttacggct gccacaaaaa ctaaacgaga tcaaacaatt catccttcaa 360
aagacaaact tcttcaatcc taacagggaa ttcgacttcc gtgatctcca ctggtgcatt 420
aacccaccta gtaagatcaa ggtgaatttt actaactact gcgatacaat tgggatcaga 480
aaatctattg catcggcagc aaatcccatc ctcctgtcag cactctctgg gggcagaggt 540
gacatattcc caccataccg atgcagtgga gctgctacct cagtaggcag agttttcccc 600
ctgtcagtgt cattgtccat gtctttgatc tcaagaaaat cagagataat caatatgcta 660
accgctatct caaacggagt gtatggtaaa acttatttac tagtgcctga ttatattgaa 720
gaggagttcg acacacaaaa gattcgagtc tttgagatag ggttcatcaa acggtggctg 780
aatgacatgc cattactcca gacaaccaac tatatggtcc tcccagagaa ttccaaagct 840
aaagtatgta ctatagcagt gggcgagttg acactggctt ccttgtgtgt aggtgagagc 900
accgtgtcat tatatcatga cagcaatggt tcgcaagata gtatcctagc agtgacgctg 960

```
ggaatatttg gggcaacatc tatggatcaa gttgaagagg tgatacctgt tgctcaccca   1020
tcagtagaaa aaatacatat aacaaatcac cgtgggttca taaaagattc aatagcaacc   1080
tggatggtgc ctgcattggt ctctgagaaa caggaagagc aaaaaaattg tctggagtcg   1140
gcttgtcaaa gaaatccta ccctatgtgc aaccaaacgt catgggaacc cttcggagga   1200
ggacagttgc catcttatgg gcggttgaca ttacctctag atccaagcac tgaccttcaa   1260
cttaacatat cgtttacata cggtccggtt atactgaatg gagacggtat ggattattat   1320
gaaagcccac tgtcggactc cggatggctt accattcctc ccaaaaacgg aacagtcctt   1380
ggattgataa acaaagcaag tagaggagac cagttcattg taatccccca tgtgttgaca   1440
tttgcgccca gggaatcaag tgggaattgt tatttaccta ttcaaacatc ccagattatg   1500
gataaagatg tccttactga gtccaattta gtggtgttgc ctacacagaa ttttagatat   1560
gtcatagcaa catatgatat atcccgggac aatcatgcga tcgtttacta tgtctatgac   1620
ccaattcgga cgatttctta tacgtaccca tttagactaa ctaccaaagg tagacctgat   1680
ttcctaagga ttgaatgttt tgtttgggat gatgatttgt ggtgtcacca gttctaccga   1740
ttcgaggctg acatcactaa ctctaccacc agtgttgaga atttagtccg tataagattc   1800
tcatgtaacc gttcaagacc ttga                                          1824
```

<210> SEQ ID NO 43
<211> LENGTH: 1824
<212> TYPE: DNA
<213> ORGANISM: canine distemper virus

<400> SEQUENCE: 43

```
atgctctcct accgagacaa ggtgggtgcc ttctataagg acaatgctag agctaattca     60
tccaagctgt ccttagtgac agaagagcaa gggggcagga gaccacccta tttgctgttt    120
gtccttctca tcctactggt tggaatcatg gccttgcttg ctatcactgg agttcgattt    180
caccaagtat caactagcaa tatggagttt agcagattgc tgaaagagga tctggagaaa    240
tcagaggccg tacatcacca agtcatagat gtcttgacgc cgctcttcaa aattattgga    300
gatgagattg ggttacggtt gccacaaaaa ctaaacgaga tcaaacaatt tatccttcaa    360
aagacaaact tcttcaatcc gaacagggaa ttcgacttcc gcgatctcca ctggtgcatt    420
aacccaccta gtaagatcaa ggtgaatttt actaattact gcgatactat ggggatcaga    480
aaatctattg catcggcagc aaatcccatc cttttatcag cactctccgg aggtagaggt    540
gacatattcc caccatacag atgcaatgga gctactattt cagtaggcaa gattttcccc    600
ctatcagtat cattatctat gtctttgatc tcaagaacat cagagataat caatatgcta    660
accgctatct cagacggagt gtatggtaaa acttatttac taatgcctga ttatattgaa    720
ggggagttcg acacgcaaaa gattcgagtc tttgagatag ggttcatcaa acggtggctg    780
aatgacatgc cattactcca gacaaccaac tatatggtcc tcccagagaa ttccaaagct    840
aaggtatgta ctatagcagt gggcgagttg acactggctt ctttgtgtgt aggtgagagc    900
accgtattgt tatatcatga cagcaatggt tcacaagatg gtattctagt agtgacgctg    960
ggaatattcg gggcaacatc tatggatcaa gttgaagagg tgatacctgt cgctgaccca   1020
ttagtagaaa aaatacatat aacaaatcac cgcgggatca taaaagattc aatagcaacc   1080
tggatggtgc ctgcattagt ttctgagaaa caagaggaac aaaaaaattg tctggagtca   1140
gcttgtcaaa gaaatccta ccctatgtgc aatcaaacgt catgggaacc ctttggagga   1200
ggacagttgc catcttatgg gcggttgaca ttacctctag atccaagcat tgaccttcaa   1260
```

```
cttaacatat catttacata cggtccgatt atactgaatg gggacggtat ggattattat    1320
gagagcccac tgttggactc cggatggctt accattcctc ccaagaacgg aacagtcctt    1380
ggattgataa acaaagcaag tagaggagac cagttcactg taatcccca tgtgttgaca     1440 tttgcgccca gggaatcaag tggaaattgt tatttaccta ttcaaacatc ccagattatg    1500
gataaagatg tccttactga gtccaattta gtggtgttgc ctacacagaa ttttagatat    1560
gtcgtagcaa catatgatat atctcgggac gatcatgcga ttgtttatta tgtttatgac    1620
ccaatacgga cgatttctta tacgtaccca tttagactaa ctactaaggg tagacctgat    1680
ttcttaagga ttgagtgttt tgtgtgggat gacgatttgt ggtgtcacca gttttaccga    1740
ttcgaggccg acatcaccaa ctctacaacc agtgtcgaga atttagtccg tatgagattc    1800
tcatgtaacc gttccagacc ttga                                           1824

<210> SEQ ID NO 44
<211> LENGTH: 607
<212> TYPE: PRT
<213> ORGANISM: canine distemper virus

<400> S

Val Leu Pro Glu Asn Ser Lys Ala Lys Val Cys Thr Ile Ala Val Gly
            275                 280                 285

Glu Leu Thr Leu Ala Ser Leu Cys Val Gly Glu Ser Thr Val Ser Leu
    290                 295                 300

Tyr His Asp Ser Asn Gly Ser Gln Asp Ser Ile Leu Ala Val Thr Leu
305                 310                 315                 320

Gly Ile Phe Gly Ala Thr Ser Met Asp Gln Val Glu Glu Val Ile Pro
                325                 330                 335

Val Ala His Pro Ser Val Glu Lys Ile His Ile Thr Asn His Arg Gly
            340                 345                 350

Phe Ile Lys Asp Ser Ile Ala Thr Trp Met Val Pro Ala Leu Val Ser
    355                 360                 365

Glu Lys Gln Glu Glu Lys Asn Cys Leu Glu Ser Ala Cys Gln Arg
370                 375                 380

Lys Ser Tyr Pro Met Cys Asn Gln Thr Ser Trp Glu Pro Phe Gly Gly
385                 390                 395                 400

Gly Gln Leu Pro Ser Tyr Gly Arg Leu Thr Leu Pro Leu Asp Pro Ser
                405                 410                 415

Thr Asp Leu Gln Leu Asn Ile Ser Phe Thr Tyr Gly Pro Val Ile Leu
            420                 425                 430

Asn Gly Asp Gly Met Asp Tyr Tyr Glu Ser Pro Leu Ser Asp Ser Gly
    435                 440                 445

Trp Leu Thr Ile Pro Pro Lys Asn Gly Thr Val Leu Gly Leu Ile Asn
450                 455                 460

Lys Ala Ser Arg Gly Asp Gln Phe Ile Val Ile Pro His Val Leu Thr
465                 470                 475                 480

Phe Ala Pro Arg Glu Ser Ser Gly Asn Cys Tyr Leu Pro Ile Gln Thr
                485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Ile Ala Thr Tyr Asp Ile Ser
    515                 520                 525

Arg Asp Asn His Ala Ile Val Tyr Tyr Val Tyr Asp Pro Ile Arg Thr
530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Ile Arg Phe Ser Cys Asn Arg Ser Arg Pro
    595                 600                 605

<210> SEQ ID NO 45
<211> LENGTH: 607
<212> TYPE: PRT
<213> ORGANISM: canine distemper virus

<400> SEQUENCE: 45

Met Leu Ser Tyr Arg Asp Lys Val Gly Ala Phe Tyr Lys Asp Asn Ala
1               5                   10                  15

Arg Ala Asn Ser Ser Lys Leu Ser Leu Val Thr Glu Glu Gln Gly Gly
            20                  25                  30

Arg Arg Pro Pro Tyr Leu Leu Phe Val Leu Leu Ile Leu Leu Val Gly
        35                  40                  45

-continued

```
Ile Met Ala Leu Leu Ala Ile Thr Gly Val Arg Phe His Gln Val Ser
    50                  55                  60
Thr Ser Asn Met Glu Phe Ser Arg Leu Leu Lys Glu Asp Leu Glu Lys
 65                  70                  75                  80
Ser Glu Ala Val His His Gln Val Ile Asp Val Leu Thr Pro Leu Phe
                 85                  90                  95
Lys Ile Ile Gly Asp Glu Ile Gly Leu Arg Leu Pro Gln Lys Leu Asn
                100                 105                 110
Glu Ile Lys Gln Phe Ile Leu Gln Lys Thr Asn Phe Asn Pro Asn
            115                 120                 125
Arg Glu Phe Asp Phe Arg Asp Leu His Trp Cys Ile Asn Pro Pro Ser
    130                 135                 140
Lys Ile Lys Val Asn Phe Thr Asn Tyr Cys Asp Thr Met Gly Ile Arg
145                 150                 155                 160
Lys Ser Ile Ala Ser Ala Ala Asn Pro Ile Leu Leu Ser Ala Leu Ser
                165                 170                 175
Gly Gly Arg Gly Asp Ile Phe Pro Pro Tyr Arg Cys Asn Gly Ala Thr
                180                 185                 190
Ile Ser Val Gly Lys Ile Phe Pro Leu Ser Val Ser Leu Ser Met Ser
            195                 200                 205
Leu Ile Ser Arg Thr Ser Glu Ile Ile Asn Met Leu Thr Ala Ile Ser
    210                 215                 220
Asp Gly Val Tyr Gly Lys Thr Tyr Leu Leu Met Pro Asp Tyr Ile Glu
225                 230                 235                 240
Gly Glu Phe Asp Thr Gln Lys Ile Arg Val Phe Glu Ile Gly Phe Ile
                245                 250                 255
Lys Arg Trp Leu Asn Asp Met Pro Leu Leu Gln Thr Thr Asn Tyr Met
            260                 265                 270
Val Leu Pro Glu Asn Ser Lys Ala Lys Val Cys Thr Ile Ala Val Gly
    275                 280                 285
Glu Leu Thr Leu Ala Ser Leu Cys Val Gly Glu Ser Thr Val Leu Leu
290                 295                 300
Tyr His Asp Ser Asn Gly Ser Gln Asp Gly Ile Leu Val Val Thr Leu
305                 310                 315                 320
Gly Ile Phe Gly Ala Thr Ser Met Asp Gln Val Glu Glu Val Ile Pro
                325                 330                 335
Val Ala Asp Pro Leu Val Glu Lys Ile His Ile Thr Asn His Arg Gly
            340                 345                 350
Ile Ile Lys Asp Ser Ile Ala Thr Trp Met Val Pro Ala Leu Val Ser
    355                 360                 365
Glu Lys Gln Glu Glu Lys Asn Cys Leu Glu Ser Ala Cys Gln Arg
370                 375                 380
Lys Ser Tyr Pro Met Cys Asn Gln Thr Ser Trp Glu Pro Phe Gly Gly
385                 390                 395                 400
Gly Gln Leu Pro Ser Tyr Gly Arg Leu Thr Leu Pro Leu Asp Pro Ser
                405                 410                 415
Ile Asp Leu Gln Leu Asn Ile Ser Phe Thr Tyr Gly Pro Ile Ile Leu
            420                 425                 430
Asn Gly Asp Gly Met Asp Tyr Tyr Glu Ser Pro Leu Leu Asp Ser Gly
    435                 440                 445
Trp Leu Thr Ile Pro Pro Lys Asn Gly Thr Val Leu Gly Leu Ile Asn
450                 455                 460
Lys Ala Ser Arg Gly Asp Gln Phe Thr Val Ile Pro His Val Leu Thr
465                 470                 475                 480
```

-continued

```
Phe Ala Pro Arg Glu Ser Ser Gly Asn Cys Tyr Leu Pro Ile Gln Thr
            485                 490                 495

Ser Gln Ile Met Asp Lys Asp Val Leu Thr Glu Ser Asn Leu Val Val
            500                 505                 510

Leu Pro Thr Gln Asn Phe Arg Tyr Val Val Ala Thr Tyr Asp Ile Ser
            515                 520                 525

Arg Asp Asp His Ala Ile Val Tyr Tyr Val Tyr Asp Pro Ile Arg Thr
            530                 535                 540

Ile Ser Tyr Thr Tyr Pro Phe Arg Leu Thr Thr Lys Gly Arg Pro Asp
545                 550                 555                 560

Phe Leu Arg Ile Glu Cys Phe Val Trp Asp Asp Leu Trp Cys His
                565                 570                 575

Gln Phe Tyr Arg Phe Glu Ala Asp Ile Thr Asn Ser Thr Thr Ser Val
            580                 585                 590

Glu Asn Leu Val Arg Met Arg Phe Ser Cys Asn Arg Ser Arg Pro
            595                 600                 605
```

IMMUNOGENIC COMPOSITIONS, VACCINES AND DIAGNOSTICS BASED ON CANINE DISTEMPER VIRUSES CIRCULATING IN NORTH AMERICAN DOGS

CROSS-REFERENCE TO RELATED APPLICATIONS

This application claims benefit of U.S. provisional patent application 61/148,791, filed Jan. 30, 2009, the complete contents of which is hereby incorporated by reference.

BACKGROUND OF THE INVENTION

1. Field of the Invention

The invention generally relates to newly identified isolates of canine distemper virus (CDV). In particular, the invention provides improved CDV immunogenic compositions, vaccines and diagnostics that contain or take into account these newly discovered isolates, and describes a systematic protocol for selecting, based on genetic makeup, broad spectrum isolates for use in immunogenic compositions, vaccines and diagnostics.

2. Background of the Invention

Canine distemper virus (CDV) is a single-stranded RNA Morbillivirus that affects dogs of all ages. CDV causes a multi-systemic infection that may involve the ocular, respiratory, gastrointestinal, integument and nervous systems, and is usually rapidly fatal. While the disease is a devastating problem for dogs, other species are also susceptible to the virus, for example, raccoons, foxes, coyotes, wolves, various fur-producing animals, and large non-domestic cats such as lions, leopards, cheetahs, and tigers. In the past, vaccines have proven to be effective in reducing the incidence of CDV infection. However, there appears to be a resurgence of the incidence of CDV, even in fully vaccinated animals.

The hemagglutinin (H) protein of CDV is a viral surface protein that is involved in host cell-virus binding, and mutations in the protein affect host cell-virus interactions. H protein is considered to be a virulence factor for CDV. The H protein displays significant (e.g. about 10%) variation in amino acid sequence among CDV isolates, and phylogenetic analysis of this variation serves as the basis for the division of viral isolates into seven lineages: American-1, American-2, Arctic-like, Asia-1, Asia-2, Europe, and European wildlife (McCarthy, A. J., M. A. Shaw, and S. J. Goodman. 2007. Proc. Biol. Sci. 274:3165-3174). Antibodies to H protein provide protection against infection, and are thus the likely basis for vaccine efficacy. However, antibodies do not necessarily cross-react between lineages. Hence, vaccines based on a particular isolate may or may not provide the vaccine recipient with protection against infection with other isolates. This is particularly problematic given 1) the high rate of mutation exhibited by RNA viruses such as CDV and 2) the increase in the global transport of dogs from one country to another, which fosters the introduction of new lineages into territories where they were previously unknown. Further, for dogs vaccinated with a particular CDV isolate, exposure to a genetically distant CDV may lead to sequestration of the incoming CDV virus in immunologically privileged sites (e.g. brain, ganglion, spinal cord, central, autonomic nervous systems, nasal plenum and bladder epithelium), allowing the propagation and spread of the genetically distant CDV without detection, since neurological symptoms may be overlooked by veterinary practitioners due to lack of sensitivity of the diagnostic tests and expense of long term treatment of a neurological patient.

Unfortunately, CDV vaccines currently in use have not been updated for about 60 years (Woma et al., 2010. Phylogenetic analysis of the hemagglutinin gene of the current wild-type canine distemper viruses from South Africa:Lineage Africa.Vet. Microbiol. doi:10.1016/jvetmic.2009.11.013) and have not kept pace with these changes. The use of these outdated vaccines is the likely cause of recent outbreaks of CDV infection, since these vaccines may not provide protection against infection with newly emerging lineages of CDV. Moreover, PCR sequencing has revealed that the vaccine isolate used in one commercial vaccine was misidentified (Demeter et al., 2009: Controversial results of the genetic analysis of a canine distemper vaccine strain. Vet. Microbiol. Published Online), further complicating the problem of determining how to best detect, monitor, and prevent CDV infection and transmission.

Clearly, epidemiological studies to investigate the rise in CDV clinical cases are warranted, as is the development of new immunological and vaccine compositions and diagnostic methods that take into account emerging isolates of CDV.

SUMMARY OF THE INVENTION

In one aspect, the present invention provides newly identified isolates of canine distemper virus (CDV). Accordingly, the present invention further provides updated immunogenic compositions and vaccine compositions. The vaccine compositions of the present invention are designed to provide broad-spectrum protection against emerging forms of CDV. In addition, the present invention provides updated diagnostic methods and kits for detecting CDV infection. The diagnostic methods and kits provide the ability to detect the newly evolved forms of the virus. The compositions and diagnostic methods and kits of the present invention are based, at least in part, on the discovery of previously unknown CDV variants, and take into account the emergence of mutant forms of the virus for which prior vaccine formulations and diagnostics are inadequate.

In a further aspect, the present invention provides a systematic method for selecting an antigen, e.g., a pathogenic isolate or portion thereof, that correspond to the genetic makeup of a broad spectrum of the source of the antigen, e.g. pathogen isolates or portion thereof, for use in such compositions and diagnostics.

The present invention further provides an isolated canine distemper virus (CDV) of European wildlife (EW) lineage comprising the characteristics of CDV 9041474B CDV-EW (ATCC Deposit No. PTA-10596). In another embodiment, the invention provides an attenuated strain of CDV isolated in cell cultures in which CDV strain CDV 9041474B CDV-EW (ATCC Deposit No. PTA-10596), or a progeny strain thereof, has been propagated. In a particular embodiment of this type, the attenuated strain of CDV may be plaque-purified. In yet another embodiment, the invention provides an immunogenic composition or vaccine, comprising the isolated CDV comprising the characteristics of CDV 9041474B CDV-EW (ATCC Deposit No. PTA-10596), or progeny thereof.

In still another embodiment, the invention provides an isolated canine distemper virus (CDV) of American-2 (AM-2) lineage having the characteristics of CDV 08021509 CDV-AM-2 (ATCC Deposit No. PTA-10597). In yet another embodiment, the invention provides an attenuated strain of CDV isolated in cell cultures in which CDV strain CDV 08021509 CDV-AM-2 (ATCC Deposit No. PTA-10597), or a progeny strain thereof, has been propagated. In a particular embodiment of this type, the attenuated strain of CDV may be plaque-purified. In a further embodiment, the invention provides an immunogenic composition or vaccine comprising the isolated CDV having the characteristics of CDV 08021509 CDV-AM-2 (ATCC Deposit No. PTA-10597), or progeny thereof.

The present invention also provides methods of eliciting an immune response to canine distemper virus in a subject in need thereof. One such method comprises administering to the subject an immunogenic composition or vaccine comprising an isolated CDV comprising the characteristics of CDV 9041474B CDV-EW (ATCC Deposit No. PTA-10596), or progeny thereof. In another such embodiment, the method comprises administering to said subject the immunogenic composition or vaccine comprising the isolated CDV having the characteristics of CDV 08021509 CDV-AM-2 (ATCC Deposit No. PTA-10597), or progeny thereof.

The present invention also provides diagnostic kits. One such embodiment comprises oligonucleotide primers specific for amplifying a nucleotide sequence as set forth in SEQ ID NO: 42. In another embodiment, the diagnostic kit comprising oligonucleotide primers specific for amplifying a nucleotide sequence as set forth in SEQ ID NO: 43. Those of skill in the art will recognize that such primers are based on the nucleotide sequence of a nucleotide sequence of interest that is to be amplified (e.g. a sequence that is targeted). In some embodiments, primers are homologous to or complementary to unique sequences of the target sequence.

The present invention further provides the recombinant and/or isolated nucleic acid molecules of the present invention. One such nucleic acid encodes the amino acid sequence of SEQ ID NO: 44, and/or the nucleic acid complement thereof. In another such embodiment, the nucleic acid molecule comprises the nucleotide sequence of SEQ ID NO: 42, and/or the complement thereof. In still another such embodiment, the isolated nucleic acid molecule comprises a nucleotide sequence that has greater than 99.5% identity to that of SEQ ID NO: 42, and/or to the complement thereof.

In still another embodiment, the recombinant and/or isolated nucleic acid molecule encodes the amino acid sequence of SEQ ID NO: 45, and/or the nucleic acid complement thereof. In yet another embodiment, the nucleic acid molecule comprises the nucleotide sequence of SEQ ID NO: 43, and/or the complement thereof. In still another such embodiment, the isolated nucleic acid molecule comprises a nucleotide sequence that has greater than 95% identity to that of SEQ ID NO: 43, and/or to the complement thereof.

The present invention further provides expression vectors that can comprise any of the isolated nucleic acid molecules of the present invention. In one such embodiment the expression vector comprises the isolated nucleic acid molecule encoding the amino acid sequence of SEQ ID NO: 44, and/or the complement thereof. In yet another embodiment, the invention provides an expression vector that comprises an isolated nucleic acid molecule encoding the amino acid sequence of SEQ ID NO: 45, or the complement thereof.

The present invention further provides immunogenic compositions and vaccines that can comprise any of the expression vectors of the present invention. In one such embodiment the immunogenic composition or vaccine comprises an expression vector that comprises the isolated nucleic acid molecule encoding the amino acid sequence of SEQ ID NO: 44, and/or the complement thereof. In another embodiment the immunogenic composition or vaccine comprises an expression vector that comprises the isolated nucleic acid molecule encoding the amino acid sequence of SEQ ID NO: 43, and/or the complement thereof.

The present invention further provides all of the isolated and/or recombinant proteins, polypeptides, peptides, fusion proteins and chimeric proteins of the present invention. In one such embodiment the polypeptide comprises the amino acid sequence of SEQ ID NO: 44. In another such embodiment that polypeptide is encoded by the nucleotide sequence of SEQ ID NO: 42.

In a further embodiment, the present invention provides immunogenic compositions and vaccines comprising CDV virions that encode a hemagglutinin protein. In related embodiments, the hemagglutinin can be partially encoded by a nucleic acid that comprises a nucleotide sequence as set forth in SEQ ID NOS: 1-33. In still other related embodiments, the present invention provides methods of eliciting an immune response to canine distemper virus in a subject in need thereof by administering to the subject one or more of such immunogenic compositions or vaccines.

The present invention further provides a method of selecting one or more isolates of a pathogen for use in immunogenic compositions, wherein the isolate(s) utilize(s) one or more of a most frequently used codon to encode a selected immunogenic protein, polypeptide or peptide of interest. One such method comprises the steps of 1) determining, for each isolate in a plurality of pathogen isolates, a nucleotide sequence encoding said selected immunogenic protein, polypeptide or peptide of interest; 2) for nucleotide sequences obtained in the determining step, obtaining codon usage data for one or more amino acid residues of interest in said immunogenic protein, polypeptide or peptide of interest, whereby data for frequency of codon usage is obtained; 3) identifying, from said data for frequency of codon usage, a most frequently used codon for each of said amino acid residues of interest in the immunogenic protein, polypeptide or peptide of interest; and 4) selecting, from among the plurality of pathogen isolates, one or more isolates that utilize(s) one or more of the most frequently used codons to encode the protein, polypeptide or peptide of interest. In one embodiment of the invention, the pathogen is a canine distemper virus.

In yet another embodiment, the invention provides a method of selecting one or more nucleotide sequences for a nucleic acid (which may be from an isolate of a pathogen) for use in immunogenic compositions. The nucleic acid utilizes one or more of a most frequently used codon to encode a selected immunogenic protein, polypeptide or peptide of interest. The method comprises the steps of 1) determining (e.g. from a plurality of pathogen isolates) a plurality of nucleotide sequences which encode the selected immunogenic protein, polypeptide or peptide of interest; 2) for nucleotide sequences obtained in the determining step, obtaining codon usage data for one or more amino acid residues of interest in said immunogenic protein, polypeptide or peptide of interest, whereby data for frequency of codon usage is obtained; 3) identifying, from the data for frequency of codon usage, a most frequently used codon for each of the amino acid residues of interest in the immunogenic protein, polypeptide or peptide of interest; and 4) selecting, from among the plurality of nucleotide sequences, the nucleotide sequence(s) that utilize(s) one or more of the most frequently used codons to encode the protein, polypeptide or peptide of interest.

BRIEF DESCRIPTION OF THE DRAWINGS

FIG. 1. Isolate 07091030 (SEQ ID NO: 1, nucleotides (nt) 438-1302 of H gene of CDV). This isolate is from a dog with a history of seizures and exhibiting neutrophils with multiple, intra-cytoplasmic inclusions. This CDV isolate formed large, multi-nucleated, syncytia in a Vero cell line expressing canine signaling lymphocyte-activation molecule (Vero+SLAM).

Figure 36:
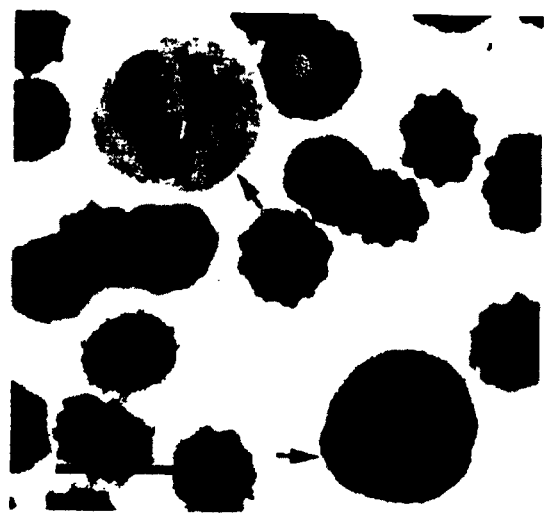

Based on the H protein sequence, this is a European wild life lineage isolate. This CDV isolate may be particularly useful, for example, as a challenge virus.

FIG. 2. Isolate 07091031 (SEQ ID NO: 2, nt 440-1494 of H gene).

FIG. 3. Isolate 07091032 (SEQ ID NO: 3, nt 440-1225 of H gene).

FIG. 4. Isolate 07101508 (SEQ ID NO: 4, nt 427-1335 of H gene). This isolate has high identity with European wildlife (EW) genetic lineage but is from a dog from Southern California with a history of Ondersteport vaccination. This isolate produces large syncytia in Vero+SLAM cells. The isolate has high identity with CDV from the lesser panda and Danish mink but is not closely related to the Ondersteport vaccine isolate.

FIG. 5. Isolate 07100609 (SEQ ID NO: 5, nt 833-1213 of N gene). The sequence of the nucleocapsid encoding genes of this CDV-like virus from a marine mammal (seal), matches canine isolate 164071 from the US (EU716337).

FIG. 6. Isolate 07110098 (SEQ ID NO: 6, nt 439-1286 of H gene).

FIG. 7. Isolate 07111080 (SEQ ID NO: 7, nt 630-1501 of H gene).

FIG. 8. Isolate 08010939 (SEQ ID NO: 8, nt 443-1343 of H gene).

FIG. 9. Isolate 08011277A (SEQ ID NO: 9, nt 423-1556 of H gene).

FIG. 10. Isolate 08011277B (SEQ ID NO: 10, nt 1530-410 of H gene).

FIG. 11. Isolate 08011277C (SEQ ID NO: 11, nt 433-1230 of H gene).

FIG. 12. Isolate 08011277D (SEQ ID NO: 12, nt 833-1578 of nucleocapsid gene). The H gene of this isolate could not be amplified. Lack of amplification indicates genetic variation (and hence, lack of homology) in the primer binding sequences. The nucleocapsid gene sequence matches that of a CDV isolate.

FIG. 13. Isolate 08011671 (SEQ ID NO: 13, nt 422-1589 of H gene).

FIG. 14. Isolate 08021509 (SEQ ID NO: 14, nt 441-686 of H gene).

FIG. 15. Isolate 08030074 (SEQ ID NO: 15, nt 447-1282 of H gene).

FIG. 16. Isolate 08030776 (SEQ ID NO: 16, nt 422-1541 of H gene).

FIG. 17. Isolate 08030777 (SEQ ID NO: 17, nt 411-1537 of H gene).

FIG. 18. Isolate 08031346 (SEQ ID NO: 18, nt 436-1059 of H gene).

FIG. 19. Isolate 08040383 (SEQ ID NO: 19, nt 1486-620 of H gene).

FIG. 20. Isolate 08050180A (SEQ ID NO: 20, nt 418-1552 of H gene).

FIG. 21. Isolate 08060351 (SEQ ID NO: 21, nt 412-1536 of H gene).

FIG. 22. Isolate 08060352 (SEQ ID NO: 22, nt 408-1553 of H gene).

FIG. 23. Isolate 08080696 (SEQ ID NO: 23, nt 423-726 of H gene).

FIG. 24. Isolate 08080941 (SEQ ID NO: 24, nt 387-1522 of H gene).

FIG. 25. Isolate 08081112 (SEQ ID NO: 25, nt 411-1207 of H gene).

FIG. 26. Isolate 08120827 (SEQ ID NO: 26, nt 413-1535 of H gene).

FIG. 27. Isolate 08120857 (SEQ ID NO: 27, nt 724-1522 of H gene).

FIG. 28. Isolate 09011024 (SEQ ID NO: 28, nt 578-1613 of H gene).

FIG. 29. Isolate 09020504-3 (SEQ ID NO: 29, nt 418-1549 of H gene).

FIG. 30. Isolate 09041289 (SEQ ID NO: 30, nt 889-1646 of H gene).

FIG. 31. Isolate 09041303 (SEQ ID NO: 31, nt 394-1526 of H gene).

FIG. 32. Isolate 09041474A (SEQ ID NO: 32, nt 410-1539 of H gene). Fully vaccinated dogs (two vaccinations with commercial Ondersteport CDV vaccine) in a large shelter in Tennessee developed upper respiratory tract disease, high fevers, green nasal discharge, cough, and eventually neurological symptoms, e.g. twitching. About 20 out of 55 dogs died, including the 4 month old female from which isolates 09041474A and 09041474B (see FIG. 37) were obtained.

FIG. 33. Isolate 09040826 (SEQ ID NO: 33, nt 418-1546 of H gene).

Figure 34A:
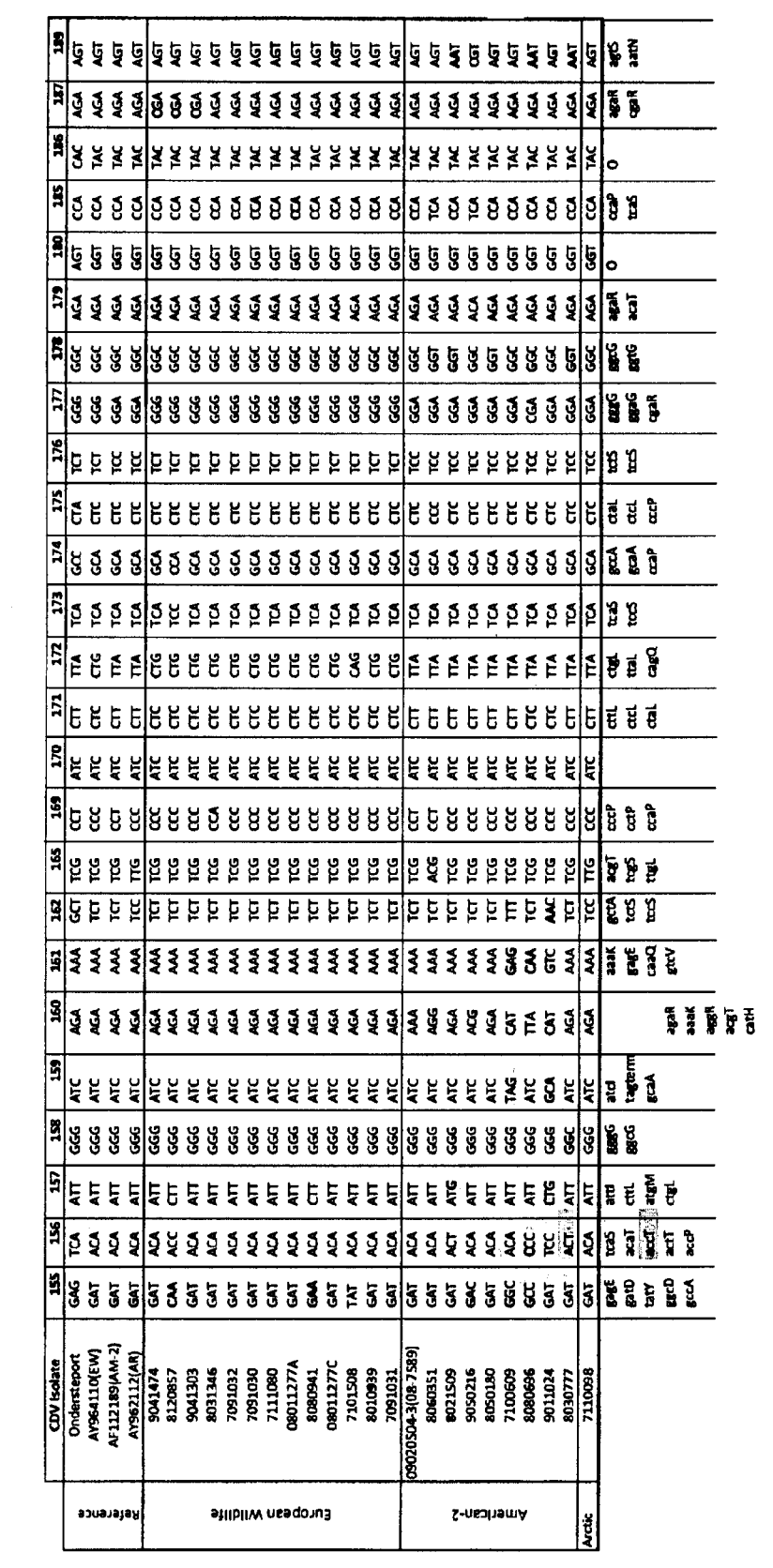
Figure 34B:
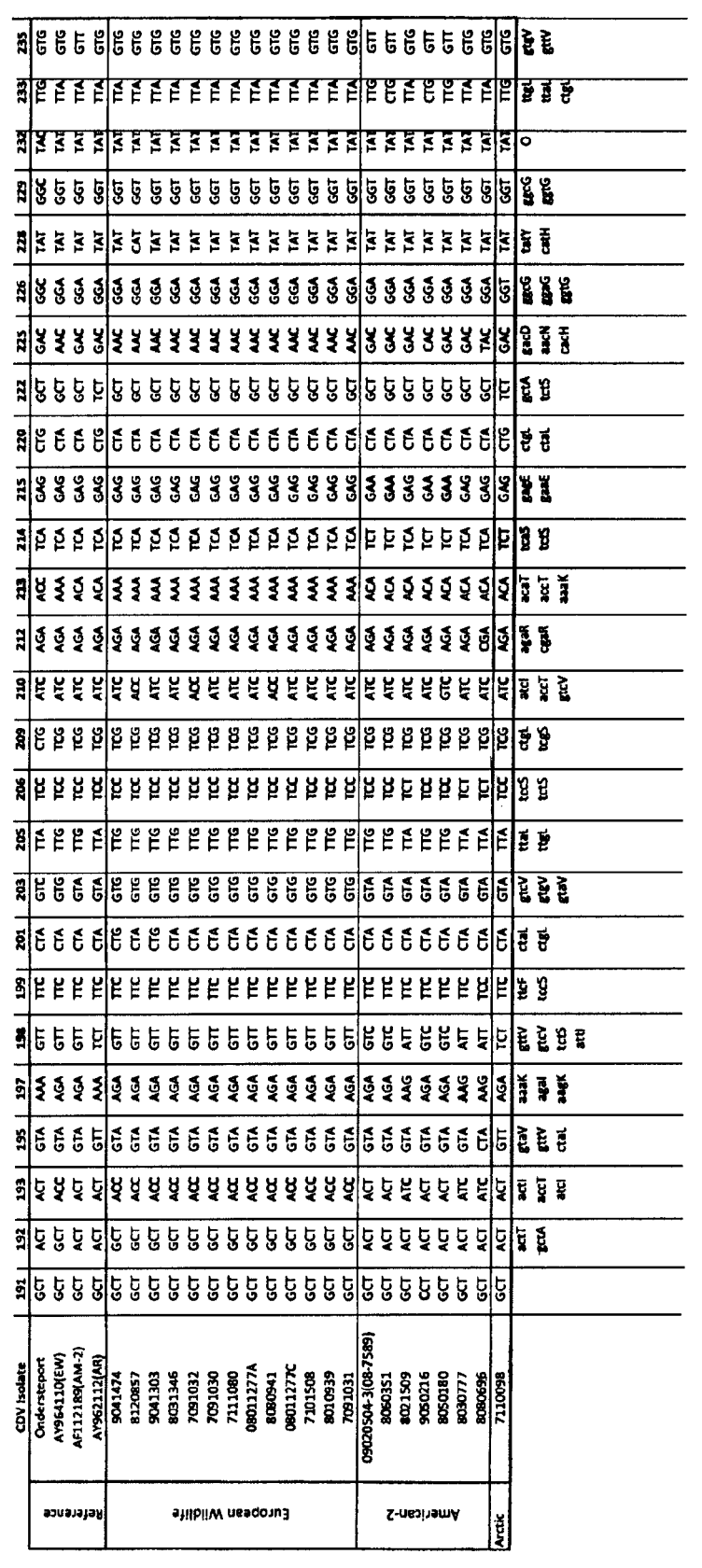
Figure 34C:
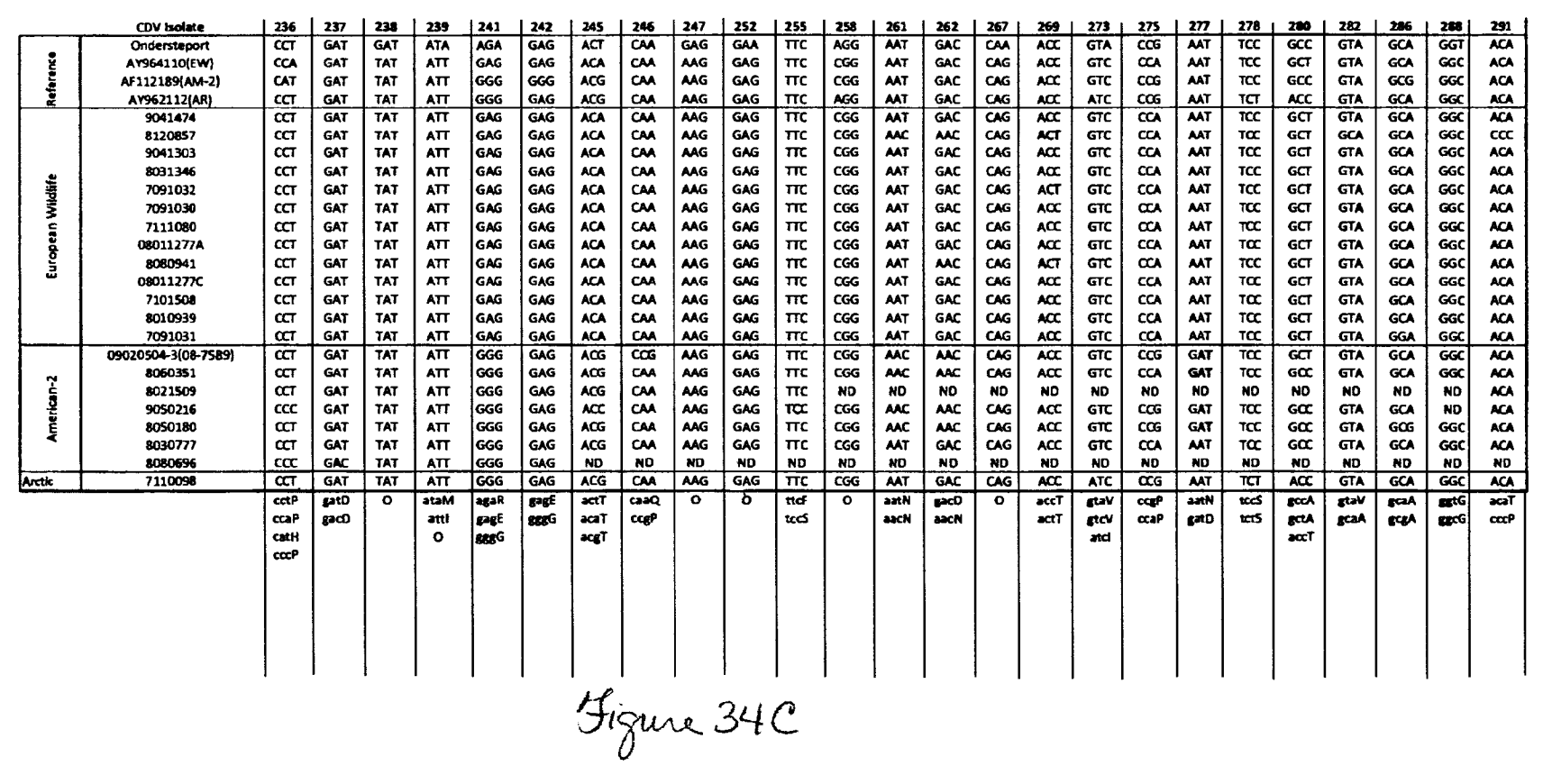

FIGS. 34A-F. Codon table showing canine distemper virus hemagglutinin (H) codon sequences from field isolates aligned with CDV-H vaccine and reference strain codon sequences using BioEdit program. Sequences: Ondersteport=CDV vaccine sequence; AY964110=reference European wildlife (EW) strain); AF112189=reference American-2 (AM-2) strain; AY962112=reference Arctic (Ar) strain. Differences in codons are shaded.

FIG. 35. Phylogenetic tree showing genetic relatedness of the many recent United States CDV isolates in the United States and GenBank reference sequences (underlined). The phylogenetic tree was constructed using MEGA4.1 program (available free of charge at the website located at megasoftware.net; Tamura K, Dudley J, Nei M & Kumar S (2007) MEGA4: Molecular Evolutionary Genetics Analysis (MEGA) software version 4.0. Molecular Biology and Evolution 24: 1596-1599).

FIG. 36. Blood film showing erythrocyte inclusions of CDV from a CDV infected dog (OADDL:07091030). CDV inclusions (arrows) are visible within a neutrophil and a lymphocyte. (Aqueous Romanowsky stain; bar=10 microns).

FIG. 37. Complete sequence of H gene from 09041474B (SEQ ID NO: 42), including stop codons.

FIG. 38. Complete sequence of H gene from 08021509 (SEQ ID NO: 43), including stop codons.

FIG. 39. Complete amino acid sequence of H protein from 09041474B (SEQ ID NO: 44).

FIG. 40. Complete amino acid sequence of H protein from 08021509 (SEQ ID NO: 45).

DETAILED DESCRIPTION

The present invention provides compositions that elicit an immunogenic response to CDV, vaccine compositions designed to provide protection against CDV infection, and CDV diagnostics. The compositions contain newly discovered CDV variants. The new variants reflect the evolutionary trends of CDV, and provide an indication of the predominant CDV strains currently circulating in the United States. The variants were, in part, isolated from dogs that had already been vaccinated for CDV, but which nevertheless contracted CDV and became ill, i.e. the dogs were the victims of vaccine failure. In order to stop or curtail the spread of CDV and to prevent vaccine failure, one or more of these new variants should be incorporated into new vaccine protocols. The invention also provides new diagnostic methods for detecting the new CDV isolates, and for differentiating between canine distemper caused by vaccine administration and canine distemper caused by an emerging virus which was not included in the vaccine, and against which the vaccine did not provide protection. In addition, the invention provides a method of analyzing RNA virus field isolates and emerging pathogens in order to determine which isolates are likely to be useful for inclusion in broad-spectrum immunogenic and vaccine compositions.

Several of the new isolates belong to the European wildlife CDV lineage; others belong to the American-2 (AM-2) and Arctic genetic lineages. 34 CDV viruses have been isolated, propagated in cell culture and the H genes of the viruses have been partially or fully sequenced. These viruses were from various states in the US (e.g. Oklahoma, Florida, Georgia, California, Missouri, Texas, Kansas and Tennessee). FIGS. 1-33 show partial sequences of cDNA complementary to the H gene from the isolates; FIGS. 37 and 38 show the complete H gene sequence for isolates 09041474B and 08021509, respectively, including stop sequences (TGA for both); and FIGS. 39 and 40 show the corresponding amino acid sequences of the H protein from isolates 09041474B and 08021509, respectively. In the amino acid sequences, the amino acid as position 5 in the sequence from 09041474B is glutamine, and amino acid at position 5 in the sequence from 08021509 is arginine.

The present invention also provides recombinant and/or isolated nucleic acids that encode any of the H-proteins of the present invention, but which do not include the signal sequence (the first 12 amino acid residues at the amino terminus of the H protein) and/or the stop codon and/or comprise an alternative signal sequence and/or an alternative stop codon. Expression vectors comprising such nucleic acids are also included in the present invention, as are the expressed recombinant polypeptides (including isolated recombinant polypeptides) that these nucleic acids encode.

FIGS. 34A-F show CDV hemagglutinin (H) sequences from several of the field isolates aligned with CDV-H vaccine sequences and reference strains. An analysis of this data served as the basis for the development of the Relative Preferred Codon Usage (RPCU) method/concept of analysis and selection of broad spectrum pathogen isolates for use in vaccines. The method is based on the newly recognized patterns of RPCU in pathogens, as disclosed herein. While the method is widely applicable to many pathogenic organisms (discussed in detail below), herein, an exemplary use for the analysis of RNA virus isolates is described. As used herein, an "isolate" (e.g. which may be a pathogen, such as, for example an RNA virus) has been substantially isolated and purified from a biological sample, and may have been subjected to passage and/or propagation in a suitable cell culture. Alternatively, the isolate may have been obtained from a pure culture, e.g. from an ATCC deposit.

In order to practice the method of RPCU, a representative number of isolates of interest are isolated from biological samples of animal subjects (including humans) obtained in one or more populations of interest. The isolates can be obtained within a given geographical region or area of interest, and/or from animal subjects suspected of harboring the pathogen. Suitable biological samples are those with the highest concentrations of the virus collected during the acute stage of pathogen infection, and include various tissue samples, bodily fluids or excreted substances (phlegm, saliva, blood, urine, stool, swabs [a generic term for many types of samples], etc.). Examples of suitable pathogens (e.g. emerging pathogens), which can be analyzed by RPCU include but are not limited to: various viruses such as RNA viruses, single-stranded DNA viruses, influenza viruses, HIV virus, etc.: various bacterial pathogens such as *Mycobacteria, Yersinia, Rickettsia* and *Bartonella* species; various fungi; and various protozoan pathogens such as Malaria, *Trypanosoma, Toxoplasma, Entamoeba, Giardia*, and *Cryptosporidia* species, etc. Those of skill in the art will recognize that a "representative number" of isolates of a pathogen may vary, but will generally be in the range of at least 20-25, usually at least 30-35, and may be any number of isolates (or sequences) without limit, depending on the availability of biological samples, the availability of resources that can be directed to the effort, etc.

A "population of interest" will generally be a population of individuals that are susceptible to a pathogen of interest, and may include individuals that exhibit disease symptoms when infected with the virus, or may be "carriers" who harbor the virus with few or no symptoms, but which are nevertheless infected with the pathogen.

A geographical area or region of interest may be, for example, a region or area bounded by geographical and/or legal boundaries, for example, a country, continent, state, county, etc.; or regions separated by geographical barriers such as bodies of water (rivers, lakes, oceans, etc.), mountain ranges, deserts, etc.; or regions/areas with a common climate or weather pattern, e.g. similar average temperature or rainfall, presence or absence of snow and ice, etc.

At least one protein, polypeptide or peptide of interest common to all isolates is selected for detailed gene sequence analysis. Generally, such a protein, polypeptide or peptide of interest is one that is known to be immunogenic. By immunogenic, it is meant that the protein, polypeptide or peptide elicits an immune response (e.g. the production of antibodies) in a host when the protein, polypeptide or peptide if present in the host (e.g. when a pathogen comprising the protein, polypeptide or peptide infects a host). Major immunogens can be determined by any of several methods known to those of skill in the art, including by Western blot analysis of serum from a convalescent patient that has recovered and is protected from further infection with the pathogen. Those of skill in the art will recognize that one or more than one such proteins, polypeptides or peptides may be analyzed using RPCU, but at least one is selected. Otherwise, more can be systematically selected for analysis but the one that is predominant based on, for example, Western blot analysis can be a good starting point. An unknown immunogenic protein can be sequenced by MALDI-TOFF. This helps to design the primers to amplify the sequences.

After selection of a suitable protein, polypeptide or peptide, the nucleotide sequence encoding the protein, polypeptide or peptide is determined using techniques that are well established, e.g. polymerase chain reaction (PCR) sequencing, etc. Alternatively, the sequences that are compared using this method may be obtained directly from biological samples without isolation of the virus, or they may be known sequences obtained from a database (e.g. GenBank or others).

The nucleotide sequences are then subjected to analysis to identify triplet codons and to align the codons in the correct translation (reading) frame. Sequence analysis may be conducted with any of the many nucleotide analysis programs, including but not limited to CLUSTAL W analysis using BioEdit software, the Multiple Sequence Alignment Program (MAP) provided by the Baylor School of Medicine, etc. Usually, the sequences that are analyzed are cDNA sequences, although the method is not limited to the use of cDNA, e.g. DNA, RNA, etc. may also be analyzed. Optionally, the corresponding sequence from one or more reference sequences (e.g. RNA virus reference strains) is included in the analysis. Generally, a reference strain will represent, for example, a pathogen type (e.g. a virus lineage) which was previously dominant (e.g. present at a high frequency) in the population and/or region under consideration. Such a reference strain may be, for example, an RNA virus that has been used in a vaccine against infection with the RNA virus. The preferred candidates for reference sequences are those which display the highest levels of homology and identity with both nucleotide and protein sequences of the pathogens (e.g. emerging pathogens), when analyzed using, for example, BLASTn and BLASTp programs. The level of homology and/or identity will be at least about 90% or 95%, or even at least about 99% or greater.

The triplet codons specifying the amino acids from the isolates (and, optionally, of one or more reference sequences) are aligned in frame in a format that may be readily compared, including but not limited to in tabular form, for example, in an Excel table. Those of skill in the art are well aware that the triplet code is redundant, and that more than one codon can encode the same amino acid. For each position corresponding to an amino acid residue in the protein, polypeptide or peptide of interest, the identity of the three nucleotides encoding the residue from each isolate is noted and compared across all isolates. For example, in a hypothetical protein of interest, if position 50 is a leucine, possible codons for this residue include tta and ttg. The actual codon at position 50 of all isolates is noted and compared to the codon present at all other isolates. From this comparison, the Relative Preferred Codon Usage (RPCU) can be determined. For example, if 75% of the isolates use "tta" to encode the Leu residue and 25% of the isolates use "ttg", then the RPCU value of tta is 75% and that of ttg is only 25%. Thus, tta is the preferred (i.e. the most frequently occurring or used) codon at that residue. In this manner, the most frequently used or preferred codon for each residue of interest of the sequence of interest is determined. The analysis may be carried out for all residues of a sequence, or for only a subset of residues, e.g. residues that are known to be involved in crucial pathogen activities or which are known to be part of an epitope or antigenic region, or which associated with virulence, etc.

The goal of the RPCU method is to identify isolates with nucleotide sequences which possess a high percentage of preferred codons for use in broad-spectrum vaccine preparations. This can be accomplished by any of several means. For example, a theoretical "ideal" sequence comprising only the most preferred codons can be determined and the actual sequences of the isolates can be compared to the theoretical sequence. The level of homology between each isolate and the ideal sequence is calculated. The isolate that displays the highest level (e.g. amount, percentage, etc.) of homology to the ideal sequence will be the isolate that utilizes the highest number of preferred codons. This isolate is the best "fit" to the ideal, and is selected as a vaccine component. Alternatively, an ideal sequence may not be determined but codon usage at each position is tabulated or calculated as described above, and a comparison is made among sequences by other methods that will occur to those of skill in the art, e.g. by simple visual inspection, to identify a sequence from an isolate that utilizes a very high level, or the highest level, number of preferred codons.

Without being bound by theory, this selection is consistent with the understanding that when a mutation occurs in the three-nucleotide sequence that encodes a residue, that mutation is likely to be perpetuated or to become widespread only if pathogens (e.g. RNA viruses) containing the mutation have some selective advantage over pathogens which do not contain the mutation. For example, some codons are translated more rapidly or with greater accuracy than others, and pathogens with such mutations may reproduce and infect new hosts more successfully than non-mutant pathogens. Therefore, these codons are eventually present more frequently in a population of pathogens due to natural selection. An isolate with a high percentage of frequently used codons likely possesses the cumulative advantages associated with the codons, and is likely to display the favorable characteristics of afforded by the codons, and thus, when included in a vaccine preparation, is likely to provide broad-spectrum protection. RPCU takes into consideration the internal protein epitopes of pathogens (such as viruses) that interact with the genomic nucleic acids (Pepin K M, J Domsic, and R McKenna. 2008. Genomic evolution in a virus under specific selection for host recognition. Infection, genetics, and evolution: 825-834).

RPCU impacts biological functions of RNA viruses such as CDV. The codons (triplet of nucleotides) are the most basic biological unit because they encode amino acids, which form the functional units of protein, including epitopes (e.g. about 6-7 amino-acids) and antigenic regions, or sequence motifs, which are directly involved in eliciting a host immune response to antigenic proteins, such as the H protein of CDV. Thus, the selection of CDV isolates based on RPCU reflects a phenotype/function of the virus, such as gene expression, H-protein expression and titers of the virus. Codon usage can also affect the breadth of protein expression and hence influence the tissues in which the virus or a protein is expressed. In a preliminary analysis, a gel-based PCR analysis of H protein expression by CDV showed that most American-2 isolates had uniformly lower (about 8-10 fold lower) H-gene PCR product expression, compared to most EW isolates. This result likely reflects the robust and biologically favorable H-gene codon composition in most EW CDV isolates, which leads to a higher frequency of EW CDV isolates in canine populations. An application of this method to CDV RNA viruses is presented in Example 4 below.

Those of skill in the art will recognize that computer implemented software (a computer program) may be developed to implement the RPCU method. Such software includes or encodes instructions for causing a computer to carry out the RPCU method, and may include, for example, means for entering sequences and other relevant data (e.g. name of isolate, codon alignment features, etc.), means for displaying entered data, means for representing the results of the analysis (e.g. a display on a screen, or a printout ["hard copy"] of the results in a suitable form, e.g. as a sequence, as one or more numerical indicators (such as "sequence #4" or "#4" as the best result), in graphical form, tabular form, etc.). Means for statistical analyses may also be included in the computer program, and the analysis may provide gradations of results, i.e. the program may rank the candidate sequences in terms of those that are likely to be the most suitable to those that are the least likely, and/or may simply provide one or more highest ranking (most suitable) sequences. The computer program may include instructions for carrying out an algorithm that is used to carry out the analysis.

The RPFU method is thus a method of selecting and/or obtaining an isolate of a pathogen for use in immunogenic compositions and vaccines. Such an isolate can be selected or otherwise obtained (e.g., through modification by standard genetic engineering techniques), which has preferred codons that encode a protein, polypeptide or peptide (usually an immunogen) of interest.

The RPFU method may include steps of: obtaining a plurality of isolates of the pathogen (e.g. an RNA virus) from biological samples from a plurality of different animals infected with the pathogen; selecting an immunogenic protein, polypeptide or peptide of interest associated with the RNA virus; determining a nucleotide sequence encoding the immunogenic protein, polypeptide or peptide of interest for each isolate of the plurality of isolates; identifying, in each of the nucleotide sequences encoding the immunogenic protein, polypeptide or peptide of interest, codons encoding amino acid residues of interest in the immunogenic protein, polypeptide or peptide of interest; determining, by comparing the nucleotide sequences encoding the immunogenic protein, polypeptide or peptide of interest, frequency of codon usage data for each of the amino acid residues of interest in the immunogenic protein, polypeptide or peptide of interest; from said frequency of codon usage data, identifying a most frequently used codon for each of the amino acid residues of interest in the immunogenic protein, polypeptide or peptide of interest; and selecting, from among the plurality of isolates of the pathogen, an isolate that utilizes one or more of the most frequently used codons to encode the protein, polypeptide or peptide of interest. In some RNA viruses, quasi-populations of the immunogen may be analyzed by RPCU software.

FIG. 35 shows a phylogenetic tree of the genetic relatedness of the isolates, based on the sequence of the H gene. In the tree, a very close related population of CDV isolates has emerged, a "predominant CDV population" that belongs to the European wild-life lineage. These European wild-life viruses can be checked by challenge with other minor CDV viruses of two other lineages, Arctic and American, i.e. the "minor CDV population". One or more broadly reactive, predominant isolates that are protective against both the European-Wildlife and one or the other (or both) of Arctic and American-2 lineage viruses can be used to make a CDV immunogenic composition for use as a vaccine that is effective against all CDV lineages currently circulating in the United States, or other suitable locations. In other words, the immunogenic compositions should elicit an immune reaction (e.g. antibody production) against European wild-life lineage viruses and against one or both of Arctic and American-2 lineage viruses. Vaccines of the invention should be protective against European wild-life lineage viruses and against one or both of Arctic and American-2 lineage viruses. The CDV used in such an immunogenic composition or vaccine contains nucleic acid sequences encoding antigens (antigenic regions, antigenic determinants, etc.) previously found only in and believed to be characteristic of European wild-life viruses, together with antigens previously found only in and believed to be characteristic of Arctic or American lineage viruses, or preferably both Arctic and American-2 lineage viruses.

One example of such a virus is isolate 09041474B, the complete hemagglutinin gene sequence of which is set forth in SEQ ID NO: 42. Several criteria were used for selection of this CDV isolate as a vaccine candidate. First, a panel of current CDV isolates was developed. (Historically, only a few isolates have been available based on published reports. Moreover, the reports to investigate the issue of CDV vaccine failure have been few.) Second, hemagglutinin sequencing and CDV genotyping were performed. Global nucleotide analysis using BALSTn, CLUSTAL-W, and phylogenetic analysis allowed clustering and characterization of CDV isolates in lineages, and 09041474B was determined to be of EW lineage. Then, codon usage tables (shown in FIGS. 34A-F) were used to select CDV vaccine isolate 09041474B according to the Relative Preferred Codon Usage (RPCU) analysis method described above.

The H gene sequence from isolate 09041474B (complete sequence, FIG. 37), differs from reference EW sequence (AY964110 in FIGS. 34A-F) in several respects. Firstly, the nucleotide sequence for the H gene of AY964110 was obtained using a tissue sample, i.e. a CDV virus with this sequence was not isolated. In contrast, the H gene sequence from 09041474B as described herein was obtained from an isolated CDV that had been grown and propagated in cell culture. The two sequences also differ in codon usage. For 09041474B, the codon at position 187 is CGA, the codon at position 201 is CTG, the codon at position 236 is CCT and the codon at position 303 is TCA. In further contrast to AY964110, in the 09041474B sequence, the codon at position 303 encodes serine rather than leucine (see FIGS. 34A-F). Isolate 09041474B displays robust growth in cell culture and it is possible that serine at position 303 confers advantages with respect to eliciting an immune response in subjects to whom virions with this sequence are administered. A deposit of the 09041474B CDV isolate, labeled 09041474B CDV-EW (whole, live viruses at a low passage of 2-3) was made at the American Type Culture Collection (ATCC) in Manassas, Va., with deposition #PTA-10596, deposit date Jan. 21, 2010. A second CDV isolate of interest, 08021509 (American-2, labeled 08021509 CDV-AM-2) was also deposited at ATCC with deposition #PTA-10597, deposit date Jan. 21, 2010. Both deposits were of whole viruses. The invention includes viruses that have the characteristics of the isolates that were deposited, for example: nucleotide sequences as disclosed herein; virulence and propagation attributes; attributes of syncytia (e.g. size, shape, number, appearance ([e.g. clearly demarcated, fuzzy, etc.), number of nuclei in the syncytia, etc.; among others.

In some embodiments of the invention, a multivalent CDV immunogenic composition and/or vaccine (e.g. European wildlife and American-2) will be employed. These two CDV lineages can be combined in a single preparation or administered separately as two separate dosages, for example, if they interfere with induction of CDV immunity.

The present invention provides all of the isolates disclosed herein, as well as vaccines and immunogenic compositions made from the isolates, and/or from antigenic portions of the isolates as described herein, e.g. nucleic acids comprising the nucleotide sequences as set forth in SEQ ID NOS: 1-33 and 42-43 and/or the proteins, polypeptides, or peptides encoded therefrom. The vaccines of the invention may be formulated in any suitable manner, including but not limited to using the whole virus (e.g. killed or attenuated, as described in detail below). In this embodiment, any of the novel CD viruses disclosed herein may be used to prepare a vaccine. Generally, such viruses may be identified by isolating the virus from tissue samples from dogs with symptoms of CDV infection, especially dogs that have been previously vaccinated against CDV, and sequencing and comparing the viral genome to known sequences (i.e. compared to CDVs isolated prior to the present invention, especially to CDV isolates that are currently used in vaccines). In particular, such new virus isolates may have an H gene sequence that contains a region that is identical to or homologous to that of isolate 09041474B (an exemplary isolate).

Generally, such viruses will have an H gene (or portion thereof) that is at least about 75%, preferably about 80%, more preferably about 85%, most preferably about 90%, or even 95, 96, 97, 98, 99, or 100% homologous (and/or identical) to the nucleic acid sequences disclosed herein, or complements thereof. In one particular embodiment of the present invention, the CDV isolate comprises an H-gene with a nucleotide sequence, comprising greater than 99% homology (and/or identity) with SEQ ID NO: 42 (i.e., that of isolate 09041474B). In a related embodiment, the CDV isolate comprises an H-gene with a nucleotide sequence comprising greater than 99.5% homology (and/or identity) with that of SEQ ID NO: 42 (i.e., that of isolate 09041474B)

In yet another embodiment, the CDV isolate comprises an H-gene comprising a nucleotide sequence with greater than 95% homology (and/or identity) with SEQ ID NO: 43 (i.e., that of isolate 08021509). In a related embodiment, the CDV isolate comprises an H-gene comprising a nucleotide sequence with greater than 99% homology (and/or identity) with that of SEQ ID NO: 43 (i.e., that of isolate 08021509)

Alternatively, such viruses may encode H proteins containing amino acid sequences that are at least about 75%, preferably about 80%, more preferably about 85%, most preferably about 90%, or even 95, 96, 97, 98, 99, or 100% identical to the amino acid sequence encoded by the nucleic acid sequence disclosed herein. Those of skill in the art are familiar with methods to calculate % homology or % identity. Such variant viruses may have H gene coding sequences that differ from those disclosed herein because of natural variations among isolates, or due to changes that are introduced deliberately e.g. by genetic engineering techniques. In other words, the viruses may be recombinant.

In other embodiments, only antigenic portions of the viruses described herein are present in the immunogenic or vaccine compositions of the invention. Such compositions may be formulated using, for example, nucleic acids encoding antigenic peptides or proteins as presented in SEQ ID NOS: 1-33 and 42-43, or antigenic epitopes or regions of peptides or proteins, from those sequences. For example, the vaccine preparations of the invention may comprise nucleic acid sequences that include the sequences set forth herein, complements thereof, and/or proteins, polypeptides or peptides encoded by such sequences. In addition, vaccines with certain variations of such sequences are also encompassed. While the sequences represent cDNA, the invention also includes corresponding ssRNA, ssDNA, double-strand (ds) DNA, dsRNA, complementary DNA, and RNA of any form (e.g. mRNA, RNA/DNA hybrids, etc.) that is based on, derived from or that complements these sequences. Such sequences may be either sense or antisense sequences. Further, sequences which display at least about 90% homology, or even about 95, 96, 97, 98 or 99% or greater homology to nucleic acid sequences of the CDVs disclosed herein, are also contemplated for use in the vaccines. Such sequences may differ, for example, by containing alternate codons that encode the same amino acid at one or more positions in order to maximize expression. In addition, portions of these sequences which encode epitopes or antigenic regions of e.g. the H protein are also contemplated, as are sequences which display 70%, or even more preferably about 80, 90, or 95% or even greater identity (e.g. 96, 97, 98 or 99% identity) to such amino acid sequences. Generally, about 6-8 amino acids constitute an epitope. Such sequences may vary, for example, by containing conservative or non-conservative amino acid substitutions, or deletions (especially amino or carboxy terminal deletions), or various insertions, etc., so long as the resulting protein/peptide is antigenic as described herein. Such antigenic regions are preferably at least about 10 amino acids in length, but may be much longer, e.g. encompassing an entire protein such as the H protein.

Further, nucleic acid sequences which hybridize to sequences disclosed herein (or to portions of those sequences) under stringent conditions (especially conditions of high stringency) are also contemplated. Stringent conditions refer to hybridization conditions which allow a nucleic acid sequence to hybridize to a particular sequence. In general, high stringent conditions refer to the hybridization conditions which allow a nucleic acid sequence of at least 50 nucleotides and preferably about 200 or more nucleotides to hybridize to a particular sequence at about 65° C. in a solution comprising about 1 M salt, preferably 6×SSC or any other solution having a comparable ionic strength, and washing at 65° C. in a solution comprising about 0.1 M salt, or less, preferably 0.2×SSC or any other solution having a comparable ionic strength. These conditions allow the detection of sequences having about 90% or more sequence identity.

Nucleic acids encompassed by the present invention, e.g. those with nucleotide sequences set forth in SEQ ID NOS: 1-33 and 42-43 (and variants thereof as described herein) may be obtained in various ways. For example, they may be obtained from natural sources such as from a viral isolate; alternatively, they may be produced synthetically. Those of skill in the art will understand that the capability exists in the art to synthetically produce very large sequences, e.g. entire viral or bacterial genomes (e.g. *Mycoplasma*), and the present invention encompasses sequences of any origin or manufacture that comprise the sequences disclosed herein, as well as the proteins, polypeptides and/or peptides expressed from the sequences.

The invention also provides recombinant constructs such as recombinant viruses, vectors, and expression vectors which express the proteins/polypeptides/peptides described herein (i.e. the amino acid sequences encoded by the nucleic acid sequence set forth in SEQ ID NOS: 1-33 and 42-43, or variants thereof). Such constructs include those which have been produced, for example, by cloning one or more of the sequences disclosed herein into a vector or host (e.g. plasmids, cosmids, viral vectors such as adenoviral and poxyiral vectors, or bacterial vectors, etc.).

In one embodiment, the construct is an expression vector that includes the previously noted nucleic acids and/or fragments thereof. Recombinant expression vectors used in this invention are typically self-replicating DNA or RNA constructs comprising nucleic acids encoding a CDV hemaglutinnin of the present invention and/or an antigenic fragment thereof, usually operably linked to suitable genetic control elements that are capable of regulating expression of the nucleic acids in compatible host cells. Genetic control elements may include a prokaryotic promoter system or a eukaryotic promoter expression control system, and typically include a transcriptional promoter, an optional operator to control the onset of transcription, transcription enhancers to elevate the level of mRNA expression, a sequence that encodes a suitable ribosome binding site, and a sequence that terminates transcription and translation. Expression vectors may also contain an origin of replication that allows the vector to replicate independently of the host cell. Recombinant expression vectors may be constructed by any of several means known to those of skill in the art. For example, genetic engineering techniques are known by which sequences of interest are removed e.g. from an isolate of origin such as a virus and ligated into a suitable expression vector. Alternatively, portions of an expression vector or an entire expression vector may be made synthetically; or a combination of ligation and synthesis protocols may be employed.

In addition, other useful elements may be included in the constructs described herein. For example, the constructs may encode various sequences such as histidine tags or other tags that are used to facilitate protein isolation, such as glutathione-S transferse (GST), and maltose binding protein; various linker or spacer sequences; various adjuvants and sequences that increase the antigenicity of the protein (e.g. haptens); sequences which introduce a desired/convenient restriction enzyme cleavage site or which encode a desired protease cleavage site; sequences encoding fluorescent or other detectable labels, or tagging or marking sequences (e.g. Green Fluorescent Protein (GFP), or portions thereof); various sequences that direct the location, export or processing of the encoded protein (e.g. leader sequences); heterologous signal sequences (i.e. signal sequences not normally associated with CDV H protein in nature); etc. Other possibilities will occur to those of skill in the art and are also intended to be encompassed by the present invention. When such sequences are included in the constructs, if they are contiguous with the viral sequences described herein, the entire coding sequence may be translated as a fusion or chimeric protein/polypeptide/peptide, and may or may not (depending on the sequence) be susceptible to post-translational modification. The expressed recombinant proteins/polypeptides/peptides of the present invention and their corresponding fusion or chimeric proteins/polypeptides/peptides are also provided by the present invention. In particular embodiments such recombinant proteins/polypeptides/peptides and their corresponding fusion or chimeric proteins/polypeptides/peptides are also isolated.

In addition, the present invention provides host cells that comprise such expression vectors. The host cell is optionally a prokaryote or a eukaryote host cell. Expression of nucleic acids encoding a CDV hemaglutinnin of the present invention can be carried out by conventional methods in either prokaryotic or eukaryotic cells.

The vaccines and immunogenic compositions of the invention may comprise any of the sources of the sequences described herein, e.g. a virus isolate, an attenuated virus, a recombinant construct, etc. Several methods of making vaccines suitable for vaccination against CDV are known in the art. See, for example, U.S. Pat. Nos. 4,193,990 and 4,193,991 to Appel et al., U.S. Pat. No. 4,303,645 to Carmichael et al., U.S. Pat. No. 4,971,793 to Wood et al.; U.S. Pat. No. 5,882,652 to Valdes et al., and U.S. Pat. Nos. 5,885,585 and 5,814,510 to Parrish et al., each of which offers variations of suitable vaccine-formulating strategies. The complete contents of each of these patents are hereby incorporated by reference. Generally, to manufacture a vaccine, a viral or other vector containing genetic sequences of the invention (either naturally, or due to genetic engineering) is employed. Examples of such viral vectors include viruses and virions (e.g. CDV) that are "killed", inactivated or otherwise attenuated so as to not cause severe disease symptoms in the animal to which it is administered, together with a suitable physiological carrier. The CDV virus can be inactivated (rendered unable to replicate) using chemicals such as formalin, binary ethylene amine, beta propriolactone, by using gamma irradiation or heat, or by other methods known in the art. Attenuation may be carried out, e.g. by repeated passage of the viral isolate in suitable host cells, and subsequent isolation of the resulting clonal isolate. In some embodiments, the attenuated virus retains the ability to replicate within the host, although this is not strictly necessary. Preferably, no disease symptoms will occur as a result of administration. However, those of skill in the art will recognize that many effective vaccine compositions cause some discomfort or relatively minor distress upon or after administration. However, the benefits of being protected against full-blown disease far outweigh this possibility. The attenuated virus may be a virus that naturally contains the nucleic acid sequence(s) of the invention (e.g. a CDV), or the virus may be recombinant in that the nucleic acid sequence is inserted into the virus by genetic engineering. In the case of recombinant vaccines, the nucleic acid sequences may be incorporated into viruses other than CDV to form heterotypic recombinant vaccines. Examples of such viruses include but are not limited to various herpesviruses, adenoviruses, poxviruses, non-pathogenic "orphan viruses", enteric viruses such as enterovirus, and others well known in the art. In addition, expression of the H gene could be accomplished in bacterial, yeast or parasite recombinant systems. In a preferred embodiment, the virus is a live, attenuated (modified) high titer CDV, and the nucleic acid is ssRNA. In addition, other forms of the vaccine are also contemplated. For example, "empty" virion particle vaccines (without nucleic acid) are also contemplated, as are vaccines comprising antigenic virion or other CDV proteins that are not assembled into a capsid. In addition, the vaccines of the invention may be multivalent and include multiple viruses. Alternatively, a single virus genetically engineered to contain nucleic acids encoding proteins from two or more of the novel CDVs can be constructed by recombinant technology by exchanging coding regions, as is known by those of skill in the art.

The CDV that is used in the compositions described herein is generally attenuated and safe, i.e. produces no or few symptoms of disease when administered to a suitable host animal. A CDV vaccine should not elicit antibody production in cerebrospinal fluid of a host. However, administration of the attenuated CDV still results in an immune response (e.g. a protective immune response) to CDV immunogens such as the H protein. The most frequently used method for producing an attenuated live-virus vaccine is to serially passage the virus in cell culture. For example, the virus may be passaged in a primary canine cell culture or canine cell line that does not harbor an oncogene, although other cell lines may also be used (e.g. chick embryo or fibroblast, VERO-SLAM cells, baby hamster kidney cell lines, as well as other hamster cell lines (Sultan S, N T Lan, T Ueda, R Yamaguchi, K Maeda, and K Kai. 2009. Propagation of Asian isolates of canine distemper virus (CDV) in hamster cell lines. Acta Veterinaria Scandinavica 51:38 doi: 10.1186/1751-0147-51-38), etc. Typically, for the first passage, a cell culture is infected with the selected inoculum of CDV. After obtaining clear evidence of virus replication (for example, virus-induced cytopathic effects [CPE] in the infected cells), an aliquot of the cell culture medium, or infected cells, or both, of the first passage are used to infect a second cell culture. The process is repeated until one or more mutations in the viral genome cause sufficient attenuation so that the virus can be safely used as a vaccine. The number of passages may vary somewhat e.g. at least about 20 and usually about 50 passages are used, but as many as e.g. 150 passages may be used. By then, the virus is sufficiently attenuated (i.e., reduced in virulence or diseases-producing ability) to be used in a vaccine formulation. The degree of attenuation is usually determined empirically by exposing the natural host to progressively greater passage levels of the virus.

It is also possible to attenuate the CDV viruses by repeat passages at decreasing incubation temperatures with or without mutagenic chemicals. Normally, CDV viruses are propagated at 37° C. However, over e.g. 50 passages at successively decreasing incubation temperatures for example, clonal strains of the virus are produced which no longer have the ability to replicate at core body temperature (37° C.) or above. Such viruses retain the ability to multiply in areas of the body that typically exhibit lower temperature, e.g. the nasal cavity, but do not replicate at the core body temperature. For example, in one embodiment, a cold-adapted, temperature CDV propagates in tissue culture cells at temperatures from about 26° C. to about 34° C., but does not do so at a nonpermissive temperature of about 37° C. (US patent application 2006121521, Dowling and Younger, the complete contents of which is hereby incorporated by reference). These viruses are therefore completely safe for use in CDV vaccines for animals, including wildlife and highly susceptible species such as large cats, mink and ferrets.

Other suitable vaccine components, e.g. pharmacologically acceptable carriers, are well-known to those of skill in the art, as is the preparation of such compositions for use as vaccines. Typically, such compositions are prepared either as liquid solutions or suspensions, however solid forms such as tablets, pills, powders and the like are also contemplated. Solid forms suitable for solution in, or suspension in, liquids prior to administration may also be prepared. The preparation may also be emulsified. The active ingredients may be mixed with excipients which are pharmaceutically acceptable and compatible with the active ingredients. Suitable excipients are, for example, water, saline, dextrose, glycerol, and the like, or combinations thereof. In addition, the composition may contain minor amounts of auxiliary substances such as wetting or emulsifying agents, pH buffering agents, and the like. If it is desired to administer an oral form of the composition, various thickeners, flavorings, diluents, emulsifiers, dispersing aids or binders and the like may be added. The composition of the present invention may contain any such additional ingredients so as to provide the composition in a form suitable for administration. The final amount of the translatable nucleic acid in the formulations may vary. However, in general, the amount will be from about 1-99%. The compositions may further comprise an adjuvant, suitable examples of which include but are not limited to Seppic, Quil A, Alhydrogel, oil-in-water emulsions, aluminum phosphate, carbopol, Emulsigen, and the like.

The immunogenic/vaccine preparations of the present invention may be administered by any of many suitable means which are well known to those of skill in the art, including but not limited to by injection, orally, intranasally, intratracheal, by ingestion of a food product containing the antigen, by intramuscular, subcutaneous, intravenous, transdermal, and intradermal routes, by eyedrops, or with a nebulizer or a needle-free instrument, etc. However, in a preferred embodiment, the mode of administration is by injection. In addition, the compositions may be administered alone or in combination with other medicaments or immunogenic compositions, e.g. as part of a multi-component vaccine. In particular, the immunogenic CDV could be combined with rabies virus, *Borrelia burgdorferi*, *Ehrlichia canis*, canine parvovirus, canine adenovirus, canine parainfluenza virus, canine coronavirus, *Babesia canis*, *Anaplasma phagocytophilium*, *Giardia* species, *Leishmania* species, *Leptospira* species or any combination thereof. etc. Further, administration may be a single event, or multiple booster doses (of the same or a different strain) may be administered at various timed intervals to augment the immune response. In addition, administration may be prophylactic, i.e. before exposure to the virus has occurred, or is suspected to have occurred, or after the fact, i.e. after a known or suspected exposure, or therapeutically, e.g. after the occurrence of disease symptoms associated with viral infection.

The invention also provides various types of recombinant vectors and/or expression vectors that contain and express the nucleic acid sequences disclosed herein (or portions thereof that encode antigenic peptides and/or polypeptides). Examples of such vectors and expression systems include but are not limited to: various bacterial (e.g. *Escherichia coli*) or probiotic-based (e.g. *Lactobacillus*) expression vectors; adenoviral vectors, baculovirus, *Pichia*, and other yeast expression systems; pox vectors such as raccoon pox vectors; etc. Such recombinant vectors and expression systems may also be utilized in vaccine preparations. Alternatively, they may be employed for other purposes such as for laboratory manipulation of the sequences, or for research or diagnostic purposes.

The invention provides methods of immunizing or preventing the symptoms of CDV infection in a subject (e.g. a mammal) in need thereof by administering to the subject a composition of the invention. Generally, the CDV vaccines are administered in an amount sufficient to provide active immunity in puppies and/or adult dogs. Preferably, the immune response is protective against future exposure to CDV, i.e. administration of the composition prevents the symptoms of disease associated with CDV infection, when compared to non-vaccinated controls. However, much benefit may also accrue if the immune response simply lessens or decreases the severity of disease symptoms, even if all symptoms are not eliminated.

In a preferred embodiment of the invention, the animals that are vaccinated using the vaccines of the invention are domestic dogs, including both adult dogs and puppies. However, the vaccination of other potential CDV hosts is also contemplated. Other potential hosts include other canids such as wild canids (e.g. wolves, wild dog species, etc.), larger species of cats (whether domesticated or wild), mink, red panda, foxes, lion and tigers, ferrets, rabbits, goats, etc. as well as other carnivores in general. Ferrets are highly susceptible to CDV. Thus a highly attenuated, modified live virus vaccine or recombinant CDV vaccine can be used. According to the American Ferret Association, MD, three CDV vaccines can be administered to healthy kits at 8, 11, and 14 weeks of age. While the vaccines will of course be used in domestic animals, wild or partially domesticated animals may also benefit from such vaccination, e.g. animals in zoos or protected areas, parks, in research facilities, etc. Wildlife can in particular be vaccinated with killed CDV vaccine because they are more susceptible to modified live virus vaccines, e.g. by use of edible bait which contains vaccine components. Any animal that can host the CDV variants, whether or not the virus causes disease symptoms in the host, may benefit by being vaccinated by the vaccine preparations provided herein. Vaccination of animals that are asymptomatic upon infection by the virus (i.e. silent carriers) would be beneficial in order to curtail the spread of the virus to more susceptible populations.

The invention also provides antibodies that bind specifically or selectively to antigenic determinants or antigenic regions of the CDV disclosed herein. In some embodiments, the antibodies are neutralizing antibodies that can neutralize the virus and thus prevent infection. Such differential antibodies may be polyclonal or monoclonal, although monoclonal antibodies are generally preferred. The antibodies may be of canine origin. Monoclonal antibodies will be prepared by injecting the viruses (e.g. killed viruses, proteins, or nucleic acids encoding the proteins) in mice or another suitable host such as rabbit or canine host. After 3 boosters, the spleens will be harvested and fused with myeloma cells. The monoclonal antibodies producing clones will be screened by ELISA, HA-HI, and indirect fluorescent antibody test. The clones that react with the viruses described herein, or with proteins isolated from the same, will be saved for development of CDV diagnostic assays. Polyclonal antibodies may be prepared by injecting one or more peptides that span amino acid codons that are preferred antigenic targets e.g. the H protein, into rabbits.

The invention also provides diagnostic methods and kits for the detection of the CDV variants described herein. Such kits include, for example, oligonucleotide primers specific for amplifying (e.g. by polymerase chain reaction, PCR) the nucleic acid sequences disclosed herein. Alternatively, such kits may include antibodies (e.g. monoclonal or polyclonal) that bind selectively or specifically to unique antigenic determinants displayed by the novel CDV variants. The kits are useful in monitoring the CDV status of, for example, any animal that is susceptible to CDV, especially canines. The kits are especially useful to monitor the CDV status of puppies and dogs that are exported or transported from one jurisdiction to another. In one embodiment, the diagnostic tests and methods of the invention are used to detect the presence of CDV in dogs (or other animals) that have been fully vaccinated but have nevertheless developed symptoms of CDV infection. Using the methods of the invention, it is possible to determine the genotype of the etiological agent of disease, and to ascertain whether the disease symptoms are caused by the vaccine strain, or by superinfection with a genetic variant that was not neutralized by vaccination, i.e. the vaccine did not provide protection against the genetic variant.

The invention is further illustrated in the following Examples, which should not be construed so as to limit the invention in any way.

EXAMPLES

Example 1

Preliminary Studies of Seven CDV Isolates

Canine distemper virus (CDV) is a highly contagious virus that causes multi-systemic disease in dogs. Seven cases of CDV in dogs from the USA were received. These CDV isolates formed large, multi-nucleated, syncytia in a Vero cell line expressing canine signaling lymphocyte-activation molecule (SLAM) (described below). Based on the hemagglutinin gene sequences, the CDV isolates from 3 states (CA, MO, and OK) formed two CDV genetic groups: Group I (major, 6/7) consisted of CDV isolates closely related to the European wildlife lineage of CDV. The group II (minor, 1/7) was genetically related to the Arctic-like lineage of CDV. However, both the CDV groups were genetically different from the current vaccine strains that belong to American-I lineage of the old (1930-1950) CDV isolates.

In this study, an evolutionary and genetic analysis of 7 CDV isolates from the United States was performed using the H gene sequences. The biological effects of the 1-1 gene sequence variation were investigated using an in vitro cell culture system. Ante-mortem samples included ocular swabs, nasal swabs, and peripheral blood anticoagulated with EDTA. The swabs were received in 1 to 2 ml of cold normal saline sent on ice by overnight delivery within 24 h of collection. Urine samples were not tested. Post-mortem samples were from tonsils, brains, bladders, and lungs (Kubo, T., Y. Kagawa, H. Taniyama, and A. Hasegawa. 2007. Distribution of inclusion bodies in tissues from 100 dogs infected with canine distemper virus. J. Vet. Med. Sci. 69:527-529). Approximately 2 to 5 g of each tissue was received in tubes sent on ice by overnight delivery for virological examination. The specimens were obtained from seven suspected cases of CD from three states in the United States (Oklahoma, four; Missouri, one; and California, two).

For direct fluorescent antibody testing, tissues were sectioned at 8-μm thickness and fixed with an acetone (75%)-methanol (25%) mixture at room temperature. Veterinary Medical Research and Development (VMRD), Pullman, Wash., USA supplied pretitrated, lot-to-lot certified conjugates for veterinary diagnostic applications. As part of quality control/quality assurance, the conjugates were tested before use on negative and known positive CDV controls. After addition of ready-to-use, prediluted, fluorescein isothicyanate-labeled, anti-CDV monoclonal antibody (VMRD, Pullman, Wash.) or polyclonal antibody conjugates (VMRD, Pullman, Wash.), the sections were incubated for 30 min at 37° C. After the unbound antibody conjugates were washed, the sections were counterstained with Evans blue for 15 min. After being mounted in buffered glycerol (pH 9.4), the sections were examined by fluorescent microscopy. Positive cells showed apple-green fluorescence in the cytoplasm and negative cells were brick-red.

For isolation, the tissues from CDV-infected samples were finely chopped, freeze-thawed twice to release the virus, and centrifuged at 8,000×g. The clear supernatant was filtered though a 0.22 μm syringe filter. The Vero cell line was derived from the kidney of a normal, adult African green monkey (Ceropithecus) in Japan. The recombinant cell line was derived by transfection of the Vero cells with canine signaling lymphocyte activation molecule (SLAM, also known as CD150) as described before by Seki et al. (Seki, F., N. Ono, R. Yamaguchi, and Y. Yanagi. 2003. Efficient isolation of wild strains of canine distemper virus in Vero cells expressing canine SLAM (CD 150) and their adaptability to marmoset B95a cells. J. Virol. 77:9943-9950). The inoculums (about 1 ml per 25-cm$^2$ flask) were incubated for 1 h at 37° C. with rocking every 20 minutes. After inoculation on a recombinant Vero cell line expressing canine SLAM, about 3.5 ml of Dulbecco's modified of Eagle's medium (Cellgro, Hendron, Va.) with 5% fetal calf serum was added. The cells were examined daily for cytopathic effects (multinucleated-syncytium formation) (Seki, supra). Vero cells expressing canine SLAM have been found to be useful for the primary isolation of CDV (Lan, N. T., R. Yamaguchi, K. Uchida, S. Sugano, and S. Tateyama. 2005. Growth profiles of recent canine distemper isolates on Vero cells expressing canine signaling lymphocyte activation molecule (SLAM). J. Comp. Path. 133:77-81).

For total RNA extraction (host and viral RNAs) from specimens, QIAmp viral RNA extraction kits were used (Qiagen Inc., CA). The quality and quantity of the RNA were checked by $A_{260}/A_{280}$ using a Nonodrop spectrophotometer (Nanodrop Technologies, CA).

For detection of CDV RNA, reverse transcriptase (RT)-PCR based on the nucleocapsid (N) gene was targeted (Kim, Y. H., K. W. Cho, H. Y. Youn, H. S. Yoo, and H. R. Han. 2001. Detection of canine distemper virus (CDV) through one step RT-PCR combined with nested PCR. J. Vet. Sci. 2:59-63). This protocol provides high sensitivity due to the nested amplification of the target gene, high copy number of the N gene, and the conserved sequence of the N-gene among CDV isolates. Briefly, the first-round product was amplified by the forward primer (Primer 1:5'-ATTTGGGATTGCTTAGGA-3', SEQ ID NO: 34) and reverse primer (Primer 2: 5'-GGCGCTCATCTTGGACAT-3', SEQ ID NO: 35). The protocol was reverse transcription at 45° C. for 1 hour, 95° C. for 3 min; 30 cycles of PCR with denaturation at 94° C. for 30 s, annealing at 54° C. for 30 s, and an extension at 72° C. for 1 min; and a final extension at 72° C. for 7 min, with the reaction mixture held at 4° C. The small-portion (1-microliter) product of the first reaction was subjected to a second round of amplification using primer 3 (5'-GTTAGCTAGTTTCATCCT-3', SEQ ID NO: 36) and primer 4 (5'-GGTCCTCTGTTGTCTTGG-3', SEQ ID NO: 37). The protocol for the second round was denaturation at 95° C. for 3 min; 30 cycles of denaturation at 94° C. for 30 s and annealing at 54° C. for 30 s; with an extension at 72° C. for 1 min. The final extension was performed at 72° C. for 7 min, and the reaction mixture was held at 4° C. before electrophoresis. The size of the second-round amplicon was 419 base-pairs, verified by including molecular size standards in agarose gel analysis.

For CDV genotyping, the H gene was used as the target (Martella, V., G. Elia, M. S. Lucente, N. Decaro, E. Lorusso, K. Banyai, M. Blixenkrone-Moller, N. T. Lan, R. Yamaguchi, F. Cirone, L. E. Carmichael, and C. Buonavoglia. 2007. Canine distemper virus (CDV) by hemi-nested multiplex PCR provides a rapid approach for investigation of CDV outbreaks. Vet. Microbiol. 122:32-42). The forward primer (primer 204+, nucleotides 388 to 409, 5'-GAATTCGACT-TCCGCGATCTCC-3', SEQ ID NO: 38) and reverse primer (primer 232b-, nucleotides 1543 to 1519, 5'-TAGGCAA-CACCACTAATTTRGACTC-3', SEQ ID NO: 39) yield an amplicon of 1160 base-pairs. The H-gene RT-PCR protocol was RT at 50° C. for 30 min and 94° C. for 2 min. The PCR protocol was 35 cycles of 94° C. for 1 min, 50° C. for 1 min, and 72° C. for 3 min and a final extension at 72° C. for 10 min, with the reaction mixture held at 4° C. The positive and negative CDV controls were included in each run of both detection (N gene) and genotyping (H gene) RT-PCR protocols. For phylogenetic analysis of the H gene sequences, the amplicons were sequenced at the Oklahoma Medical Research Foundation, Oklahoma City, Okla. The sequences were subjected to Basic Local Alignment Search Tool for Nucleotides (BLASTN) analysis (Altschul, S. F., T. L. Madden, A. A. Schaffer, J. Zhang, Z. Zhang, W. Miller, and D. J. Lipman. 1997. Gapped BLAST and PSI-BLAST: a new generation of protein database search programs. Nuc. Acid Res. 25:3389-3402) and compared to GenBank H gene sequences for CDV isolates from different species and geographic areas around the world. The percentage identities of the H gene sequences were recorded. Further, the H gene sequences were subjected to phylogenetic analysis and sequence comparison with H gene sequences of the vaccine CDV isolates (Ondersteport, Convac, Lederle, and Snyder Hill CDV isolates) deposited in GenBank. Alignments of the top 100 matches with known sequences were used to perform phylogenetic analysis by neighbor-joining using Jukes-Cantor method (NCBI, MD).

Peripheral blood films from two of the CD case samples (OADDL 07091030 and OADDL 07091031) were stained with an aqueous Romanowsky stain and examined by light microscopy. Both blood films revealed numerous eosinophilic structures within the cytoplasm of neutrophils and lymphocytes, consistent with CDV inclusions (FIG. 36). The presence of CDV inclusions was confirmed by the direct fluorescent-antibody test in both cases.

Six of the seven CDV positive samples were successfully isolated in the Vero cell line with canine SLAM/CD150. The cytopathic effects of CDV isolates were characterized by multinucleated syncytia that formed 1 to 2 days after inoculation. The presence of CDV was further detected by RT-PCR for the hemagglutinin gene. One CDV sample (OADDL 07061535) was tested only by RT-PCR and sequencing of the H gene; there was insufficient sample for virus isolation.

Based on RT-PCR for the H gene followed by sequencing, the level of identity among the CDV isolates (OK-1, OK-2, OK-3, OK-4, CA-1 and CA-2; major group I) was highest with a canine CDV isolate 19876 from Missouri, that is genetically most related to a Danish mink CDV isolate (Pardo, I. D. R., G. C. Johnson, and S. B. Kleiboeker. 2005. Phylogenetic characterization of canine distemper viruses detected in naturally infected dogs in North America. J. Clin. Microbiol. 43:5009-5017). Thus, it was the predominant CDV variant (six of seven isolates) in this study. These six CDV isolates belonged to the European wildlife lineage of CDV isolates. However, one isolate (MO-1; minor group II) was found that was most genetically similar to the canine CDV isolate 21260 from Missouri (Pardo, supra) that is closely related to a lesser-panda CDV isolate. This CDV isolate belongs to the Arctic-like lineage of CDV isolates. The information on the 2007 OADDL CDV isolates is summarized in Table 1, and partial nucleotide sequences of the H gene of these isolates are provided in FIGS. 1-7

TABLE 1

OADDL Canine Distemper Virus (CDV) Isolates

| OADDL No./ Designation | State of Origin | Vaccination Status[1] | Age (weeks) | Breed | % H Gene Identity Homology to Current Vaccine Virus[2] | Homology to MO 19876[3] | Virus Isolation | CDV Lineage[5] |
|---|---|---|---|---|---|---|---|---|
| 07061535 | OK-1 | I | 12 | Mixed | 89 | 98 | nd[6] | EW |
| 07091030 | OK-1 | NV | 44 | Siberian husky | 89 | 98 | yes | EW |
| 07091031 | OK-1 | NV | na | na | 89 | 99 | yes | EW |
| 07091032 | OK-1 | NV | na | na | 84 | 96 | yes | EW |
| 07101508 | CA-1 | V | 10 | American bulldog | 89 | 98 | yes | EW |
| 07110098 | MO-1 | V | 10 | Weimaraner | 89 | 90 | yes | A |
| 07111080 | CA-2 | V | 136[4] | Border collie | 97 | 96 | yes | EW |

[1] I - vaccination incomplete; NV = not vaccinated; V = vaccinated
[2] All isolates had less than 90% identity with the current vaccine isolates (Ondersteport, Lederle and Convac)
[3] All isolates had less than 90% identity with the USA MO 19876 CDV isolate except MO-1, which belongs to the Arctic lineage
[4] Animal recovered completely after supportive therapy
[5] EW = European wildlife; A = Arctic
[6] nd = not done.

The hemagglutinin glycoprotein varies approximately 10% among the CDV isolates and envelope protein H determines the cytopathology and tropism of the virus (von Messling, V. G. Zimmer, G. Herrler, L. Haas, and R. Cattaneo. 2001. In a preliminary analysis, the OADDL CDV isolates were compared with all the H sequences in the GenBank and it was found that CDV isolates cluster in geographically distinct lineages. For example, all the Argentina CDV isolates formed one distinct cluster. The South American CDV isolates were not included in the recent analysis of CDV isolates based on geography and H gene phylogeny (McCarthy, supra). However, they form a distinct South American cluster.

In recent papers, the terms genotype, cluster, and lineage have been used interchangeably by different investigators, but the results on CDV phylogeny were similar in all the studies (Martella, V., F. Cirone, G. Elia, E. Lorusso, N. Decaro, M. Campolo, C. Desario, M. S. Lucente, A. L. Bellacicco, M. Blixenkrone-Moller, L. E. Carmichael, and C. Buonavoglia. 2006. Heterogeneity within the hemagglutinin genes of canine distemper virus (CDV) strains in Italy. Vet. Microbiol. 116:301-309; McCarthy, supra; Mochizuki. M., M. Hashimoto, S. Hagiwara, Y. Yoshida, and S. Ishiguro. 1999. Genotypes of canine distemper virus determined by analysis of the hemagglutinin genes of recent isolates from dogs in Japan. J. Clin. Microbiol. 37:2936-2942), including this analysis, because all the investigators used the GenBank accession sequences. A member of a particular genotype of CDV has been proposed to have a more than 95% identity in the nucleotides of the H gene sequences (Mochizuki, supra) and, thus, the intragenotypic variation is less than 5% (Martella, supra).

The CDV isolate OK-1 (OADDL 07061535) was obtained from a 3-month-old, female, mixed breed, vaccinated dog from Oklahoma with history of conjunctivitis, nasal discharge and weight loss. The dog had not finished the complete course of vaccination, and had a history of roaming and eating garbage. This CDV isolate had maximum identity (98%) with CDV isolate 19876 (GenBank accession number AY964110.1). Based on the H gene analysis, CDV isolate 19876 belongs to the European wildlife lineage of CDV isolates along with OK-1.

The CDV isolate OK-2 (OADDL 07091030) was obtained from a tissue pool of an 11-month-old unvaccinated Siberian husky from Oklahoma. On necropsy, the conjunctival and tracheal epithelium contained intracytoplasmic, eosinophilic inclusions surrounded by clear halos. In the tonsils, there were marked lymphoid depletion and numerous inclusion bodies in the epithelium. This isolate had maximum identity (98%) with CDV isolate 19876 (canine origin, Missouri), and 94% identity with CDV isolates from Hungary (GenBank accession number EF095750.1), a Danish mink (Z47759.1), and a lesser panda (AF178039.1), CDV strain A75/17 (AF164967.1), and morbillivirus from a German ferret isolate (X84999.1). The CDV isolate A75/17 from the United States is regarded as a virulent protype of field CDV isolates (Simon-Martinez, supra). The level of identity of the H gene with the vaccine isolates (Convac, Lederle, and Ondersteport) was 89%.

The CDV isolate OK-3 (OADDL 07091031) was obtained from a dog in a shelter in Oklahoma. A blood tube was obtained but no other history was available on this case. Inclusions consistent with CDV were observed in leukocytes on a peripheral blood film and further confirmed by direct fluorescent-antibody test. The blood sample was positive for CDV by virus isolation. The H gene was sequenced and had 99% identity with CDV canine isolate 19876 (GenBank accession number AY964110.1), and 95% identity with CDV isolates from Hungary (EF095750.1), a Danish mink (Z47759.1), and a lesser panda (AF178039.1), CDV virus strain A75/17; CDV isolate 01-2641 and a German ferret morbillivirus strain (X84999.1).

The CDV isolate OK-4 (OADDL 07091032) was obtained from a tissue pool (bladder and lungs) from a dog adopted from an animal shelter in Oklahoma. This CDV isolate had maximum identity (96%) with CDV isolate 19876 (GenBank accession number AY964110.1). In descending order, it had 93% identity with CDV isolates from Hungary (EF095750.1), a lesser panda (AF178039.1), and a Danish mink (Z47759.1); 84% identity with the vaccine isolates; and 70% identity with the phocine distemper virus.

The CDV isolate CA-1 (OADDL 07101508) was obtained from a tissue pool from a 10-week-old male vaccinated American bull dog from California that died of CD. Three out of 4 littermates died of CD with respiratory signs, hyperkeratosis, and seizures. Of the three dead littermates, the necropsy report was available for one littermate. Its lungs were firm and congested on necropsy. The necropsy results of one of the four littermates were completely normal. The H gene sequence was 98% identical to a canine origin CDV isolate 19876 (GenBank accession number AY964110.1). The CDV isolate was 94% identical to the Hungarian CDV isolate, the lesser panda isolate (AF178039.1), and CDV strain A75/17 (AF164967). The CDV H gene sequence was 93% identical to CDV isolate 01-2641 (AY526496.1). The H gene of this CDV isolate lacked the Pst I site present in all vaccine CDV isolates (Demeter, Z., B. Lakatos, E. A. Palade, T. Kozma, P. Forgach, and M. Rusvai. 2007. Genetic diversity of Hungarian canine distemper virus strains. Vet. Microbiol. 122:258-269).

The CDV isolate MO-1 (OADDL 07110098) was obtained from nasal and conjunctival swabs of a 10-week-old, CDV vaccinated Weimaraner dog that had clinical signs compatible with CD. The dog developed 'chewing-gum' seizures, thickened footpads, coughing, nasal discharge, and congested lungs. The swabs were collected before euthanasia, and CDV was isolated in cell culture. The CDV isolate H gene had maximum identity (98%) with CDV isolates 21261 and 18133 from Missouri, and 97% identity with CDV isolates from Italy (48/05 and 179/94) and Hungary (H06Bp10S, H06 Bp8F, H05 Bp7F, H05 Bp6F, and H05 BpBp5F). The H gene sequence of this CDV isolate had 95% identity with a CDV isolate from a Greenlandic dog and only 90% identity with CDV 19876. It had 89% identity with the vaccine CDV isolates and 70% identity with the phocine distemper virus H gene. Moreover, this CDV isolate lacks the Pst I restriction site present in all vaccine CDV isolates (Demeter, supra). Based on phylogenetic analysis this isolate belongs to the Arctic-like lineage of the CDV isolates.

The CDV isolate CA-2 (OADDL 07111080) was obtained from a combination of nasal, pharyngeal, tonsil, and conjunctival swabs of a 32-month-old neutered male, vaccinated Border collie with a history of vomiting, diarrhea and lymphopenia. The H gene sequence had maximum identity (96%) with CDV isolate 19876. This isolate had 93% identity with the Hungarian CDV isolate, the lesser Panda CDV isolate, and the Danish mink CDV isolate; 92% identity with CDV strain A75/17 (GenBank accession number AF164967.1); and 92% identity with the German ferret CDV isolate. Based on phylogenetic analysis, this CDV isolate clusters with CDV isolates of the European wildlife lineage. This dog recovered after treatment and has been clinically healthy for the last 3 months. The survival of this dog after a natural exposure to a CDV isolate of European wildlife lineage is probably due to resistance based on age, genetic resistance, and immunity after complete vaccination with a commercial CDV vaccine. This dog had a CDV titer of 1:16 by CDV serum neutralization 3 months after recovery from CDV infection.

Five out of six OADDL 2007 CDV isolates were found to produce multinucleated, syncytia in a Vero cell line expressing the canine SLAM receptor. It has been proposed that syncytial size is a correlate of the degree of virulence of the CDV isolates (Cosby, S. L., C. Lyons, S. P. Fitzgerald, S. J. Martin, S. Pressdee, I. V. Allen. 1981. J. Gen. Virol. 52:345-353) because it correlates with the ability of the CDV to spread from cell-to-cell. The aggressive spread in cell culture, the ability to produce large numbers of inclusions in canine lymphocytes that naturally express SLAM/CD150, and the ability to produce fatal infections in vaccinated dogs indicate that these canine isolates of European wildlife lineage are virulent for dogs.

This Example shows that the EW lineage is emerging as the predominant CDV isolate in the US.

Example 2

Additional CDV Isolates

Using the methods described in Example 1, additional CDV isolates were identified and are listed in Table 2.

TABLE 2

OADDL Canine Distemper Virus (CDV) Isolates

| OADDL No./ Designation | State of Origin[1] | Clinical Sign[2] | CPE[3] | Vaccination Status[4] | Age (weeks) | Breed | CDV Lineage[5] |
|---|---|---|---|---|---|---|---|
| 8010939 | OK | R, N | na | na | 20 | Miniature Schnauzer | EW |
| 08011277-A | OK | R | + | na | 12 | Small breed | EW |
| 08011277-B | OK | R | + | na | 12 | Small breed | EW |
| 08011277-C | OK | R | + | na | 12 | Small breed | EW |
| 8011671 | GA | R | na | V | 10 | Mix | EW |
| 8021509 | FL | R, N | + | V | 12 | Mix | AM-2 |
| 8030674 | CA | R, N | na | V | 8 | Golden Retriever Mix | EW |
| 8030776 | OK | R, N | + | V | 16 | Mix | EW |
| 8030777 | FL | N | + | V | 12 | Mix | AM-2 |
| 8031346 | CA | na | na | V | 12 | Pitbull | EW |
| 8040383 | MO | R | +/− | na | 6 | Weimaraner | AR |
| 8050180A | OK | R | na | na | 14 | Pitbull Mix | AM-2 |
| 8060351 | MO | R, N | na | V | 9 | Shih Tzu | AM-2 |
| 8060352 | MO | R | na | V | 8 | Welsh Terrier | AM-2 |
| 8080696 | FL | R | + | V | 24 | Mix | EW |
| 8080941 | OK | N | + | na | 12 | Rat Terrier | EW |
| 8081112 | MO | N | +/− | V | 11 | Irish Terrier | AM-2 |
| 8120827 | OK | N | + | na | 0.3 | Dachshund | EW |
| 8120857 | OK | N | + | na | 5 | Yorkshire Terrier | EW |
| 9011024 | na | N | + | V | 156 | Akita Mix | EW |
| 09020504-3 (08-75891) | KS | na | + | na | na | na | AM-2 |
| 09020504-2 (56928) | KS | na | na | na | na | na | AM-2 |
| 09020504 (58829B) | KS | na | + | na | na | Leopard | AM-2 |
| 9041303 | na | R | +/− | V | 24 | Cattle Dog Mix | EW |
| 09041474A | TN | R | + | V | 16 | Border Collie Mix | EW |
| 0904147B | TN | R | + | V | 16 | Border Collie Mix | EW |

[1]State of origin; na = not available
[2]Clinical Signs: R = Respiratory (coughing, ocular and nasal discharge, sneezing); N = nervous (tremors, twitching, urination change, exterior rigidity)
[3]CPE = Cytopathic Effect: + = positive; − = negative; +/− = suspect; na = not available
[4]Vaccination Status: V = vaccinated; NV = not vaccinated; na = not available
[5]CDV lineage: EW = European wildlife; Am-2 = American-2 sample inoculation 18-24 hours after inoculation (Fast-growing CDV isolates). In some CDV isolates, the margins of the syncytia were well defined with almost circular margins. In other CDV isolates, the margins of the syncytia were not that clearly demarcated. These "fuzzy" CPE CDV isolates tended to spread rapidly with daughter syncytia next to the mother syncytium. In other CDV isolates, daughter syncytia appeared far away indicating another colony (colonies) of virus growth. In short, CDV isolates showed variable cytopathology. CDV isolates from USA differ in the speed (Fast and Slow), spread (Large and Small), size, shape (Round and Irregular) of the syncytia formation and invasiveness of the host cells by CDV isolates. These biological properties may have bearing on the protection offered by the current vaccines. For example, codon usage of critical viral genes can affect the replication efficiency of CDV, as discussed in Example 11.

Example 3

Continuing Investigations of Emerging CDV Isolates: Differences in Cytopathology (CPE) Among Recent USA Canine Distemper Viruses The results obtained in Examples 1 and 2 prompted a continued effort to isolate and characterize additional CDV isolates from the USA. Studies were carried out as described for Example 1. CDV samples were inoculated in Vero+ SLAM cell line. Most CDV isolates produced large syncytia with large number of nuclei. A smaller number of CDV isolates produced smaller sized syncytia with few cell nuclei. In several CDV isolates, multiple syncytia appeared after virus Example 4

Comparative Genetic Analysis of CDV Isolate Sequences: Relative Preferred Codon Usage (RPCU)

Ten hemagglutinin residues (29, 178, 180, 225, 386, 412, 475, 530, 549, and 603) are known to be under positive selection among CDV lineages (McCarthy, supra). The hemagglutinin (H) gene of the isolates were sequenced or partially sequenced and the resulting sequences are shown in FIGS. 1 to 33. The partial H-gene sequenced (about nucleotide 534-1236 hemagglutinin gene fragment) from the wild type CDV isolates were aligned with reference CDV sequences from GenBank using CLUSTAL W provided with Bio-edit program). Of note, a viral isolate containing the reference sequence for the EW strain has never been isolated, propagated in cell lines, or characterized. The reference EW sequence was obtained by sequencing carried out on tissue extracts.

The results of the RPCU analysis, depicted in FIGS. 34A-F, showed the following:

At residue 180, the codon is AGT in Ondersteport-like vaccines such as Galaxy, Proguard, Continuum, and Vanguard. However, this codon is GGT in European wildlife (EW), and in all wild type CDV isolates. This codon can be useful in designing a Taqman RT-PCR to distinguish the Ondersteport-like vaccines from wild type CDV isolates circulating in the USA.

At residue 225, the codon is GAC encoding aspartic acid (D) in all vaccines. However, it is AAC in American-2 CDV and in raccoon distemper virus (RDV) 09050216 it is CAC (encoding histidine, H).

At residue 386, the codon is ACC (threonine, T) in all Ondersteport-like vaccines (all except the Pfizer vaccine). However, it is TAC in EW, AM-2 and AR lineage CDV wild type viruses and in the Pfizer vaccine. This codon is thus useful in developing a differential Taqman RT-PCR for distinguishing most of the commercial CDV vaccines and wild type CDV isolates.

At residue 412, the codon is CCT, which encodes proline (P) in vaccines and wild type CDV viruses. However, in isolate 07110098 it is CAT (encoding histidine, H) as is also the case for the Arctic-lineage of CDV.

Relative Preferred Codon Usage (RPCU) has been developed from analysis of the codon usage comparisons. One goal of an RPCU analysis is to identify RNA viral isolates (e.g. CDV isolates) suitable for making a broad-spectrum vaccine capable of providing protection against most isolates circulating in a particular geographic area (e.g. the United States). RFCU also allows evaluation of the genetic distance of isolates that are outside an area of interest based on codon usage. RPCU is based in part on the observation that, in addition to amino acid residues, codons themselves are under evolutionary selection pressure (Gustavo et al., Lost in Translation: Codon Usage and HIV-1 Evolution, AIDS Reviews 2004; 6:54-60).

To develop and implement RPCU analysis, a codon usage Table depicted in FIGS. 34A-F was created in which each entry presents the three nucleotides of a single triplet codon. The codon usage Table can also be created using a concatamer approach, e.g. using an Excel program with MEGA4.1 software. To create this Table, first all the sequences were subjected to CLUSTAL W analysis using BioEdit software. Then, triplets of nucleotides in frame with the coding sequence were manually entered into an Excel table. In this manner, residue positions 155-428 of the hemagglutinin protein were analyzed, and the codons for residues of interest were included in the Table. For each residue position, at the bottom of the column, the codons used were retyped in lower case letters and the encoded amino acid was indicated using a single capital letter. The alternative codons that did not lead to change of amino acid (substitutive mutations, S/−) were also noted. For example, residue position 176 uses two codons (tct and tcc, both encoding serine, S). The residues positions for which only the Ondersteport sequence differs from all other codons in the Table (i.e. is an outlier) were also noted by an "O" at the bottom of the column) e.g. residue positions 180 and 186. Some residue positions were identical in all CDV isolates. These identical residue positions are not shown in the codon usage Table because they did not affect the selection of the CDV vaccine isolate.

To identify the relatively preferred codon at each residue, the entire Table was examined residue by residue, i.e. column by column. For example, in the column representing codons at residue position 185, either CCA or TCA is used to encode the amino acid at this position. However, CCA is the preferred codon compared to TCA, since CCA is present in the majority of isolates. Similarly, preferred codons were determined at each of the residue positions. For some residues, the least preferred codons were also identified. As can be seen, most of the least preferred codons occur in American-2 and Arctic isolates. This pattern of relative preferred codon usage could be one of the major reasons for the biological advantage of EW over AM-2 and AR CDV isolates. Canine distemper virus is labile in the environment but highly contagious, similar to the measles virus. A CDV isolate in a geographical area that has a replication advantage due to more biologically fit codon usage and higher replication titers and shedding (e.g. in nasal secretions and other portals of delivery in a dog population) has the ability to spread to and affect even vaccinated dogs. Thus, codon usage is the minimum functional unit of virulence factors (such as H protein of CDV) with effects on epidemiological, biological and disease outcomes in host populations.

As noted above, a major goal of the present RPCU analysis is to identify one or more CDV isolates for use in a broad-spectrum CDV vaccine development. Preferably, a vaccine preparation containing or based on such CDV isolates would provide protection against infection by most CDV isolates currently circulating in the US, or at least lessen deleterious symptoms associated with such infection. EW isolate 09041474B was identified as using a preferred codon at most residue positions (e.g. at positions 185, 192, 193, 203, 205, etc.) and was thus selected for further vaccine development.

The approach of RPCU was developed in part because the residues that are critical for the immunogenicity of the CDV H protein have not been determined. RPCU analysis provides a method to identify robust CDV vaccine candidates in the absence of detailed knowledge of the antigenic characteristics of H protein residues. RPCU can be used to analyze and select vaccine candidates from among isolates of other types of RNA viruses as well, and will be useful in cases where the newly emerged virus has not been well studied but an emergency vaccination is called for to stop a growing outbreak.

Further, the new variant AM-2 isolates described herein have higher isolate specific codon usage (as determined by RPCU) and, while this makes them less suitable for a broadly reactive CDV vaccine, these genetically unique isolates will make excellent challenge viruses to check the efficacy of the improved CDV vaccines. RPCU is consistent with self-optimization for new host adaptation being one of the fundamental reasons for evolution of emerging pathogens of animals and humans.

Example 5

Phylogenetic Analysis of Recent CDV Sequences, Reference CDV Sequences from Gen-Bank for Each CDV Genetic Lineage, and all Commercial CDV Vaccines FIG. 35 shows the phylogenetic analysis of several CDV hemagglutinin partial sequences from recent US CDV samples compared to commercial CDV vaccines strains and GenBank reference sequences for all known CDV genetic lineages, including South American sequences. Observations that can be made are as follows:

American-1 (AM-1) genetic lineage: reference sequence=AF378705, Ondersteport strain from 1950's; none of the currently circulating CDV isolates from the US cases were of this CDV lineage. Most of the current commercial CDV vaccines (Continuum DAP, Intervet (n=1 lot); Duramune Max 5, Fort Dodge (n=1 lot); Galaxy DA2PPv, Schering Plough (n=3 lots); Merial (recombinant canary pox vectored CDV-H gene vaccine (n=1 lot) are all based on the AM-1 lineage.

American-2 (AM-2) genetic lineage: reference sequences=AF112189; Z47762; AF259552. Based on the phylogenetic analysis, the 3 reference sequences were dispersed in three locations on the CDV tree shown by the underlined sequences. All but one AM-2 CDV isolate clustered with and around the AF112189 reference sequence. A total of 8 AM-2 CDV isolates were isolated in this study. America-2 is the second largest cluster of CDV circulating in the USA now. An isolate from this lineage should be included in the updated CDV vaccine and has thus been deposited with ATCC (Manassas, Va.).

Arctic (AR) genetic lineage: Two reference sequences (AY964112 and AY964108) constituted this cluster. We identified a few USA samples in this cluster. Both (07110098; 08040383) the samples were from Missouri, USA. This is minor CDV genetic cluster. This CDV lineage will be suitable for some parts of the USA.

Asia-1 (AS-1) genetic Lineage: Three reference sequences (AB016776; AB 212963; AY378091) constituted this cluster. None of the USA CDV isolate is related to this lineage. This type of CDV lineage has been reported in Japan, China, and Korea. CDV vaccines for these Asian countries may include this lineage.

Asia-2 (AS-2) Genetic Lineage: Two reference sequences (AB0470767 and AB 252718) constitute this genetic cluster. None of the USA CDV isolate is related to this lineage. This type of CDV lineage has been reported in Japan, China, and Korea. CDV vaccines for these Asian countries should include this lineage.

European-Wildlife (EW) Genetic Lineage: The reference sequence for this lineage was AY964110. Most of the EW CDV isolates (n=14) from the US clustered around the reference strain of CDV. However, two EW were branched separately. This major cluster of CDV isolates should be included in the updated CDV vaccines for use in USA dogs.

European (E) CDV Lineage: This lineage cluster contained only the two reference sequences (AF478550, DQ494318). Pfizer CDV vaccine branched close to this cluster. South American (SA) CDV Lineage: Four reference CDV sequences clustered in this lineage. These isolates separated as a new branch from the tree indicating that they are unique from USA isolates and current vaccines.

Measles virus Edmonton B sequence was used as an outlier sequence for comparison with US vaccines and current isolates for phylogenetic analysis.

A potential new lineage of CDV has been described in South Africa (Woma, supra).

Example 6

Vaccine Development

Many limitations in the current art of CDV vaccine development had to be overcome to select the isolates for improved CDV vaccine development. One of the current limitations of CDV vaccines is the availability of CDV isolates from cases of vaccine failure. The problem of CDV vaccine failure has not been fully appreciated and there is not much published data to support these observations. Moreover, current veterinary diagnostic techniques have not been extensively applied to the problem of vaccine failure due to a lack of available methods and the cost of diagnostic testing of ante-mortem samples showing neurological symptoms. Thus, prior to the present invention, the data on current CDV isolates with respect to improving the quality of CDV vaccines was very limited, consisting mainly of isolated reports that were largely overlooked and reports of single dogs. This is undoubtedly because most owners of the deceased dogs do not wish to pay for further medical investigations and simply dispose of the animal carcasses. Therefore, no further scientific information is obtained.

The 34 CDV isolates described herein are compared using hyper-immune serum against the American-1 CDV isolate utilized in the commercially available Onderstreport canine distemper vaccine. Hyper-immune serum is a useful reagent because it is prepared by administering multiple vaccines to adult dogs that are immunocompetent. Hyper-immune sera offer the best case scenario. However, in a field situation, most dogs will receive two CDV vaccines as puppies. Thus, although hyper-immune serum is a useful reagent, it has limitations for designing and selecting CDV isolates for vaccine preparation. Here, we propose a novel bio-informatics approach (RPCU, described above) for broad-spectrum CDV vaccine development. All available genotypes of CDV currently circulating in the US are included in the analysis. Several (e.g. at least 3-5 isolates of each CDV genotype) are selected (using phylogenetic analysis) for antigenic comparison based on sequence alignment using Bio-Edit. This allows CDV isolates that have the maximum antigenic distance to be selected and compared to the current CDV vaccines. Any isolate that is at least 4-fold lower in SN test using either hyper-immune serum or a serum from a dog that has received only two vaccines is selected for further testing in vivo.

Both sero-negative and low sero-positive puppies (at least 5 puppies in each group) are injected with each of the selected (e.g. 3) lineages of CDV isolates either as a single injection multivalent CDV vaccine or in separate, back-to-back injections of each of the 2-3 different genetic variants 3-4 weeks apart. This experiment identifies one or more broadly reacting CDV isolates that will elicit a higher level of titers against all the 34 CDV isolates. For example, isolates identified by RPCU analysis such as 09041474B are confirmed to be broadly reacting isolates due to shared codons of H protein. This translates into higher vaccine titers, better protection in challenge experiments, no clinical evidence of disease in vaccinated dogs (or alternatively, mild clinical symptoms), and longer duration of immunity. Moreover, CDV isolates selected using the RFCU will provide broad protection against other genetic and antigenic variants that are present in other continents.

Additional criteria are also used to select CDV isolates for use in a modified live virus vaccine, including the following:

A). CDV isolates should grow to high titers ($10^6$ or more) on an approved non-recombinant cell line such as Vero and canine kidney cell line. It is expected that CDV isolates will grow to higher titer (2-3 log higher titers) in the recombinant Vero+SLAM (Signaling Lymphocyte Activation Molecule) cell line. Although recombinant Vero SLAM is suitable for primary isolation of morbilliviruses, it is expensive to propagate CDV isolates therein due to the required addition of the selection antibiotic, gentamycin. CDV isolates that grow in one or more non-recombinant Vero cell lines that are approved by the USDA for animal vaccine production are selected for further propagation.

B). The speed of growth of CDV isolates is another criterion for evaluation. Most CDV isolates can grow to high titers in 3 days. However, the growth is slightly slower in conventional Vero cell line or dog kidney cells.

C). A few CDV isolates (n=5) from the major EW-branch are selected for further evaluation as vaccine antigens. A few isolates (n=5) from the second largest cluster (AM-2) are also selected as vaccine antigens. A few Arctic CDV isolates are also evaluated.

Example 7

Preparation of a Broad-Spectrum CDV Vaccine

A broadly reactive and predominant CDV isolate (e.g. a candidate identified by RPCU) is selected and confirmed by CDV-serum neutralization (CDV-SN) and/or plaque reduction tests. In some embodiments, this is a wild-type CDV isolate that is obtained from a fully vaccinated adult dog (above 5-6 months of age) that died in spite of complete vaccination (specifically 2 CDV vaccines).

Dogs are vaccinated subcutaneously or intranasally with the vaccine. The antibody titer against the vaccine strain is checked by CDV-SN or plaque reduction assays using serum from the vaccinated dog. The selected CDV strain shows high cross-reactivity with a panel of recent CDV isolates from the US belonging to all the CDV lineages circulating in the USA. All isolates are checked for cross-reactivity with sera from the vaccinated dog or ferrets (a laboratory model animal for CDV). A titer of ≥1:8, preferably ≥1:16, more preferably ≥1:32, and most preferably ≥1:64 after one vaccination of a naïve puppy 6-8 weeks of age is sufficient using a CDV-SN assay. In addition, the vaccine will not induce any cerebrospinal fluid (CSF) titers against CDV. Lack of CDV titers in the CSF indicates that the vaccine virus has not crossed the blood-brain barrier and is safe for use in puppies. A vaccine that is safe in puppies is very likely safe in dogs. In summary, all the guidelines of the Code of Federal Regulations (CFR) will be followed to develop an effective broad spectrum and safe CDV vaccine that will be approved by the USDA for use in dogs and other species susceptible to CDV.

Challenge studies are performed in which dogs are vaccinated with the broad spectrum CDV vaccine and then exposed to circulating, wild type CDV (e.g. 08080696 EW; 08081112 AM-2; 09011024 EW). These CDV viruses are genetically distinct and so are suitable as challenge viruses rather than as vaccine components. Dogs vaccinated with the vaccine preparation of the invention develop few or no symptoms of disease. Low-passage CDV isolates from the US as described herein can be used as the challenge virus. Unvaccinated controls will develop symptoms of CDV.

With respect to evaluating the results of challenge studies, diagnostic laboratories typically use relatively insensitive tests that often may not detect weakly CDV positive cases, such as those involving the nervous system. CDV may be detected using immunohistochemistry of brain samples after as animal dies or is sacrificed or euthanized. However, CSF and brain biopsy are expensive and invasive procedures and are not used routinely. In a recent study, urine has been described as a sensitive sample for detection of CDV in live dogs (Amude, A. M., A. A. Alfieri, and A. F. Alfieri. 2006. Antemortem diagnosis of CDV infection by RT-PCR in distemper dogs with neurological deficits without the typical clinical presentation. Vet. Res. Comm. 30:679-687). Thus, viruria (the presence of CDV virus or RNA in urine) may be an important parameter to include in vaccine-protection evaluation studies, and may be used non-invasively to detect the residual virus in CDV vaccinated dogs. Moreover, after extensive in depth diagnostic investigation, it has been found that CDV can cause residual CDV infections that were not evaluated in past CDV vaccine approval processes. Highly sensitive PCR assays are used and safety data is provided on the improved broad-spectrum CDV vaccines. Viruria is used as one of the parameters of CDV vaccine efficacy.

An ideal candidate CDV vaccine should protect against all genetically diverse CDV isolates. CDV isolates from other continents should be included to check global coverage of a broad-spectrum CDV vaccine. American-1 is not checked because this virus has not been found in the US in nature for the last 20 years, existing only in vaccines that have not been updated for 6 decades.

Example 8

Evaluation of CDV Vaccines in Ferret Models

Prior to testing the vaccines in a large animal model such as dogs, they can be evaluated in a ferret model. Ferrets are known to be suitable models of CDV infection and evaluation of CDV vaccines (Pillet et al., 2009: Ferrets as a model for morbillivirus pathogenesis, complications, and vaccines. Curr. Top. Microbiol. Immunol. 330:73-87). Ferrets are used to screen a large number of CDV vaccine candidates. The ferrets are vaccinated with attenuated modified live CDV, preferably a European-wildlife type (e.g. 09041474B). European-wildlife is preferred because a closely related cluster of these CDV viruses is causing vaccine failure in dogs in the US. Ferrets are checked for serum antibody titers against CDV after vaccination. The bleed dates are 0, 7, 14 and 21 days after vaccination. Low passage CDV viruses (e.g. European wildlife, or Arctic, or American-2) are then administered to the ferrets as challenge viruses.

Ferrets also have been documented to show CDV vaccine failure based on a recent case report (Zehnder et al., 2008: An unusual presentation of canine distemper virus infection in a domestic ferret (Mustela putorius furo) DOI: 10.1111/j). This domestic ferret, from the US, was repeatedly vaccinated using chick-embryo modified live virus vaccine 18 months prior to the onset of clinical CDV problems and annually thereafter. This vaccinated ferret developed a systemic CDV infection manifesting in skin lesions, with a prolonged course of disease yet with complete absence of respiratory and neurologic signs. Thus, CDV should be suspected in vaccinated ferrets with skin lesions (Zehnder, supra).

Example 9

Critical H-Protein Residues Undergoing Positive Selection Among CDV Lineages: Application to Diagnostics Depending on the specific needs of diagnostic clients, differential RT-PCR experiments and kits (including primers) are designed around critical H-residues (see Example 3) to differentially detect CDV wild types; to differentiate the Ondersteport-like vaccines from the Pfizer vaccine; and to differentiate CDV viruses down to the level of major CDV lineages using rapid assays with a 1 hour turnaround time. Ongoing monitoring of CDV viruses by complete H-gene

Example 10

Comparative Growth Characteristics of Three Selected CDV Isolates in Cell Culture From a panel of current CDV isolates at OADDL, two CDV isolates (09041474B and 08021509) were selected for depositing at the American Type Culture Collection (ATCC). The isolate 09041474B has been selected for developing a broad-spectrum CDV vaccine against current CDV isolates.

Three CDV isolates: 09041474B (European-Wildlife); 08021509 (American-2); and 07110098 (Arctic), were propagated in cell culture and observed for their speed of growth based on cytopathology, and the flasks were frozen when most of the monolayer (over 80%) was exhibiting cytopathology. The results showed that the speed of growth of these selected isolates was as follows: EW>>>AM-2>AR. In other words, the EW 09041474B isolate grew significantly faster than AM-2 and AR. The individual plaques of 09041474 were very large. At 23 hours, the entire flask of cells was covered with very large syncytia that touched each other (were fused) leaving almost no space between syncytia.

Isolate 08021509 (AM-2) displayed medium size plaques and grew as isolated plaques (non-fused plaques) initially. The speed of AM-2 isolate growth was at least half or less that of 09041474B. This isolate was harvested at about 96 hours after inoculation.

Arctic isolate 07110098 grew very slowly and the plaque size was small. Only a few isolated small plaques were detected. This isolate was not deposited at ATCC. This isolate was harvested at 7 days post infection. Even at one week, the monolayer showed only about 25% cytopathology. Based on these growth characteristics, this isolate is not suitable for vaccine preparation.

The type of active replication displayed by 09041474B is indicative of optimum (robust) growth that is expected from a CDV isolate that exhibits high "Relative Preferred Codon Usage (RPCU)". This isolate has been chosen for vaccine preparation because it will replicate to higher titers after inoculation and express relatively higher amounts of hemagglutinin protein, the major CDV immunogen. The ATCC deposit number for 09041474B is PTA-10596, deposited Jan. 21, 2010. The ATCC deposit number for 08021509 is PTA-10597, deposited Jan. 21, 2010.

Example 11

Full-Length Hemagglutinin Sequences of Two Exemplary/Selected CDV Isolates Deposited at ATCC, MD To derive the full-length sequences of the two CDV selected isolates, new primers were designed: 5'-TCGAAATCCTATGTGAGATCACT-3' (forward primer, CDVff1, SEQ IS NO: 40) and 5'-ATGCTGGAGATGGTT-TAATTCAATCG-3' (reverse primer, CDVHS-2, SEQ IS NO: 41). The RNA was extracted from the same batch of CDV isolates that were deposited at ATCC on Jan. 21, 2010. A QIAGEN viral RNA extraction kit was used according to the manufacturer's instructions. The primers for the full-length H-protein have been published (Lan N T, Yamaguchi R, Inomata A, Furuya Y, Uchida K, Sugano S, and S Tateyama. 2006. Comparative analyses of canine distemper viral isolates from clinical cases of canine distemper in vaccinated dogs. Vet. Microbiol. 115:32-42) but the RT-PCR protocol was not described. Thus, a new protocol was developed based on the properties of the primers.

A one step RT-PCR protocol was as follows: reverse transcription at 45° C. for 1 hour, denature at 95° C. for 3 minutes, followed by 30 cycles of 94° C. for 30 seconds, anneal at 50° C. for 30 seconds, extend at 72° C. for 2 minutes, final extension at 72° C. for 7 minutes, and hold the reaction at 4° C.

The reaction set up was as follows for each PCR reaction: 12.5 ul of 2× reaction buffer (Invitrogen, Cat#10928-034), both primers 1.7 ul each at (15 uM), $MgSO_4$ (50 mM), dNTPs (10 mM) 0.5 ul, and RT/platinum-Taq (0.5 ul). The PCR amplicons were purified by electrophoresis on 1.5% agarose gel. Correct full length amplicons about 2100 bp were observed. The amplicons were purified on a Promega Wizard column. Sequencing was performed at Noble Research Center, Stillwater, Okla. The forward and reverse sequences of both CDV isolates were subjected to sequence analysis (FIGS. 37 and 38). The CDV isolate 09041474B had the highest match with European-Wildlife CDV isolates. The CDV isolate 08021509 had the highest match with American-2 CDV isolates.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

---

The invention claimed is:

1. An isolated canine distemper virus (CDV) of European wildlife (EW) lineage comprising the characteristics of CDV 9041474B CDV-EW (ATCC Deposit No. PTA-10596).

2. An attenuated strain of CDV isolated in cell culture in which the CDV strain of claim 1 or a progeny strain thereof has been propagated.

3. An immunogenic composition, comprising
the isolated CDV of claim 1, or progeny thereof.

4. A method of eliciting an immune response to canine distemper virus in a subject in need thereof, comprising the step of
administering to said subject the immunogenic composition of claim 3.

5. An isolated nucleic acid molecule encoding the amino acid sequence of SEQ ID NO: 44, or the complement thereof.

6. The isolated nucleic acid molecule of claim 5 that comprises the nucleotide sequence of SEQ ID NO: 42, or the complement thereof.

7. An isolated polypeptide comprising the amino acid sequence of SEQ ID NO: 44.

8. An isolated canine distemper virus (CDV) of European wildlife (EW) lineage encoding a polypeptide comprising the amino acid sequence of SEQ ID NO: 44.

9. An isolated canine distemper virus (CDV) of American-2 (AM-2) lineage having the characteristics of CDV 08021509 CDV-AM-2 (ATCC Deposit No. PTA-10597).

10. An attenuated strain of CDV isolated in cell culture in which the CDV strain of claim 9 or a progeny strain thereof has been propagated.

11. An immunogenic composition, comprising
the isolated CDV of claim 9, or progeny thereof.

12. A method of eliciting an immune response to canine distemper virus in a subject in need thereof, comprising the step of
administering to said subject the immunogenic composition of claim 11.

13. An isolated nucleic acid molecule encoding the amino acid sequence of SEQ ID NO: 45, or the complement thereof.

14. The isolated nucleic acid molecule of claim 13 that comprises the nucleotide sequence of SEQ ID NO: 43, or the complement thereof.

15. An isolated polypeptide comprising the amino acid sequence of SEQ ID NO: 45.

16. An isolated canine distemper virus (CDV) of European wildlife (EW) lineage encoding a polypeptide comprising the amino acid sequence of SEQ ID NO: 45.

* * * * *